United States Patent
Ahmed et al.

(10) Patent No.: US 11,407,726 B2
(45) Date of Patent: Aug. 9, 2022

(54) USING STEREORETENTION FOR THE STEREOSELECTIVE FORMATION OF E-MACROCYCLES WITH RU-BASED OLEFIN METATHESIS CATALYSTS

(71) Applicant: California Institute of Technology, Pasadena, CA (US)

(72) Inventors: Tonia S. Ahmed, Pasadena, CA (US); T. Patrick Montgomery, Pasadena, CA (US); Robert H. Grubbs, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 234 days.

(21) Appl. No.: 16/770,153

(22) PCT Filed: Dec. 4, 2018

(86) PCT No.: PCT/US2018/063780
§ 371 (c)(1),
(2) Date: Jun. 5, 2020

(87) PCT Pub. No.: WO2019/113019
PCT Pub. Date: Jun. 13, 2019

(65) Prior Publication Data
US 2020/0385360 A1 Dec. 10, 2020

Related U.S. Application Data

(60) Provisional application No. 62/737,109, filed on Sep. 27, 2018, provisional application No. 62/609,596, filed on Dec. 22, 2017, provisional application No. 62/595,377, filed on Dec. 6, 2017.

(51) Int. Cl.
*C07D 313/00* (2006.01)
*B01J 31/22* (2006.01)

(52) U.S. Cl.
CPC .......... *C07D 313/00* (2013.01); *B01J 31/226* (2013.01); *B01J 31/2208* (2013.01); *B01J 31/2273* (2013.01); *B01J 2231/546* (2013.01); *B01J 2531/821* (2013.01)

(58) Field of Classification Search
None
See application file for complete search history.

(56) References Cited

U.S. PATENT DOCUMENTS

| 5,936,100 A | 8/1999 | Furstner et al. |
| 2016/0185821 A1 | 6/2016 | Mangold et al. |
| 2017/0022231 A1 | 1/2017 | Grubbs et al. |

OTHER PUBLICATIONS

Ahmed et al. 'A Highly Efficient Synthesis of Z-Macrocycles Using Stereoretentive, Ruthenium- Based Metathesis Catalysts', Angewandte Chemie International Edition, Jun. 23, 2017 (Jun. 23, 2017) vol. 56, pp. 11213-11216.
Ahmed et al. 'Using stereoretention for the synthesis of E-macrocycles with ruthenium-based ole fin metathesis catalysts', Chemical Science, Mar. 14, 2018 (Mar. 14, 2018), vol. 9, pp. 3580-3583; entire document.
International Preliminary Reporton Patentability received for PCT Patent Application No. PCT/US2018/063780, dated Jun. 18, 2020, 9 pages.
International Search Report and Written Opinion received for PCT Patent Application No. PCT/US18/063780, dated Apr. 19, 2019, 11 pages.
Lee et al. 'Stereoselectivity of Macrocyclic Ring-Closing Olefin Metathesis', Organic Letters, Jun. 17, 2000 (Jun. 17, 2000), vol. 2, pp. 2145-2147.
Schreiber et al. 'Iron/copper promoted fragmentation reactions of a-alkoxy hydroperoxides: Regio- and stereocontrolled fom,ation of olefin-containing macrolides', Tetrahedron, 1986, pp. 2945-2950;p. 2948.
Shen et al. 'Kinetically E-selective macrocyclic ring-closing metathesis', Nature, 19 Jan. 1, 2017 (Jan. 1, 2017), vol. 541, pp. 380-385; p. 383.

*Primary Examiner* — Joseph R Kosack
(74) *Attorney, Agent, or Firm* — Faegre Drinker Biddle & Reath LLP

(57) ABSTRACT

This invention relates generally to the synthesis of E-macrocycles using stereoretentive ruthenium olefin metathesis catalysts supported by dithioate ligands. Macrocycles were generated with excellent selectivity (>99% E) and in moderate to high/good yields (47% to 80% yield; 58% to 80% yield) from diene starting materials bearing two E-olefins or bearing one E-olefin and one terminal olefin, A variety of rings were constructed, ranging from 12- to 18-membered macrocycles, including the antibiotic recifeiolide. The invention has utility in the fields of organometallics and organic synthesis.

16 Claims, 5 Drawing Sheets

M = Mo, R = 1-adamantyl
M = W, R = 2,6-diisopropylphenyl

M = Mo, W

USING STEREORETENTION FOR THE STEREOSELECTIVE FORMATION OF E-MACROCYCLES WITH RU-BASED OLEFIN METATHESIS CATALYSTS

CROSS-REFERENCE TO RELATED APPLICATIONS

This application is a national stage application (under 35 U.S.C. § 371) of PCT/US2018/063780, filed Dec. 4, 2018, which claims benefit of U.S. Application Nos. 62/55,377, filed Dec. 6, 2017, 62/609,596, filed Dec. 22, 7017, and 62/737,109, filed Sep. 27, 2018, all of which are incorporated herein by reference in their entirety.

STATEMENT REGARDING FEDERALLY SPONSORED RESEARCH OR DEVELOPMENT

This invention was made with government support under GM031332 awarded by the National Institutes of Health, under CHE1502616 awarded by the National Science foundation and under N00014-14-1-0650 awarded by the Office of Naval Research. The government has certain rights in the invention.

TECHNICAL FIELD

This invention relates generally to the synthesis of E-macrocycles using stereoretentive ruthenium olefin metathesis catalysts supported by dithiolate ligands. Macrocycles were generated with excellent selectivity (>99% E) and in moderate to high/good yields (47% to 80% yield; 58% to 80% yield) from diene starting materials bearing two E-configured olefins or bearing one E-olefin and a terminal olefin. A variety of rings were constructed, ranging from 12- to 18-membered macrocycles, including the antibiotic recifeiolide. The invention has utility in the fields of organometallics and organic synthesis.

BACKGROUND

Ring-closing metathesis (RCM) has gained widespread use in organic synthesis for the production of macrocyclic frameworks (Grubbs, R. H., Wenzel, A. G., O'Leary, D. J., Khosravi, E., Eds. Handbook of Metathesis; Wiley-VCH: Weinheim, 2015.) This transition metal-catalyzed reaction is commonly used in the synthesis of many biologically active compounds, and olfactory compounds, such as pharmaceuticals, pheromones and musks. [(a) Michrowska, A.; Wawrzyniak, P.; Grela, K. Eur. J. Org. Chem. 2004, 2053. (b) Rimkus, G. G. The Handbook of Environmental Chemistry; Springer: Berlin, 2004; Vol. 3X. (c) Rowe, D. J. Chemistry and Technology of Flavors and Fragrances; Blackwell: Oxford, U. K., 2005. (d) Gradillas, A.; Perez-Castells, J. Angew. Chem., Int. Ed. 2006, 45, 6086. (e) Ohloff, G.; Pickenhagen, W.; Kraft, P. Scent and Chemistry: The Molecular World of Odors; Verlag Helvetica Acta: Zürich, 2011.] The stereochemistry of the olefin often governs the properties of these cyclic molecules. The stereochemistry of the olefin often governs the biological activity of these cyclic molecules, and the presence of small amounts of the other isomer in mixtures can often diminish their effectiveness. Consequently, the stereochemical purity of olefin mixtures is important. The separation of E- and Z-isomers can often be challenging, and thus methods for stereoselectively generating macrocycles have been the focus of many studies.

The synthesis of Z-macrocycles has been reported using an array of Ru-olefin metathesis catalysts, [Marx, V. M.; Herbert, M. B.; Keitz, B. K.; Grubbs, R. H. J. Am. Chem. Soc. 2013, 135, 94. (g) Higman, C. S.; Lummiss, J. A. M.; Fogg, D. E. Angew. Chem., Int. Ed. 2016, 55, 3552, W-, and Mo-based Yu, M.; Wang, C.; Kyle, A. F.; Jakubec, P.; Dixon, D. J.; Schrock, R. R.; Hoveyda, A. H. Nature 2011, 479, 88.] The steric environment of each of these catalysts is manipulated such that the substituents of the metallacyclobutane intermediate point favorably in the same direction, away from a repulsive substructure within the ligand architecture (FIG. 1). Cycloreversion of this syn intermediate gives the macrocycle with Z-configuration.

In 2013, Hoveyda and co-workers reported Ru-based catalysts bearing dithiolate ligands able to perform highly Z-selective cross metathesis from Z-olefin starting materials. [Koh, M. J.; Khan, R. K. M.; Torker, S.; Yu, M.; Mikus, M. S.; Hoveyda, A. H. Nature 2015, 517, 181.] In 2015, we demonstrated that these catalysts were further capable of cross metathesis between two E-olefins or between an E-olefin and a terminal olefin to generate E-products with high selectivity (>98% E). [Johns, A. M.; Ahmed, T. S.; Jackson, B. W.; Grubbs, R. H.; Pederson, R. L. Org. Lett. 2016, 18, 772.] This was the first reported example of highly E-selective cross metathesis, through kinetic control.

BRIEF DESCRIPTION OF THE FIGURES

FIG. 5. RCM of substrate 7 to form 12-membered macrocycle 8 using catalysts 2-4.

SUMMARY

Figure 1:
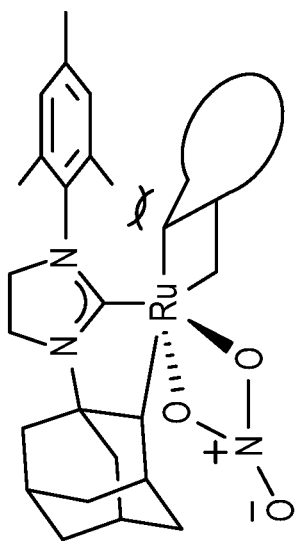
FIG. 1. Key metallacyclobutane intermediates for making Z-macrocycles using Mo-, W-, and Ru-based olefin metathesis catalysts.
Figure 1:
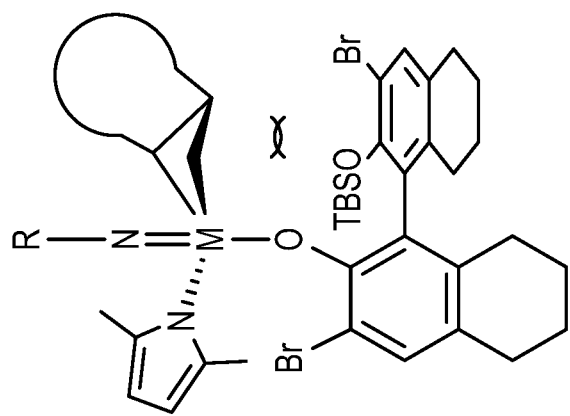
Figure 1:
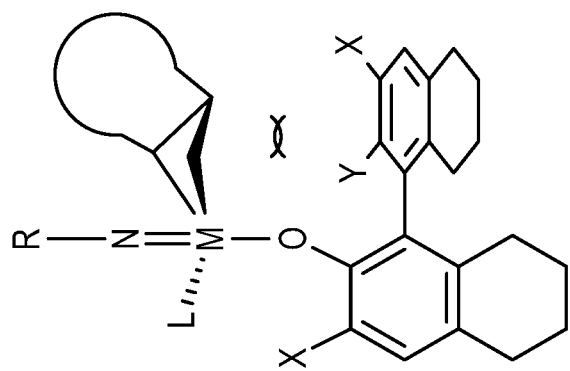
Figure 2A:
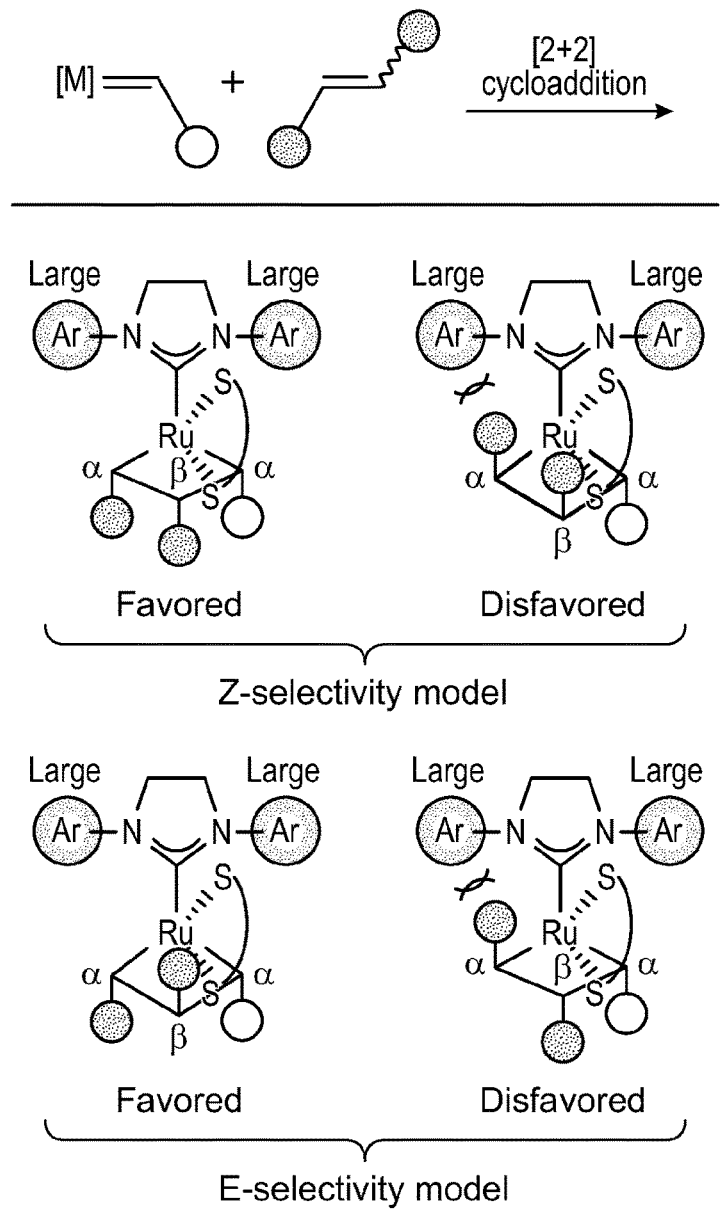
FIG. 2. Models for selectivity in cross metathesis using stereoretentive olefin metathesis catalysts for a) Ru catalysts and b) Mo catalysts.
Figure 2B:
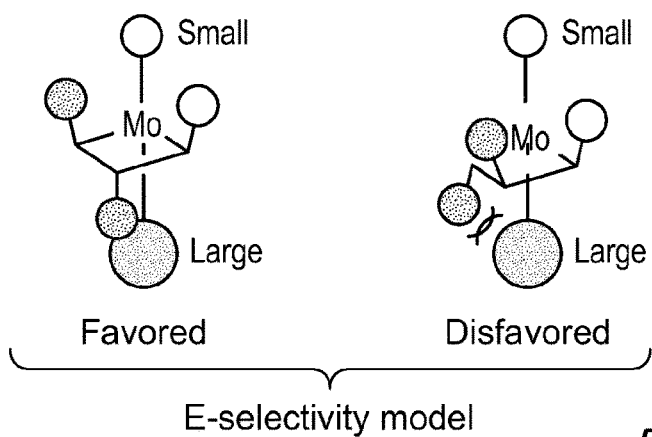
Figure 3:
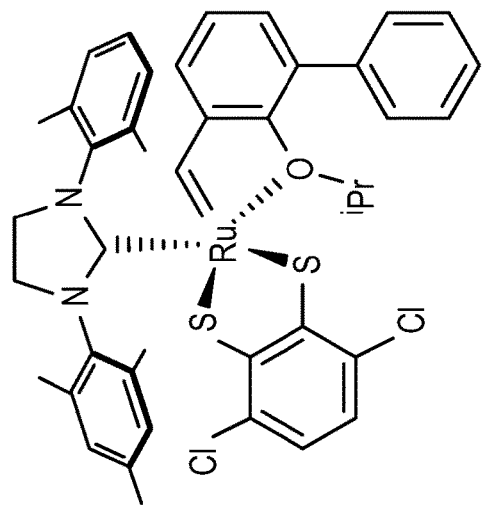
FIG. 3. Series of fast-initiating Ru-based catalysts for achieving efficient synthesis of highly E-products in cross metathesis.
Figure 3:
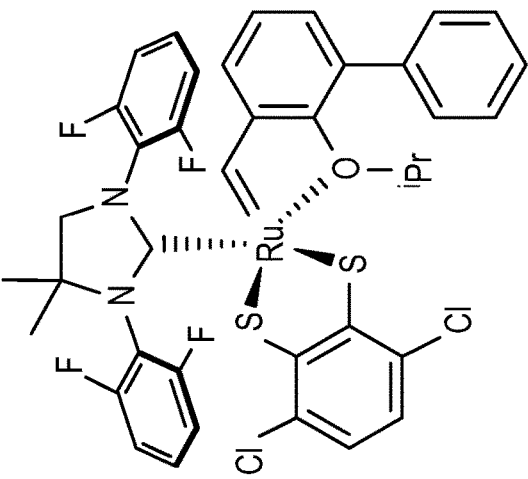
Figure 3:
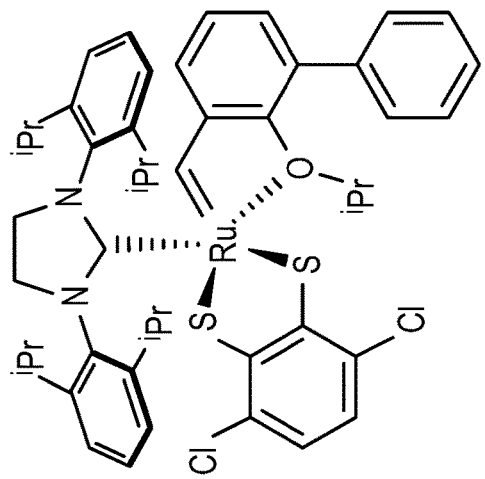
Figure 3:
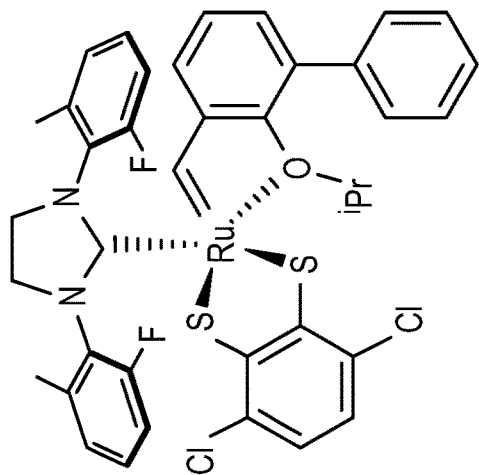

The stereoretention exhibited by catalysts 2, 3 and 4, shown in FIG. 3, is proposed to arise from the α substituents of the metallacyclobutane facing favorably down, away from the large N-aryl groups of the N-heterocyclic carbene (NHC) ligand (FIG. 2a). Depending on the stereochemistry of the starting olefin, the β substituent can either point down or up into the open space between the two N-aryl groups in front of the imidazol-2-ylidene ring. Given that the olefin starting material is cis, the β substituent in the favored intermediate will point down, and the product formed after cycloreversion will be cis. Conversely, if the starting olefin is trans, the β substituent will point up, and the product from the favored intermediate will be trans. Schrock and Hoveyda soon thereafter reported Mo-based catalysts capable of a similar transformation, by which E-selectivity in cross metathesis is achieved from E-alkenyl halide starting materials (FIG. 2b). (Nguyen, T. T.; Koh, M. J., Shen, X.; Romiti, F.; Shrock, R. R.; Hoveyda, A. H.; Science 2016, 352, 569.)

E-selective cross metathesis using stereoretentive Ru-based catalysts was often marred by low yields. Studies performed in our group showed that a large contributing factor to this low activity is slow catalyst initiation in reactions of these catalysts with E-olefins. (Ahmed, T. S.; Grubbs, R. H. *J. Am Chem. Soc.* 2017, 139, 1532.) A series of fast-initiating catalysts 1-4 was reported to significantly improve activity of stereoretentive catalysts in highly E-selective reactions (FIG. 3).

The first example of the stereoselective synthesis of macrocycles using stereoretention was reported using Mo-based catalysts to generate E-macrocycles (91->98% E) from diene substrates containing an E-alkenyl-B(pinacolato) moiety and a terminal olefin. (Shen, X.; Nguyen, T. T; Koh, M. J.; Xu, D.; Speed, A. W. H.; Schrock, R. R.; Hoveyda, A. H. Nature 2017, 541, 380.)

We recently reported a highly efficient synthesis of Z-macrocycles (95-99% Z) using stereoretention with Ru-based catalysts and substrates bearing a Z-olefin and a terminal olefin. (Ahmed, T. S.; Grubbs, R. H. Angew. Chem. Int. Ed. 2017, 56, 11213.) Hoveyda and coworkers then provided further examples of Z-macrocyclizations using other stereoretentive Ru catalysts and one example of E-macrocycle synthesis using, (Xu, C.; Shen, X.; Hoveyda, A. H.; J. Am. Chem. Soc. 2017, 139, 10919.) Additional methods of synthesizing E-macrocycles without stereoretention, include Z-selective ethenolysis of stereochemical mixtures of macrocycles (Marx, V. M.; Herbert, M. B.; Keitz, B. K.; Grubbs, R. H. J. Am. Chem. Soc, 2013, 135, 94. Higman, C. S.; Lummiss, J. A.; Fogg, D. E. Angew. Chem., Ed. 2016, 55, 3552) and alkyne metathesis followed by E-selective semihydrogenation catalyzed by Cp*Ru(COD)Cl/AgOTf. (Radkowski, K.; Sundararaju, B.; Fürstner, A. Angew. Chem., Int. Ed. 2013, 52, 355.)

Figure 4:
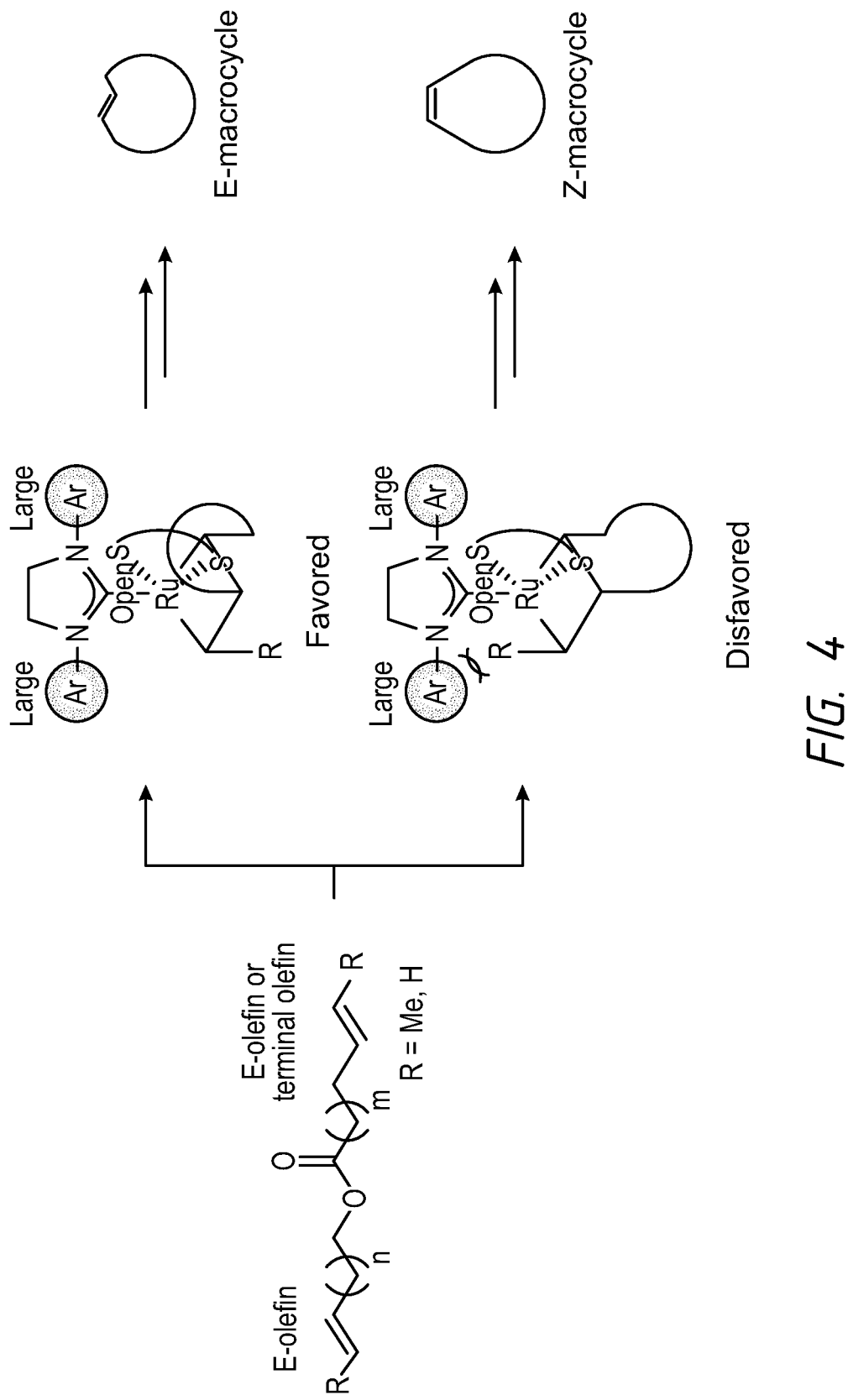
FIG. 4. Proposed favored and disfavored intermediates in the formation of macrocycles from dienes containing an E-olefin.

We anticipated that E-macrocycles could be generated from diene starting materials containing an E-olefin using stereoretentive Ru catalysts. The proposed model favored metallacyclobutane intermediate avoiding steric clashing of the α substituent with the N-aryl group as proposed in the disfavored intermediate (FIG. 4). Catalysts 2-4 were chosen for studying RCM with these substrates as they had previously exhibited remarkable activity and selectivity in cross metathesis of E-olefins. (Ahmed, T. S.; Grubbs, R. H. *J. Am. Chem. Soc.* 2017, 139, 1532.)

Based on the proposed model for stereoretention, we expected that reducing the ortho substituent size of the N-aryl groups would allow for better accommodation of the β substituent in E-selective RCM. Therefore, the reactivity of catalyst 4 with E-olefins would be greater than catalyst 3, which would furthermore be greater than that of catalyst 2.

Using the conditions, we had established in the synthesis of Z-macrocycles, we attempted to make E-macrocycle 6 from diene starting material 5 bearing an E-olefin and a terminal olefin (Scheme 1).

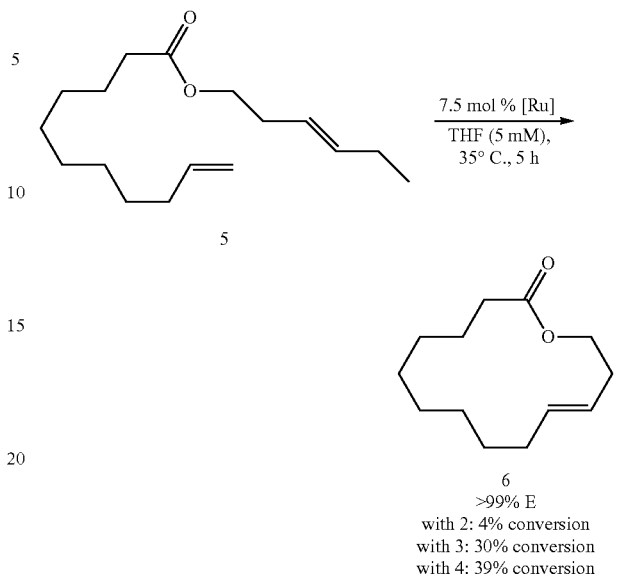

Scheme 1. Synthesis of E-macrocycle 6 from 5 using catalysts 2-4.

6
>99% E
with 2: 4% conversion
with 3: 30% conversion
with 4: 39% conversion The conversion was determined by $^1$H NMR, and the selectivity was determined using gas chromatography.

Catalysts 2, 3, and 4 reached a maximum of 4%, 30%, and 39% conversion, respectively, to the desired product with high E-selectivity (>99% E) at 35° C. This low conversion is presumably a result of the instability and decomposition of unstable Ru methylidenes formed in this reaction. This result was in agreement with previous studies showing that cross metathesis between E-olefins and terminal olefins using these catalysts is challenging. Previous studies have shown that reaction of these catalysts with E-olefins is considerably slower than with Z-olefins. (Ahmed, T. S.; Grubbs, R. H. J. Am. Chem. Soc. 2017, 139, 1532). Therefore, it is proposed that Ru methylidenes persist longer in solution in reactions with E-olefins and are accordingly more prone to decomposition in reactions with E-olefins than in those with Z-olefins.

Figure 5A:
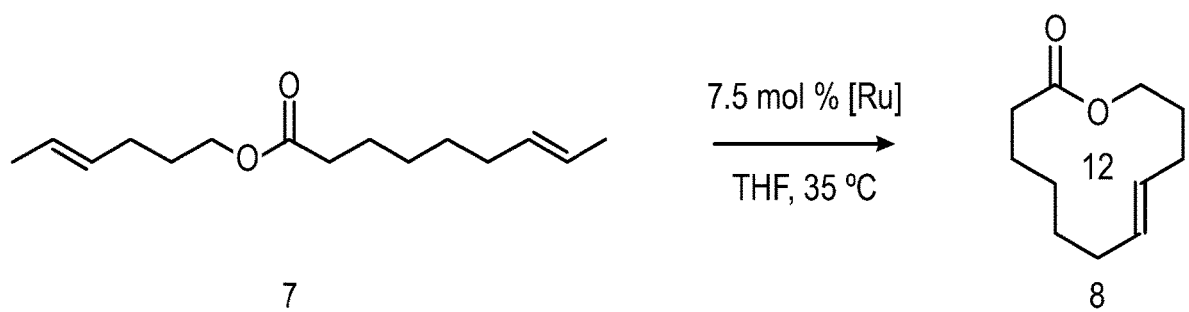
FIG. 5a. Conversion determined by $^1$H NMR. Selectivity determined using gas chromatography. Plot of conversion vs. time for RCM of 7 to 8 using catalysts 2-4.
Figure 5A:
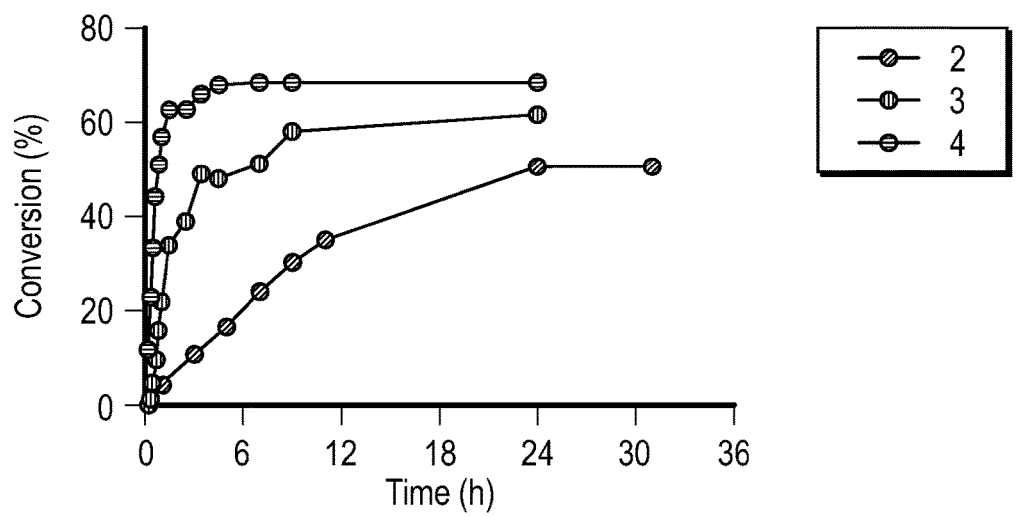

To avoid the formation of Ru methylidenes, diene substrates containing two E-olefins were synthesized. Using substrate 7, the formation of the 12-membered macrocycle 8 was monitored using catalysts 2-4 at 35° C. (FIG. 5a). Catalyst 4 displayed remarkable activity in this reaction. After 30 minutes, the reaction reached 30% conversion to 8 with catalyst 4, while catalyst 3 provided just 5% conversion and catalyst 2 reached 2% conversion. After just 1 h, catalyst 4 achieved 57% conversion. To reach the same conversion, catalyst 3 required 9 h, while catalyst 2 never attained this level of conversion. A maximum of 70% conversion to 8 was achieved using catalyst 4, while catalyst 3 reached a maximum of 62% conversion and catalyst 2 gave 51% conversion. With each of these catalysts, high E-selectivity (>99% E) was maintained throughout the course of the reaction.

Figure 5B:
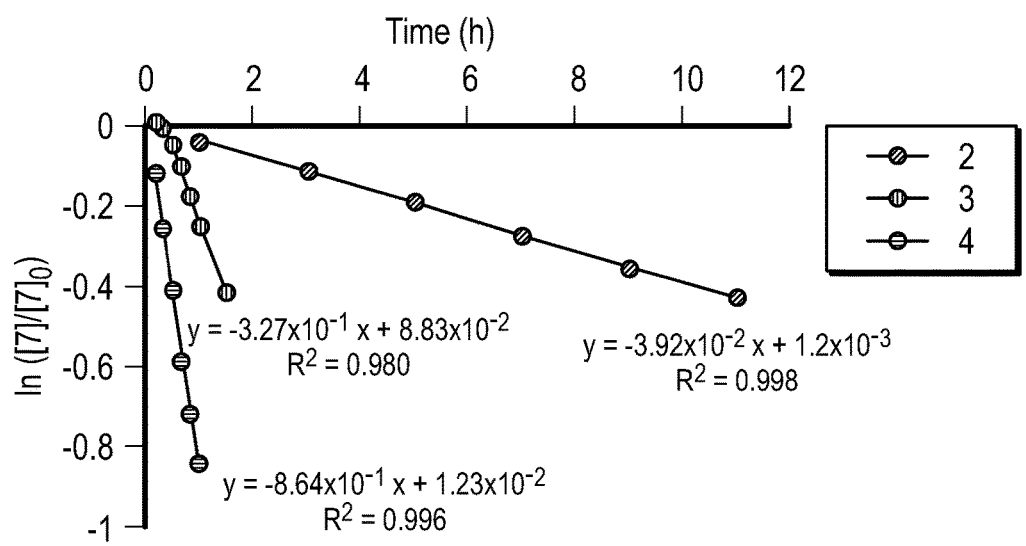
FIG. 5b. Kinetic studies show differences in activity among catalysts. Plot of ln([7]/[7]0) vs. time for this reaction. Conversion determined by $^1$H NMR. Selectivity determined using gas chromatography.

Kinetic studies elucidate marked differences in activity among the catalysts tested, with catalyst 4 providing meaningful yields of products in much shorter reaction times than stereoretentive catalysts 2 and 3. These kinetic NMR experiments were performed on a Varian 600 MHz spectrometer with an AutoX probe. Assuming first-order kinetics with respect to diene 7, rate constants were measured for catalysts 2, 3, and 4 under these reaction conditions and were determined to be $3.92 \times 10^{-2}$ s$^{-1}$, $3.27 \times 10^{-1}$ s$^{-1}$, and $8.64 \times 10^{-1}$ s⁻¹, respectively (FIG. 5b). The relative rate constants hence have values of $k_{rel4}=k_{obs4}/k_{obs2}=220$ and $k_{rel3}=k_{obs3}/k_{obs2}=8.46$. Given the observed low reactivity of E-olefins with these catalysts, these large disparities in activity highlight the difference in the ability of each of these catalysts to provide significant yields of products.

Using an array of diene substrates bearing two E-olefins or bearing one E-olefin and one terminal olefin, as represented by generic Formula (II) in Scheme 2, wherein n is 1, 2, 3, 4, 5 or 6; m is 4, 5, 6, or 7; R is H, linear or branched $C_{1-12}$ alkyl; $R^{r2}$ is H or linear $C_{1-3}$ alkyl; and $R^{r1}$ is H, linear or branched $C_{1-2}$ alkyl; with the proviso that only one of R and $R^{r1}$ can be H; a variety of macrocyclic lactones, represented by generic Formula (III), were synthesized, ranging in size from 12- to 18-membered rings.

Scheme 2. General reaction for synthesizing E-macrocycles

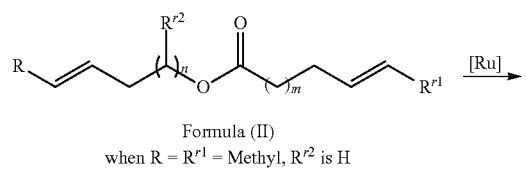

Formula (II)
when R = $R^{r1}$ = Methyl, $R^{r2}$ is H

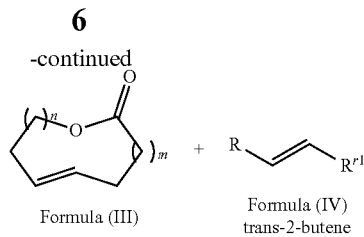

Formula (III)  Formula (IV)
                trans-2-butene

Each of these macrocycles, was generated with the concomitant loss of a structure represented by Formula (IV), (in the case when R and $R^{r1}$ are both methyl Formula (IV) is a gas trans-2-butene), which could be easily removed from the reaction mixture. Using catalyst 2, products were obtained in moderate to good yields (47%-66%) and with high E-selectivity (>99% E) in 24 h at 35° C.

Much shorter reaction times could be achieved using catalyst 4, which provided these macrocycle products in 5 h in good to high yields (60%-80%) while high E-selectivity was maintained (>99% E). Using catalyst 4, the antibiotic recifeiolide 9 was synthesized in 80% yield with >99% E-selectivity in 8 h. Longer reaction times were likely required for this reaction due to steric encumbrance of the methyl group in the starting material.

TABLE 1

Synthesis of E-macrocyclic lactones using catalysts 2 and 4.

| E-macrocycle | | | | |
|---|---|---|---|---|
| | 12 (8) | 12 (9) | 13 (10) | 14 (6) |
| Catalyst 4 | | | | |
| yield (%)* | 60 | 80 | 75 | 65 |
| E-selectivity (%)** | >99 | >99 | >99 | >99 |
| Time (h) | 5 | 8 | 5 | 5 |
| Catalyst 2 | | | | |
| yield (%)* | 47 | 61 | 57 | 58 |
| E-selectivity (%)** | >99 | >99 | >99 | >99 |
| Time (h) | 24 | 24 | 24 | 24 |
| E-macrocycle | 14 (11) | 15 (12) | 16 (13) | 18 (14) |

TABLE 1-continued

Synthesis of E-macrocyclic lactones using catalysts 2 and 4.

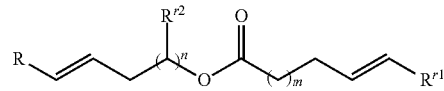

| Catalyst 4 | | | | |
|---|---|---|---|---|
| yield (%)* | 67 | 70 | 70 | 63 |
| E-selectivity (%)** | >99 | >99 | >99 | >99 |
| Time (h) | 5 | 5 | 5 | 5 |
| Catalyst 2 | | | | |
| yield (%)* | 60 | 63 | 66 | 64 |
| E-selectivity (%)** | >99 | >99 | >99 | >99 |
| Time (h) | 24 | 24 | 24 | 24 |

*Isolated yields.
**Stereoselectivity determined by gas chromatography.

We have demonstrated that stereoretentive ruthenium olefin metathesis catalysts supported by dithiolate ligands can be used in the synthesis of E-macrocycles with exceptional selectivity (>99% E) from diene starting materials bearing two E-olefins. Catalyst 4 delivers meaningful yields of macrocyclic products in appreciably shorter reaction times than other stereoretentive Ru catalysts 2 and 3 as evidenced by kinetic studies. Using this method, 12- to 18-membered macrocycles, including recifeiolide, were synthesized in moderate to high yield (47%-80% yield).

In another embodiment, the invention provides a method that produces a compound (i.e., a product, olefin product; e.g., ring-close metathesis product, an E-macrocyclic product) having a carbon-carbon double bond (e.g., a product internal olefin) in an E/Z selectivity ratio of 95/5, or 96/4, or 97/3, or 98/2, or in some cases, of 99/1. In some cases, 100% of the carbon-carbon double bond produced in the metathesis reaction may have an E-configuration. The E- or trans selectivity may also be expressed as a percentage of product formed (e.g., ring-close metathesis product, E-macrocyclic product).

In one embodiment, the invention provides a method for performing a ring closing metathesis reaction, comprising contacting a diene starting material bearing two E-olefins or bearing one E-olefin and a terminal olefin, in the presence of a stereoretentive ruthenium olefin metathesis catalyst to promote the formation of at least one E-macrocycle with 95%, or 98%, or 99% or >99% E-selectivity.

In one embodiment, the invention provides a method for producing at least one E-macrocyclic product represented by Formula (III), Formula (III)

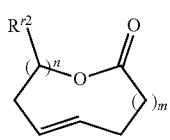

wherein: $R^{r2}$ is H or linear $C_{1-3}$ alkyl; n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and a terminal olefin represented by Formula (II)

Formula (II)

wherein: n is 1, 2, 3, 4, 5 or 6;
m is 4, 5, 6 or 7;
R is H, linear or branched $C_{1-12}$alkyl;
$R^{r1}$ is H, linear or branched $C_{1-12}$alkyl;
$R^{r2}$ is H or linear $C_{1-3}$ alkyl; and with the proviso that only one of R and $R^{r1}$ can be H; to a macrocyclic ring-closing metathesis reaction in the presence of a stereoretentive ruthenium olefin metathesis catalyst represented by Formula (I), Formula (I)

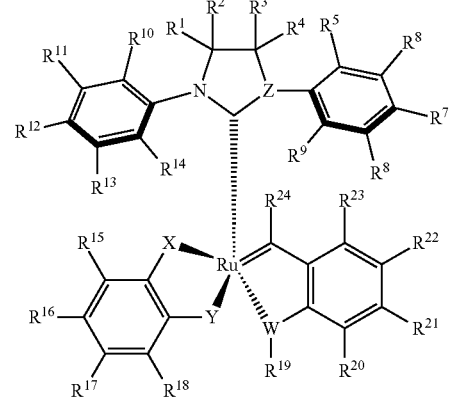

wherein
X is O or S;
Y is O or S;
Z is N or $CR^{32}$;
W is O, halogen, $NR^{33}$ or S;

$R^1$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^2$ can form a spiro compound or together with $R^3$ or together with $R^4$ can form a polycyclic ring;

$R^2$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^1$ can form a spiro compound or together with $R^3$ or together with $R^4$ can form a polycyclic ring;

$R^3$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ or together with $R^1$ can form a polycyclic ring or together with $R^4$ can form a spiro compound;

$R^4$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^3$ can form a spiro compound or together with $R^2$ or together with $R^1$ can form a polycyclic ring;

$R^5$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^6$ can form an optionally substituted polycyclic ring;

$R^6$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^5$ or together with $R^7$ can form an optionally substituted polycyclic ring;

$R^7$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl optionally substituted $C_{3-8}$ cycloalkenyl, or together with $R^6$ or together with $R^8$ can form an optionally substituted polycyclic ring;

$R^8$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$—, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^7$ or together with $R^9$ can form an optionally substituted polycyclic ring;

$R^9$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^8$ can form an optionally substituted polycyclic ring;

$R^{10}$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ can form an optionally substituted polycyclic ring;

$R^{11}$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{10}$ or together with $R^{12}$ can form an optionally substituted polycyclic ring;

$R^{12}$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ or together with $R^{13}$ can form an optionally substituted polycyclic ring;

$R^{13}$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{14}$ or together with $R^{12}$ can form an optionally substituted polycyclic ring;

$R^{14}$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{13}$ can form a polycyclic ring;

$R^{15}$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ can form an optionally substituted polycyclic ring;

$R^{16}$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{13}$ or together with $R^{17}$ can form an optionally substituted polycyclic ring;

$R^{17}$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ or together with $R^{16}$ can form an optionally substituted polycyclic ring;

$R^{18}$ is H, optionally substituted $C_{1-24}$ alkyl, halogen, —C(O)$R^{25}$, —OR$^{26}$, CN, —NR$^{27}R^{28}$, NO$_2$, —CF$_3$, —S(O)$_xR^{19}$, —P(O)(OH)$_2$, —OP(O)(OH)$_2$, —SR$^{31}$, optionally substituted heterocycle, optionally substituted $C_{3-8}$ cycloalkyl, optionally substituted $C_{1-24}$ aryl or optionally substituted $C_{3-8}$ cycloalkenyl, or together with $R^{17}$ can form an optionally substituted polycyclic ring;

$R^{19}$ is H, optionally substituted $C_{1-24}$ alkyl, —C(R$^{34}$)(R$^{35}$)COOR$^{36}$, —C(R$^{34}$)(R$^{35}$)C(O)H, —C(R$^{34}$)(R$^{35}$)C(O)R$^{37}$, —C(R$^{34}$)(R$^{35}$)CR$^{38}$(OR$^{39}$)(OR$^{40}$), —C(R$^{34}$)(R$^{35}$)C(O)NR$^{41}R^{42}$, —C(R$^{34}$)(R$^{35}$)C(O)NR$^{41}$OR$^{40}$, —C(O)R$^{25}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{33}$ can form an optionally substituted heterocyclic ring or is nil when W is halogen;

$R^{20}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted Cm cycloalkenyl or together with $R^{21}$ can form a polycyclic ring;

$R^{21}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{20}$ or together with $R^{22}$ can form a polycyclic ring;

$R^{22}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ or together with $R^{23}$ can form a polycyclic ring;

$R^{23}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{22}$ can form a polycyclic ring;

$R^{24}$ is H, optionally substituted $C_{1-24}$ alkyl, halogen, —C(O)$R^{25}$, —OR$^{26}$, CN, —NR$^{27}$R$^{23}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, OR$^{30}$, NR$^{27}$R$^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is H, optionally substituted $C_{1-24}$ alkyl, OR$^2$, —NR$^{27}$R$^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{33}$ is H, optionally substituted $C_{1-24}$ alkyl, optionally substituted $C_{3-8}$ cycloalkyl, optionally substituted heterocycle, optionally substituted $C_{5-24}$ aryl, optionally substituted $C_{3-8}$ cycloalkenyl, or together with $R^{19}$ can form an optionally substituted heterocyclic ring;

$R^{34}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{35}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{36}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{37}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{38}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{39}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{40}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{41}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{42}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and x is 1 or 2.

These and other aspects of the invention will be apparent to the skilled artisan in light of the following detailed description and examples.

DETAILED DESCRIPTION

Terminology and Definitions

Unless otherwise indicated, the invention is not limited to specific reactants, reaction conditions, or the like, as such may vary. It is also to be understood that the terminology used herein is for the purpose of describing particular embodiments and is not to be interpreted as being limiting.

As used in the specification and the appended claims, the singular forms "a," "an," and "the" include plural referents unless the context clearly dictates otherwise. Thus, for example, reference to "a substituent" encompasses a single substituent as well as two or more substituents, and the like.

As used in the specification and the appended claims, the terms "for example", "for instance", "such as" or "including" are meant to introduce examples that further clarify more general subject matter. Unless otherwise specified, these examples are provided only as an aid for understanding the invention and are not meant to be limiting in any fashion.

In this specification and in the claims that follow, reference will be made to a number of terms, which shall be defined to have the meanings as described herein.

The term "alkyl" as used herein, refers to a linear, branched, or cyclic saturated hydrocarbon group typically although not necessarily containing 1 to 24 carbon atoms, preferably 1 to 12 carbon atoms, such as methyl (Me), ethyl (Et), n-propyl (Pr or n-Pr), isopropyl (i-Pr), n-butyl (Bu or n-Bu), isobutyl (i-Bu), t-butyl (t-Bu), octyl (Oct), decyl, and the like, as well as cycloalkyl groups such as cyclopentyl (Cp), cyclohexyl (Cy) and the like. Generally, although again not necessarily, alkyl groups herein contain 1 to about 8 carbon atoms. The term "lower alkyl" refers to an alkyl group of 1 to 6 carbon atoms, and the specific term "cycloalkyl" refers to a cyclic alkyl group, typically having 3 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to 24 carbon atoms containing at least one double bond, such as ethenyl, n-propenyl, iso-propenyl, n-butenyl, iso-butenyl, octenyl, decenyl, tetradecenyl, hexadecenyl, and the like. Preferred alkenyl groups herein contain 2 to 12 carbon atoms. The term "lower alkenyl" refers to an alkenyl group of 2 to 6 carbon atoms, and the specific term "cycloalkenyl" refers to a cyclic alkenyl group, preferably having 3 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to 24 carbon atoms containing at least one triple bond, such as ethynyl, n-propynyl, and the like. Preferred alkynyl groups herein contain 2 to 12 carbon atoms. The term "lower alkynyl" refers to an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkynylene" as used herein refers to a difunctional alkynyl group, where "alkynyl" is as defined above.

The term "alkoxy" as used herein refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 6 to 10 carbon atoms. Exemplary aryl groups contain one aromatic ring or two fused or linked aromatic rings, e.g., phenyl (Ph), naphthyl, biphenyl, diphenylether, diphenylamine, benzophenone, phenanthryl and the like. "Substituted aryl" refers to an aryl moiety substituted with one or more substituent groups, and the terms "heteroatom containing aryl" and "heteroaryl" refer to aryl substituents in which at least one carbon atom is replaced with a heteroatom, as will be described in further detail herein.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 6 to 10 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, without limitation, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, —(CO)-aralkyl, —(CO)-alkaryl, —(CO)-alkenyl, or —(CO)-alkynyl, and the term "acyloxy" refers to substituents having the formula —O(CO)-alkyl, —O(CO)-aryl, —O(CO)-aralkyl, —O(CO)-alkaryl, —O(CO)-alkenyl, or —(CO)-alkynyl wherein "alkyl," "aryl", "aralkyl", "alkaryl", "alkenyl", and "alkynyl" are as defined above. The acetoxy group (—O(CO)CH$_3$, often abbreviated as —OAc) is a common example of an acyloxy group.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The term "polycyclic ring" refers to alicyclic or aromatic groups that may or may not be substituted and/or heteroatom containing, and that have at least two closed rings tethered, fused, linked via a single bond or bridged. Polycyclic rings include without limitation naphthyl, biphenyl, phenanthryl and the like.

The term "spiro compound" refers to a chemical compound, that presents a twisted structure of two or more rings (a ring system), in which 2 or 3 rings are linked together by one common atom, The terms "halo" and "halogen" and "halide" are used in the conventional sense to refer to a fluorine (F), chlorine (Cl), bromine (Br), or iodine (I) substituent.

The terms "cis"/"Z" and "trans"/"E" as used herein, are used interchangeably and refer to the geometry of the double bonds.

"Hydrocarbyl" refers to univalent hydrocarbyl radicals containing 1 to 24 carbon atoms, most preferably 1 to 12 carbon atoms, including linear, branched, cyclic, saturated and unsaturated species, such as alkyl groups, alkenyl groups, alkynyl groups, aryl groups, and the like. The term "lower hydrocarbyl" refers to a hydrocarbyl group of 1 to 6 carbon atoms, preferably 1 to 4 carbon atoms, and the term "hydrocarbylene" refers to a divalent hydrocarbyl moiety containing 1 to 24 carbon atoms, preferably 1 to 12 carbon atoms, including linear, branched, cyclic, saturated and unsaturated species. The term "lower hydrocarbylene" refers to a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include without limitation alkoxyaryl, alkylsulfanyl-substituted alkyl, N-alkylated amino alkyl, and the like. Examples of heteroaryl substituents include without limitation pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include without limitation pyrrolidino, morpholino, piperazino, piperidino, etc.

By "substituted" as in "substituted hydrocarbyl", "substituted alkyl", "substituted aryl", and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl) ($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano(-C≡N), cyanato (—O—C≡N), thiocyanato (—S—C≡N), isocyanate (—NCO), thioisocyanate (—NCS), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino ((—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CRNH where, R includes without limitation H, $C_1$-$C_{24}$ alkyl, $C_1$-$C_{24}$ aryl, $C_6$-$C_{24}$ alkaryl, $C_6$-$C_{24}$ aralkyl, etc.), $C_2$-$C_{20}$ alkylimino (—CRN(alkyl), where R includes without limitation H, $C_1$-$C_{24}$ alkyl, $C_5$-$C_{24}$ aryl, $C_6$-$C_{24}$ alkaryl, $C_6$-$C_{24}$ aralkyl, etc.), arylimino (—CRN(aryl), where R includes without limitation H, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R includes without limitation alkyl or other hydrocarbyl), phosphono (—P(O)(OH)$_2$), phospho (—PO$_2$), phosphino (—PH$_2$), silyl (—SiR$_3$ wherein R is H or hydrocarbyl), and silyloxy (—O-silyl); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl", "functionalized alkyl", "functionalized olefin", "functionalized cyclic olefin", and the like, is meant that in the hydrocarbyl, alkyl, olefin, cyclic olefin, or other moiety, at least one H atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above mentioned hydrocarbyl moieties may be further substituted with one or more functional groups or additional hydrocarbyl moieties such as those specifically mentioned above. Analogously, the above-mentioned hydrocarbyl moieties may be further substituted with one or more functional groups or additional hydrocarbyl moieties as noted above.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "terminal olefin" as used herein means an olefin wherein one of the olefinic carbons (i.e., the carbons of the carbon-carbon double bond) is substituted by at least one non-hydrogen substituent and the other olefinic carbon is unsubstituted.

The term "nil", as used herein, means absent or nonexistent.

The term "sulfhydryl" as used herein, represents a group of formula "—SH".

The term "hydroxyl" as used herein, represents a group of formula "–OH".

The term "carbonyl" as used herein, represents a group of formula "—C(O)—".

The term "ketone" as used herein, represents an organic compound having a carbonyl group linked to a carbon atom such as —C(O)$R^x$, wherein $R^x$ can be alkyl, aryl, cycloalkyl, cycloalkenyl, heterocycle as defined above.

The term "ester" as used herein, represents an organic compound having a carbonyl group linked to a carbon atom such as —C(O)O$R^x$ wherein $R^x$ can be alkyl, aryl, cycloalkyl, cycloalkenyl, heterocycle as defined above.

The term "amine" as used herein, represents a group of formula "—N$R^x R^y$", wherein $R^x$ and $R^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—SO$_2$—".

The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)OH".

The term "nitro" as used herein, represents a group of formula "—NO$_2$".

The term "cyano" as used herein, represents a group of formula "—CN".

The term "amide" as used herein, represents a group of formula "—C(O)N$R^x R^y$", wherein $R^x$ and $R^y$ can be the same or independently H, alkyl, aryl, cycloalkyl, cycloalkenyl, heterocycle as defined above.

The term "sulfonamide" as used herein, represents a group of formula "—S(O)$_2$N$R^x R^y$" wherein $R^x$ and $R^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Functional groups may be protected in cases where the functional group interferes with the metathesis catalyst, and any of the protecting groups commonly used in the art may be employed. Acceptable protecting groups may be found, for example, in Greene et al., Protective Groups in Organic Synthesis, 5th Ed. (New York: Wiley, 2014). Examples of protecting groups include acetals, cyclic acetals, boronate esters (boronates), cyclic boronate esters (cyclic boronates), carbonates, or the like. Examples of protecting groups include cyclic acetals or cyclic boronate esters.

E-Macrocyclic Products

The E-macrocyclic products of the invention, are twelve, thirteen, fourteen, fifteen, sixteen or eighteen-membered rings, comprising an internal olefin, in 95%, or 98%, or 99% or >99% E-selectivity.

In one embodiment, the E-macrocyclic product is a twelve, thirteen, fourteen, fifteen, sixteen or eighteen-membered rings, comprising an internal olefin in 95%, or 98%, or 99% or >99% E-selectivity, and is represented by the structure of Formula (III), wherein: $R'^2$ is H or linear $C_{1-3}$ alkyl; n is 1, 2, 3, 4, 6 or 7; and m is 4, 5, 6 or 7.

In another embodiment, the E-macrocyclic product is a twelve, fourteen, or fifteen-membered rings, comprising an internal olefin, in 95%, or 98%, or 99% or >99% E-selectivity represented by the structure of Formula (III), wherein $R'^2$ is H; n is 2; and m is 4, 6 or 7.

In another embodiment, the E-macrocyclic product is a twelve, thirteen, or fourteen-membered rings, comprising an internal olefin, in 95%, or 98%, or 99% or >99% E-selectivity is represented by the structure of Formula (III), wherein $R'^2$ is H or Me; n is 1; and m is 5, 6 or 7.

In another embodiment, the E-macrocyclic product is a twelve-membered ring, comprising an internal olefin, in 95%, or 98%, or 99% or >99% E-selectivity is represented by the structure of Formula (III), wherein $R'^2$ is Me; n is 1; and m is 5.

In another embodiment, the E-macrocyclic product is a sixteen-membered ring, comprising an internal olefin, in 95%, or 98%, or 99% or >99% E-selectivity represented by the structure of Formula (III), wherein $R'^2$ is H; n is 3; and m is 7.

In another embodiment, the E-macrocyclic product is na eighteen-membered ring, comprising an internal olefin, in 95%, or 98%, or 99% or >99% E-selectivity represented by the structure of Formula (III), wherein $R'^2$ is H; n is 5; and m is 7.

In one embodiment, the E-macrocyclic product has a carbon-carbon double bond in E-configuration and is represented by the structure of Formula (V):

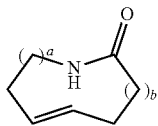

Formula (V)

wherein: a is 1, 2, 3, 4, 5 or 6; and b is 4, 5, 6 or 7.

In another embodiment, the E-macrocyclic product is represented by the structure of Formula (V), wherein a is 2; and b is 4, 5, 6 or 7.

In another embodiment, the at least one E-macrocyclic product is represented by the structure of Formula (V), wherein a is 1; and b is 5, 6 or 7.

In another embodiment, the at least one E-macrocyclic product is represented by the structure of Formula (V), wherein a is 3; and b is 5 or 7.

In another embodiment, the at least one E-macrocyclic product is represented by the structure of Formula (V), wherein a is 4; and b is 4.

In another embodiment, the at least one E-macrocyclic product is represented by the structure of Formula (V), wherein a is 5; and b is 5 or 7.

In one embodiment, the E-macrocyclic product has a carbon-carbon double bond in E-configuration and is represented by the structure of Formula (VII):

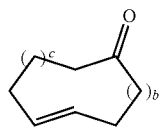

Formula (VII)

wherein: c is 1, 2, 3, 4, 5 or 6; and d is 4, 5, 6 or 7.

In another embodiment, the E-macrocyclic product is represented by the structure of Formula (VII), wherein c is 2; and d is 4, 5, 6 or 7.

In another embodiment, the at least one E-macrocyclic product is represented by the structure of Formula (VII), wherein c is 1; and d is 5, 6 or 7.

In another embodiment, the at least one E-macrocyclic product is represented by the structure of Formula (VII), wherein c is 3; and d is 4, 6 or 7.

In another embodiment, the at least one E-macrocyclic product is represented by the structure of Formula (VII), wherein c is 4; and d is 2, 5, 6 or 7.

In another embodiment, the at least one E-macrocyclic product is represented by the structure of Formula (VII), wherein c is 5; and d is 5 or 7.

In another embodiment, the at least one E-macrocyclic product is represented by the structure of Formula (VII), wherein c is 6; and d is 6.

Diene Substrates Bearing E-Olefin Moieties

In one embodiment, the diene starting material is bearing two E-olefins, or is bearing one E-olefin and a terminal olefin, and is represented by the structure of Formula (II), wherein:

n is 1, 2, 3, 4, 5 or 6;
m is 4, 5, 6 or 7;
R is H, linear or branched $C_{1-12}$ alkyl;
$R'^2$ is H or linear $C_{1-3}$ alkyl; and
$R'^1$ is H, linear or branched $C_{1-12}$ alkyl; with the proviso that only one of R and $R'^1$ can be H.

In one embodiment, the diene starting material is represented by Formula (II), wherein R is H, linear or branched $C_{1-6}$ alkyl; $R'^1$ is H, linear or branched $C_{1-6}$ alkyl; $R'^2$ is H or Me; n is 1, 2, 3, 4, 5 or 6; m is 4, 5, 6 or 7; with the proviso that only one of R and $R'^1$ can be H.

In one embodiment, the diene starting material is represented by Formula (II), wherein R is H, Me, Et, n-Pr or n-Bu; $R'^1$ is H, Me, Et, n-Pr or n-Bu; $R'^2$ is H or Me; n is 1, 2, 3, 4, 5 or 6; and m is 4, 5, 6 or 7; with the proviso that only one of R and $R'^1$ can be H.

In one embodiment, the diene starting material is represented by Formula (II), wherein R is Me; $R'^1$ is Me; $R'^2$ is H or Me; n is 1; and m is 5, 6 or 7.

In one embodiment, the diene starting material is represented by Formula (II), wherein R is Me; $R'^1$ is Me; $R'^2$ is H; n is 1; and m is 5, 6 or 7.

In one embodiment, the diene starting material is represented by Formula (II), wherein R is Me; $R'^1$ is Me; $R'^2$ is Me; n is 1; and m is 5.

In one embodiment, the diene starting material is represented by Formula (II), wherein R is Me; $R'^1$ is Me; $R'^2$ is H; n is 2; and m is 4, 6 or 7.

In one embodiment, the diene starting material is represented by Formula (II), wherein R is Me; $R'^1$ is H; $R'^2$ is H; n is 3; and m is 7.

In one embodiment, the diene starting material is represented by Formula (II), wherein R is Me; $R'^1$ is Me; $R'^2$ is H; n is 5; and m is 7.

In one embodiment, the diene starting material is represented by Formula (II), wherein R is Et; $R'^1$ is H; $R'^2$ is H; n is 1; and m is 7.

In another embodiment, diene starting material is bearing two E-olefins, or is bearing one E-olefin and a terminal olefin, and is represented by the structure of Formula (VI):

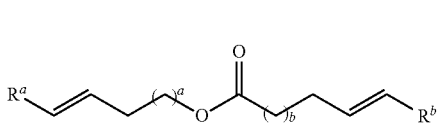

Formula (VI)

wherein: a is 1, 2, 3, 4, 5 or 6;
b is 4, 5, 6 or 7;
$R^a$ is H, linear or branched $C_{1-12}$ alkyl; and
$R^b$ is H, linear or branched $C_{1-12}$ alkyl; with the proviso that only one of $R^a$ and $R^b$ can be H.

In one embodiment, the diene starting material is represented by Formula (VI), wherein $R^a$ is H, linear or branched $C_{1-6}$ alkyl; $R^b$ is H, linear or branched $C_{1-6}$ alkyl; a is 1, 2, 3, 4, 5 or 6; and b is 4, 5, 6 or 7; with the proviso that only one of $R^a$ and $R^b$ can be H.

In one embodiment, the diene starting material is represented by Formula (VI), wherein $R^a$ is H, Me, Et, n-Pr or n-Bu; $R^b$ is H, Me, Et, n-Pr or n-Bu; a is 1, 2, 3, 4, 5 or 6; and b is 4, 5, 6 or 7; with the proviso that only one of $R^a$ and $R^b$ can be H.

In one embodiment, the diene starting material is represented by Formula (VI), wherein $R^a$ is Me; $R^b$ is H, Me, Et, or n-Pr; a is 1; and b is 4, 5, 6 or 7.

In one embodiment, the diene starting material is represented by Formula (VI), wherein $R^a$ is H; $R^b$ is H, Me, Et, n-Pr or n-Bu; a is 2; and b is 4, 5, 6 or 7.

In one embodiment, the diene starting material is represented by Formula (VI), wherein $R^a$ is Me or Et; $R^b$ is H, Me, Et; a is 3; and b is 4, 5, 6 or 7.

In one embodiment, the diene starting material is represented by Formula (VI), wherein $R^a$ is Me, Et, n-Pr or n-Bu; $R^b$ is H; a is 5; and b is 5 or 6.

In one embodiment, the diene starting material is represented by Formula (VI), wherein $R^a$ is Me; $R^b$ is Me; a is 1, 2, 3, 4, 5 or 6; and b is 4, 5, 6 or 7.

In one embodiment, the diene starting material is bearing two E-olefins, or is bearing one E-olefin and a terminal olefin, and is represented by Formula (VIII):

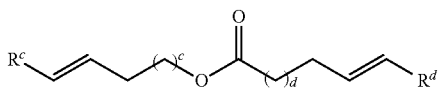

Formula (VIII)

wherein: c is 1, 2, 3, 4, 5 or 6;
d is 4, 5, 6 or 7;
$R^c$ is H, linear or branched $C_{1-12}$ alkyl; and
$R^d$ is H, linear or branched $C_{1-12}$ alkyl; with the proviso that only one of $R^c$ and $R^d$ can be H.

In one embodiment, the diene starting material is represented by Formula (VIII), wherein $R^c$ is H, linear or branched $C_{1-6}$ alkyl; $R^d$ is H, linear or branched $C_{1-6}$ alkyl; c is 1, 2, 3, 4, 5 or 6; d is 4, 5, 6 or 7; and only one of $R^c$ and $R^d$ can be H.

In one embodiment, the diene starting material is represented by Formula (VIII), wherein $R^c$ is H, Me, Et, n-Pr or n-Bu; $R^d$ is H, Me, Et, n-Pr or n-Bu; c is 1, 2, 3, 4, 5 or 6; and d is 4, 5, 6 or 7; and only one of $R^c$ and $R^d$ can be H.

In one embodiment, the diene starting material is represented by Formula (VIII), wherein $R^c$ is Me, Et, n-Pr or n-Bu; $R^d$ is H, Me, Et, n-Pr or n-Bu; c is 2; and d is 4, 5, 6 or 7.

In one embodiment, the diene starting material is represented by Formula (VIII), wherein $R^c$ is H, Me, Et, n-Pr or n-Bu; $R^d$ is Me, Et, n-Pr or n-Bu; c is 1; and d is 4, 5, 6 or 7.

In one embodiment, the diene starting material is represented by Formula (VIII), wherein $R^c$ is Me, Et, n-Pr or n-Bu; $R^d$ is Me, Et, n-Pr or n-Bu; c is 3; and d is 4, 5, 6 or 7.

In one embodiment, the diene starting material is represented by Formula (VIII), wherein $R^c$ is Me; $R^d$ is Me, Et, or n-Pr; c is 4; and d is 5 or 7.

In one embodiment, the diene starting material is represented by Formula (VII), wherein $R^c$ is Me; $R^d$ is Me; c is 1; and d is 6.

In one embodiment, the diene starting material is represented by Formula (VIII), wherein $R^c$ is Et; $R^d$ is H, Me, or Et; c is 1; and d is 7.

In one embodiment, the diene starting material is represented by Formula (VIII), wherein $R^c$ is H, Me, Et, or n-Pr, $R^d$ is Me; c is 2; and d is 6.

In one embodiment, the diene starting material is represented by Formula (VIII), wherein $R^c$ is Me; $R^d$ is Me; c is 1, 2, 3, 4, 5, or 6; and d is 4, 5, 6 or 7.

Olefin Metathesis Catalysts

In one embodiment, the invention provides a stereoretentive ruthenium olefin metathesis catalyst represented by the structure of Formula (I), wherein
X is O or S;
Y is O or S;
Z is N or $CR^{32}$;
W is O, halogen, $NR^{33}$ or S;
$R^1$ is H, optionally substituted $C_{1-24}$ alkyl, halogen, —C(O)$R^{25}$, —$OR^{26}$, CN, —$NR^{27}R^{28}$, $NO_2$, —$CF_3$, —$S(O)_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^2$ can form a spiro compound or together with $R^3$ or together with $R^4$ can form a polycyclic ring;
$R^2$ is H, optionally substituted $C_{1-24}$ alkyl, halogen, —C(O)$R^{25}$, —$OR^{26}$, CN, —$NR^{27}R^{28}$, $NO_2$, —$CF_3$, —$S(O)_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^1$ can form a spiro compound or together with $R^3$ or together with $R^4$ can form a polycyclic ring;
$R^3$ is H, optionally substituted $C_{1-24}$ alkyl, halogen, —C(O)$R^{25}$, —$OR^{26}$, CN, —$NR^{27}R^{28}$, $NO_2$, —$CF_3$, —$S(O)_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ or together with $R^1$ can form a polycyclic ring or together with $R^4$ can form a spiro compound;
$R^4$ is H, optionally substituted $C_{1-24}$ alkyl, halogen, —C(O)$R^{25}$, —$OR^{26}$, CN, —$NR^{27}R^{28}$, $NO_2$, —$CF_3$, —$S(O)_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^3$ can form a spiro compound or together with $R^2$ or together with $R^1$ can form a polycyclic ring;
$R^5$ is H, optionally substituted $C_{1-24}$ alkyl, halogen, —C(O)$R^{25}$, —$OR^{26}$, CN, —$NR^{27}R^{28}$, $NO_2$, —$CF_3$, —$S(O)_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^6$ can form an optionally substituted polycyclic ring;
$R^6$ is H, optionally substituted $C_{1-24}$ alkyl, halogen, —C(O)$R^{25}$, —$OR^{26}$, CN, —$NR^{27}R^{28}$, $NO_2$, —$CF_3$, —$S(O)_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^5$ or together with $R^7$ can form an optionally substituted polycyclic ring;

$R^7$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl optionally substituted $C_{3-8}$ cycloalkenyl, or together with $R^6$ or together with $R^8$ can form an optionally substituted polycyclic ring;

$R^8$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^7$ or together with $R^9$ can form an optionally substituted polycyclic ring;

$R^9$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^8$ can form an optionally substituted polycyclic ring;

$R^{10}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ can form an optionally substituted polycyclic ring;

$R^{11}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{10}$ or together with $R^{12}$ can form an optionally substituted polycyclic ring;

$R^{12}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ or together with $R^{13}$ can form an optionally substituted polycyclic ring;

$R^{13}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{14}$ or together with $R^{12}$ can form an optionally substituted polycyclic ring;

$R^{14}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{13}$ can form a polycyclic ring;

$R^{15}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ can form an optionally substituted polycyclic ring;

$R^{16}$ is H, optionally substituted $C_{1-4}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{15}$ or together with $R^{17}$ can form an optionally substituted polycyclic ring;

$R^{17}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ or together with $R^{16}$ can form an optionally substituted polycyclic ring;

$R^{18}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{17}$ can form an optionally substituted polycyclic ring;

$R^{19}$ is H, optionally substituted $C_{1-24}$ alkyl, —C(R$^{34}$)(R$^{35}$)COOR$^{36}$, —C(R$^{34}$)(R$^{35}$)C(O)H, —C(R$^{34}$)(R$^{35}$)C(O)R$^{37}$, —C(R$^{34}$)(R$^{35}$)CR$^{38}$(OR$^{39}$)(OR$^{40}$), —C(R$^{34}$)(R$^{35}$)C(O)NR$^{41}$R$^{42}$, —C(R$^{34}$)(R$^{35}$)C(O)NR$^{41}$OR$^{40}$, —C(O)R$^{25}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{33}$ can form an optionally substituted heterocyclic ring or is nil when W is halogen;

$R^{20}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ can form a polycyclic ring;

$R^{21}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{20}$ or together with $R^{22}$ can form a polycyclic ring;

$R^{22}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ or together with $R^{23}$ can form a polycyclic ring;

$R^{23}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{22}$ can form a polycyclic ring;

$R^{24}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, OR$^{30}$, NR$^{27}$R$^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is H, optionally substituted $C_{1-24}$ alkyl, $OR^{26}$, $-NR^{27}R^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{33}$ is H, optionally substituted $C_{1-24}$ alkyl, optionally substituted $C_{3-8}$ cycloalkyl, optionally substituted heterocycle, optionally substituted $C_{5-24}$ aryl, optionally substituted $C_{3-8}$ cycloalkenyl, or together with $R^{19}$ can form an optionally substituted heterocyclic ring;

$R^{34}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{35}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{36}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{37}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{38}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{39}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{40}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{41}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{42}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and x is 1 or 2.

When certain groups, such as: $C_{1-24}$ alkyl, $C_{3-8}$ cycloalkyl, heterocycle, $C_{5-24}$ aryl, $C_{3-8}$ cycloalkenyl groups or the polycyclic rings, are optionally substituted, the substituents are selected from: halogen, —OH, —SH, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, —CO—($C_1$-$C_{24}$ alkyl), —CO—($C_6$-$C_{24}$ aryl), —O—CO—($C_1$-$C_{24}$ alkyl), —O—CO—($C_6$-$C_{24}$ aryl), —(CO)—O—($C_1$-$C_{24}$ alkyl), —(CO)—O—($C_6$-$C_{24}$ aryl), (—O—(CO)—O—($C_1$-$C_{24}$ alkyl), —O—(CO)—O—($C_6$-$C_{24}$ aryl), (—COOH), (—(CO)—NH$_2$), (—(CO)—NH($C_1$-$C_{24}$ alkyl)), (—(CO)—N($C_1$-$C_{24}$ alkyl)$_2$), —(CO)—NH—($C_6$-$C_{24}$ aryl), (—(CO)—N($C_5$-$C_{24}$ aryl)$_2$), (—(CO)—N($C_1$-$C_{24}$ alkyl)($C_5$-$C_{24}$ aryl), (—(CS)—NH$_2$), (—(CS)—NH($C_1$-$C_{24}$ alkyl)), (—(CS)—N($C_1$-$C_{24}$ alkyl)$_2$), —(CS)—NH—($C_6$-$C_{24}$ aryl), (—(CS)—N($C_5$-$C_{24}$ aryl)$_2$), di-N—($C_1$-$C_{24}$ alkyl), (—(CS)—N($C_1$-$C_{24}$ alkyl)($C_5$-$C_{24}$ aryl), (—NH—(CO)—NH$_2$), (—C≡N), (—O—C≡N), (—S—C≡N), (—NCO), (—NCS), (—(CO)—H), (—(CS)—H), (—NH$_2$), (—NH ($C_1$-$C_{24}$ alkyl), ((—N($C_1$-$C_{24}$ alkyl)$_2$), (—NH($C_5$-$C_{24}$ aryl), (—N($C_5$-$C_{24}$ aryl)$_2$), —NH—(CO)—($C_1$-$C_6$ alkyl), —NH—(CO)—($C_6$-$C_{24}$ aryl), —C($C_1$-$C_{24}$ alkyl)(NH), (—CHN($C_1$-$C_{24}$ alkyl), (—CHN($C_6$-$C_{24}$ aryl), (—NO$_2$), (—NO), (—SO$_2$—OH), —S—($C_1$-$C_{24}$ alkyl), (—S—($C_5$-$C_{24}$ aryl), (—(SO)—($C_1$-$C_{24}$ alkyl), (—(SO)—($C_5$-$C_{24}$ aryl), SO$_2$—($C_1$-$C_{24}$ alkyl), (—SO$_2$—N(H)($C_1$-$C_{24}$ alkyl), (—SO$_2$—N($C_1$-$C_{24}$ alkyl)$_2$), (—SO$_2$—($C_5$-$C_{24}$ aryl), (—BH$_2$), B(OH)$_2$), (—B(O)($C_1$-$C_{24}$ alkyl)$_2$, (—P(O)(OH)$_2$), (—PO$_2$), (—PH$_2$), —SiH$_3$, (—O-silyl), $C_1$-$C_{24}$ alkyl, $C_1$-$C_{12}$ alkyl, $C_1$-$C_6$ alkyl, $C_2$-$C_{24}$ alkenyl, $C_2$-$C_{12}$ alkenyl, $C_2$-$C_6$ alkenyl, $C_2$-$C_{24}$ alkynyl, $C_2$-$C_{12}$ alkynyl, $C_2$-$C_6$ alkynyl, $C_5$-$C_{24}$ aryl, $C_5$-$C_{14}$ aryl, $C_6$-$C_{24}$ alkaryl, $C_6$-$C_{16}$ alkaryl, $C_6$-$C_{24}$ aralkyl, and $C_6$-$C_{16}$ aralkyl, which are as defined herein.

In another embodiment, the invention provides a catalyst represented by Formula (I) wherein: X is S; Y is S; Z is N or $CR^{32}$; W is O, $NR^{33}$ or S; $R^1$ is H, optionally substituted $C_{1-12}$ alkyl, halogen; $R^2$ is H, optionally substituted $C_{1-12}$ alkyl, halogen; $R^3$ is H, optionally substituted $C_{1-12}$ alkyl, halogen; $R^4$ is H, optionally substituted $C_{1-12}$ alkyl, halogen; $R^5$ is H, optionally substituted $C_{1-12}$ alkyl, halogen; $R^6$ is H, optionally substituted $C_{1-12}$ alkyl, halogen; $R^7$ is H, optionally substituted $C_{1-12}$ alkyl, halogen; $R^8$ is H, optionally substituted $C_{1-12}$ alkyl, halogen; $R^9$ is H, optionally substituted $C_{1-12}$ alkyl, halogen; $R^{10}$ is H, optionally substituted $C_{1-12}$ alkyl, halogen; $R^{11}$ is H, optionally substituted $C_{1-12}$ alkyl, halogen; $R^{12}$ is H, optionally substituted $C_{1-12}$ alkyl, halogen; $R^{13}$ is H, optionally substituted $C_{1-12}$ alkyl, halogen; $R^{14}$ is H, optionally substituted $C_{1-12}$ alkyl, halogen; $R^{15}$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl; $R^{16}$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl; $R^{17}$ is H, optionally substituted $C_{1-12}$ alkyl, halogen,—optionally substituted heterocycle, optionally substituted $C_{3-8}$ cycloalkyl, optionally substituted $C_{6-10}$ aryl or optionally substituted $C_{3-8}$ cycloalkenyl, or together with $R^{18}$ can form a polycyclic ring; $R^{18}$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl, or together with $R^{17}$ can form a polycyclic ring; $R^{19}$ is H, optionally substituted $C_{1-12}$ alkyl, —C($R^{34}$)($R^{35}$)—COO$R^{36}$, —C($R^{34}$)($R^{35}$)—C(O)H, —C($R^{34}$)($R^{35}$)—C(O)$R^{37}$, —C($R^{34}$)($R^{35}$)—C$R^{38}$(O$R^{39}$)(O$R^{40}$), —C($R^{34}$)($R^{35}$)—C(O)—N$R^{41}R^{42}$, —C($R^{34}$)($R^{35}$)—C(O)—N$R^{41}$O$R^{40}$, —C(O)$R^{25}$, optionally substituted heterocycle, optionally substituted $C_{3-8}$ cycloalkyl, optionally substituted $C_{6-10}$ aryl, optionally substituted $C_{3-8}$ cycloalkenyl, or together with $R^{33}$ can form an optionally substituted heterocyclic ring; $R^{20}$ is H, optionally substituted $C_{1-12}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{21}$ can form a polycyclic ring; $R^{21}$ is H, optionally substituted $C_{1-12}$ alkyl, halogen, —N$R^{27}R^{28}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{20}$ or together with $R^{22}$ can form a polycyclic ring; $R^{22}$ is H, optionally substituted $C_{1-12}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{21}$ or together with $R^{23}$ can form a polycyclic ring; $R^{23}$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl or together with $R^{22}$ can form a polycyclic ring; $R^{24}$ is H; $R^{25}$ is OH, O$R^{30}$, N$R^{27}R^{28}$, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{26}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{27}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{28}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{29}$ is H, optionally substituted $C_{1-12}$ alkyl, O$R^{26}$, —N$R^{27}R^{28}$, optionally substituted heterocycle, optionally substituted $C_{3-8}$ cycloalkyl, optionally substituted $C_{6-10}$ aryl or optionally substituted $C_{3-8}$ cycloalkenyl; $R^{30}$ is optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{31}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{32}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{33}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl, or together with $R^{19}$ can form an optionally substituted heterocyclic ring; $R^{34}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{35}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{36}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{37}$ is optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{38}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{39}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{40}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{41}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{42}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; and x is 1 or 2.

In another embodiment, the invention provides a catalyst represented by Formula (I) wherein: X is S; Y is S; Z is N or C$R^{32}$; W is O or N$R^{33}$; $R^1$ is H, linear or branched $C_{1-6}$ alkyl, or halogen; $R^2$ is H linear or branched $C_{1-6}$ alkyl, or halogen; $R^3$ is H, linear or branched $C_{1-6}$ alkyl, or halogen; $R^4$ is H, linear or branched $C_{1-6}$ alkyl or halogen; $R^5$ is H, linear or branched $C_{1-6}$ alkyl; $R^6$ is H, linear or branched $C_{1-6}$ alkyl; $R^7$ is H, linear or branched $C_{1-6}$ alkyl; $R^8$ is H or $C_{1-6}$ alkyl; $R^9$ is H, linear or branched $C_{1-6}$ alkyl; $R^{10}$ is H, linear or branched $C_{1-6}$ alkyl; $R^{11}$ is H, linear or branched $C_{1-6}$ alkyl; $R^{12}$ is H, linear or branched $C_{1-6}$ alkyl; $R^{13}$ is H, linear or branched $C_{1-6}$ alkyl or together with $R^{14}$ forms a naphthyl ring; $R^{14}$ is H, linear or branched $C_{1-6}$ alkyl or together with $R^{13}$ forms a naphthyl ring; $R^{15}$ is H, phenyl, linear or branched $C_{1-6}$ alkyl, halogen or together with $R^{16}$ forms a naphthyl ring; $R^{16}$ is H, phenyl, linear or branched $C_{1-6}$ alkyl, halogen or together with $R^{15}$ or together with $R^{17}$ forms a naphthyl ring; $R^{17}$ is H, phenyl, linear or branched $C_{1-6}$ alkyl, halogen or together with $R^{16}$ or together with $R^{18}$ forms a naphthyl ring; $R^{18}$ is H, phenyl, linear or branched $C_{1-6}$ alkyl, halogen or together with $R^{16}$ or together with $R^{18}$ forms a naphthyl ring; $R^{19}$ is H, phenyl, $C_{1-6}$ alkyl, —C($R^{34}$)($R^{35}$) COO$R^{36}$, —C($R^{34}$)($R^{35}$) C(O)H, —C($R^{34}$)($R^{35}$) C(O)$R^{37}$, —C($R^{34}$)($R^{35}$) C$R^{38}$(O$R^{39}$)(O$R^{40}$), —C($R^{34}$)($R^{35}$) C(O) N$R^{41}R^{42}$, —C($R^{34}$)($R^{35}$) C(O) N$R^{41}$O$R^{40}$ or together with $R^{33}$ forms a five, six or seven membered heterocyclic ring; $R^{20}$ is H, linear or branched $C_{1-16}$ alkyl, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, pyridine, piperidine, imidazole, indolizine, indazole, optionally substituted $C_{3-8}$ cycloalkyl, phenyl, naphthalene, cyclohexene or together with $R^{21}$ can form a polycycle; $R^{21}$ is H, phenyl, —N$R^{27}R^{28}$, linear or branched $C_{1-6}$ alkyl, halogen or together with $R^{20}$ or together with $R^{22}$ can form a polycycle; $R^{22}$ is H, linear or branched $C_{1-6}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, pyridine, piperidine, imidazole, indolizine, indazole, optionally substituted $C_{3-8}$ cycloalkyl, phenyl, naphthalene, cyclohexene or together with $R^{21}$ or together with $R^{23}$ can form a polycycle; $R^{23}$ is H, phenyl, linear or branched $C_{1-6}$ alkyl or together with $R^{22}$ can form a polycycle; $R^{24}$ is H, linear or branched $C_{1-6}$ alkyl; $R^{25}$ is OH, $OR^{30}$, $NR^{27}R^{28}$, linear or branched $C_{1-6}$ alkyl; $R^{26}$ is H, linear or branched $C_{1-6}$ alkyl; $R^{27}$ is H, linear or branched $C_{1-6}$ alkyl; $R^{28}$ is H, linear or branched $C_{1-6}$ alkyl; $R^{29}$ is H, linear or branched $C_{1-6}$ alkyl, —$NR^{27}R^{28}$; $R^{30}$ is optionally substituted $C_{1-6}$ alkyl, optionally substituted $C_{3-8}$ cycloalkyl, optionally substituted heterocycle, optionally substituted phenyl or optionally substituted $C_{3-8}$ cycloalkenyl; $R^{31}$ is H, linear or branched $C_{1-6}$ alkyl; $R^{32}$ is H, linear or branched $C_{1-6}$ alkyl; $R^{33}$ is H, linear or branched $C_{1-6}$ alkyl, or together with $R^{19}$ forms a five, six or seven membered heterocyclic ring; $R^{34}$ is H, or linear or branched $C_{1-6}$ alkyl; $R^{35}$ is H, or linear or branched $C_{1-6}$ alkyl; $R^{36}$ is H, linear or branched $C_{1-6}$ alkyl; $R^{37}$ is linear or branched $C_{1-6}$ alkyl; $R^{38}$ is H or linear or branched $C_{1-6}$ alkyl; $R^{39}$ is H, linear or branched $C_{1-6}$ alkyl; $R^{40}$ is H, linear or branched $C_{1-6}$ alkyl; $R^{41}$ is H, linear or branched $C_{1-6}$ alkyl; $R^{42}$ is H, linear or branched $C_{1-6}$ alkyl; and x is 1 or 2.

In one embodiment, the invention provides a catalyst represented by Formula (I) wherein: X is S; Y is S; Z is N or $CR^{32}$; W is O, $NR^{33}$ or S; $R^1$ is Me, Et, i-Pr, n-Pr, n-Bu, t-Bu, s-Bu or H; $R^2$ is Me, Et, i-Pr, n-Pr, n-Bu, t-Bu, s-Bu or H; $R^3$ is H, Me, Et, i-Pr, n-Pr, n-Bu, t-Bu, or s-Bu; $R^4$ is H, Me, Et, i-Pr, n-Pr, n-Bu, t-Bu, or s-Bu; $R^5$ is H, F, Cl, Br, I, Me, Et, i-Pr, n-Pr, n-Bu, t-Bu, or s-Bu; $R^6$ is H, F, Cl, Br, I, Me, Et, i-Pr, n-Pr, n-Bu, t-Bu, or s-Bu; $R^7$ is H, F, Cl, Br, I, Me, Et, i-Pr, n-Pr, n-Bu, t-Bu, or s-Bu; $R^8$ is H, F, Cl, Br, I, Me, Et, i-Pr, n-Pr, n-Bu, t-Bu, or s-Bu; $R^9$ is H, F, Cl, Br, I, Me, Et, i-Pr, n-Pr, n-Bu, t-Bu, or s-Bu; $R^{10}$ is H, F, Cl, Br, I, Me, Et, i-Pr, n-Pr, n-Bu, t-Bu, or s-Bu; $R^{11}$ is H, Me, F, Cl, Br, I, Et, i-Pr, n-Pr, n-Bu, t-Bu, or s-Bu; $R^{12}$ is H, F, Cl, Br, I, Me, Et, i-Pr, n-Pr, n-Bu, t-Bu, or s-Bu; $R^{13}$ is H, Me, F, Cl, Br, I, Et, n-Pr, i-Pr, n-Bu, t-Bu or s-Bu; $R^{14}$ is F, Cl, Br, I, Me, Et, i-Pr, n-Pr, n-Bu, t-Bu, s-Bu or H; $R^{15}$ is H, Me, Et, i-Pr, n-Pr, n-Bu, t-Bu, s-Bu, F, Br, I, Cl, or together with $R^{16}$ forms a naphthyl or a phenanthryl ring; $R^{16}$ is H, F, Cl, Br, I, or together with $R^{15}$ forms a naphthyl or a phenanthryl ring; $R^{17}$ is H, F, Cl, Br, I, or together with $R^{18}$ forms a naphthyl, or a phenanthryl ring; $R^{18}$ is H, Cl, F, Br, I, 3,5-dichloro-phenyl, phenyl, Me, Et, i-Pr, n-Pr, n-Bu, t-Bu, s-Bu or together with $R^{17}$ forms a naphthyl, or a phenanthryl; $R^{19}$ is H, phenyl, $C_{1-6}$ alkyl, —$C(R^{34})(R^{35})$ $COOR^{36}$, —$C(R^{34})(R^{35})$ $C(O)H$, —$C(R^{34})(R^{35})$ $C(O)R^{37}$, —$C(R^{34})(R^{35})$ $CR^{38}(OR^{39})(OR^{40})$, —$C(R^{34})(R^{35})$ $C(O)NR^{41}R^{42}$, —$C(R^{34})(R^{35})$ $C(O)$ $NR^{41}OR^{40}$; $R^{20}$ is H, F, Cl, Br, I, Me, Et, i-Pr, n-Pr, n-Bu, t-Bu, s-Bu, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, pyridine, piperidine, imidazole, indolizine, indazole, optionally substituted $C_{3-8}$ cycloalkyl, phenyl, naphthalene, or cyclohexene; $R^{21}$ is H, phenyl, Me, Et, i-Pr, n-Pr, n-Bu, t-Bu, s-Bu, —$NR^{27}R^{28}$ F, Cl, Br, or I; $R^{22}$ is H, Me, Et, i-Pr, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, pyridine, piperidine, imidazole, indolizine, indazole, cyclohexyl, phenyl, naphthalene, cyclohexene F, Cl, Br, or I; $R^{22}$ is H, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, or —$SR^{31}$; $R^{23}$ is H, F, Cl, Br, I, phenyl, Me, Et, i-Pr, n-Pr, n-Bu, t-Bu, or s-Bu; $R^{24}$ is H; $R^{24}$ is H, or Me; $R^{25}$ is OH, $OR^{30}$, $NR^{27}R^{28}$, Me, Et, or i-Pr; $R^{26}$ is H, Me, Et, i-Pr, n-Pr, n-Bu, t-Bu, or s-Bu; $R^{27}$ is H, Me, Et, i-Pr, n-Pr, n-Bu, t-Bu, or s-Bu; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, or —$NR^{27}R^{28}$; $R^{30}$ is Me, Et, i-Pr, n-Pr, n-Bu, t-Bu, or s-Bu; $R^{31}$ is H, Me, Et, i-Pr, n-Pr, n-Bu, t-Bu, or s-Bu; $R^{32}$ is Me, Et, n-Pr or H; $R^{33}$ is H, Me, Et, Me, Et, i-Pr, n-Pr, n-Bu, t-Bu, s-Bu, or together with $R^{19}$ forms a morpholino, a thio-morpholino, a pyrrolidino, a piperidino, or a piperazino ring; $R^{34}$ is H, Me, Et, i-Pr, n-Pr, n-Bu, t-Bu, or s-Bu; $R^{35}$ is H, or Me, Et, i-Pr, n-Pr, n-Bu, t-Bu, or s-Bu; $R^{36}$ is H, Me, Et, i-Pr, n-Pr, n-Bu, t-Bu, or s-Bu; $R^{37}$ is Me, Et, i-Pr, n-Pr, n-Bu, t-Bu, or s-Bu; $R^{38}$ is H or Me, Et, i-Pr, n-Pr, n-Bu, t-Bu, or s-Bu; $R^{39}$ is H, Me, Et, i-Pr, n-Pr, n-Bu, t-Bu, or s-Bu; $R^{40}$ is H, Me, Et, i-Pr, n-Pr, n-Bu, t-Bu, or s-Bu; $R^{41}$ is H, Me, Et, i-Pr, n-Pr, n-Bu, t-Bu, or s-Bu; $R^{42}$ is H, Me, Et, i-Pr, n-Pr, n-Bu, t-Bu, or s-Bu; and x is 1 or 2.

In one embodiment, the invention provides a catalyst represented by Formula (I) wherein: X is S; Y is S; Z is N; W is O; $R^1$ is Me or H; $R^2$ is Me or H; $R^3$ is H; $R^4$ is H; $R^5$ is H, F, Me, t-Bu or i-Pr; $R^6$ is H or t-Bu; $R^7$ is H, F or Me; $R^8$ is H, F or t-Bu; $R^9$ is H, F, Me, t-Bu or i-Pr; $R^{10}$ is H, F, Me, t-Bu or i-Pr; $R^{11}$ is H or t-Bu; $R^{12}$ is H, F or Me; $R^{13}$ is H, F or t-Bu; $R^{14}$ is F, Me, i-Pr, t-Bu or H; $R^{15}$ is H, Me, F, Br, I, Cl, or together with $R^{16}$ forms a naphthyl; $R^{16}$ is H, or together with $R^{15}$ forms a naphthyl; $R^{17}$ is H or together with $R^{18}$ forms a naphthyl, or a phenanthryl ring; $R^{18}$ is Cl, F, Br, I, 3,5-dichloro-phenyl, phenyl, t-Bu or together with $R^{17}$ forms a naphthyl, or a phenanthryl ring; $R^{19}$ is i-Pr, $R^{20}$ is H or phenyl; $R^{21}$ is H; $R^{22}$ is H, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$; $R^{23}$ is H; $R^{24}$ is H; $R^{25}$ is OH, $OR^{30}$, $NR^{27}R^{28}$, Me, Et, or i-Pr; $R^{26}$ is H, Me, Et, i-Pr, n-Pr, n-Bu, t-Bu, or s-Bu; $R^{27}$ is H, Me, Et, i-Pr, n-Pr, n-Bu, t-Bu, or s-Bu; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, —$NR^{27}R^{28}$; $R^{30}$ is Me, Et, i-Pr, n-Pr, n-Bu, t-Bu, or s-Bu; and $R^{31}$ is H, Me, Et, i-Pr, n-Pr, n-Bu, t-Bu, or s-Bu.

In one embodiment, the invention provides a catalyst represented by Formula (I) wherein: X is S; Y is S; Z is N; W is O; $R^1$ is Me; $R^2$ is Me; $R^3$ is H; $R^4$ is H; $R^5$ is F; $R^6$ is H; $R^7$ is H or F; $R^8$ is H; $R^9$ is F; $R^{10}$ is F; $R^{11}$ is H; $R^{12}$ is H; $R^{13}$ is H; $R^{14}$ is F; $R^{15}$ is Cl; $R^{16}$ is H; $R^{17}$ is H; $R^{18}$ is Cl; $R^{19}$ is i-Pr, $R^{20}$ is phenyl; $R^{21}$ is H; $R^{22}$ is H; $R^{23}$ is H; and $R^{24}$ is H.

In one embodiment, the invention provides a catalyst represented by Formula (I) wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a compound wherein the moiety

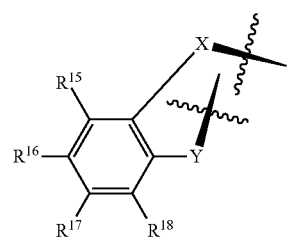

of Formula (I) is
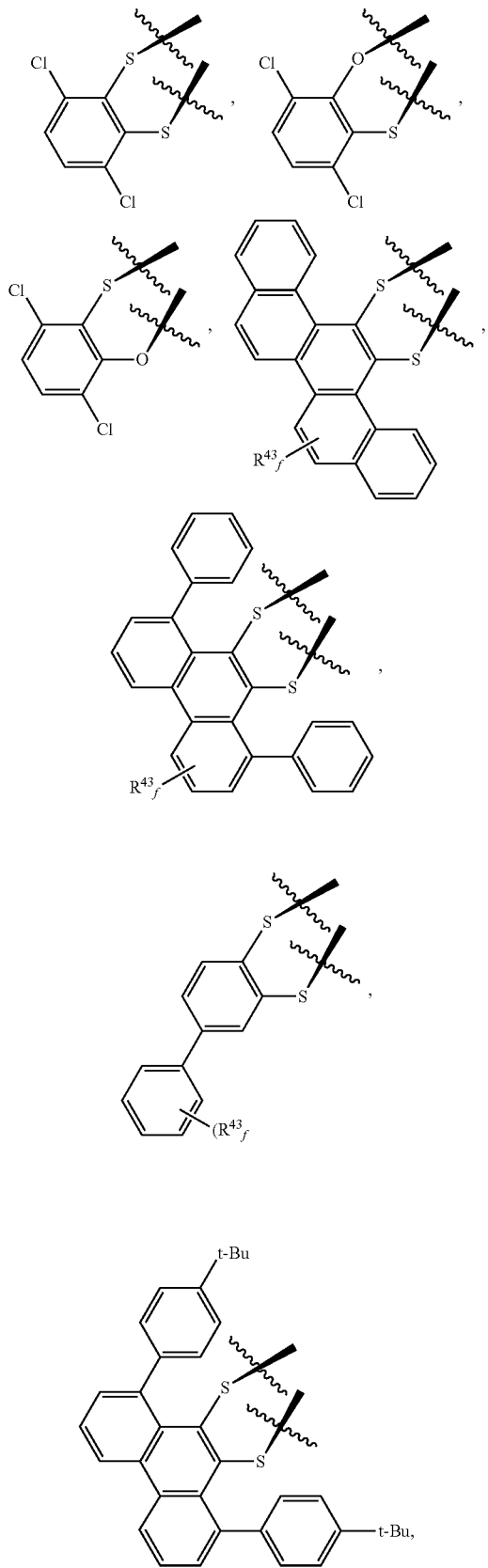
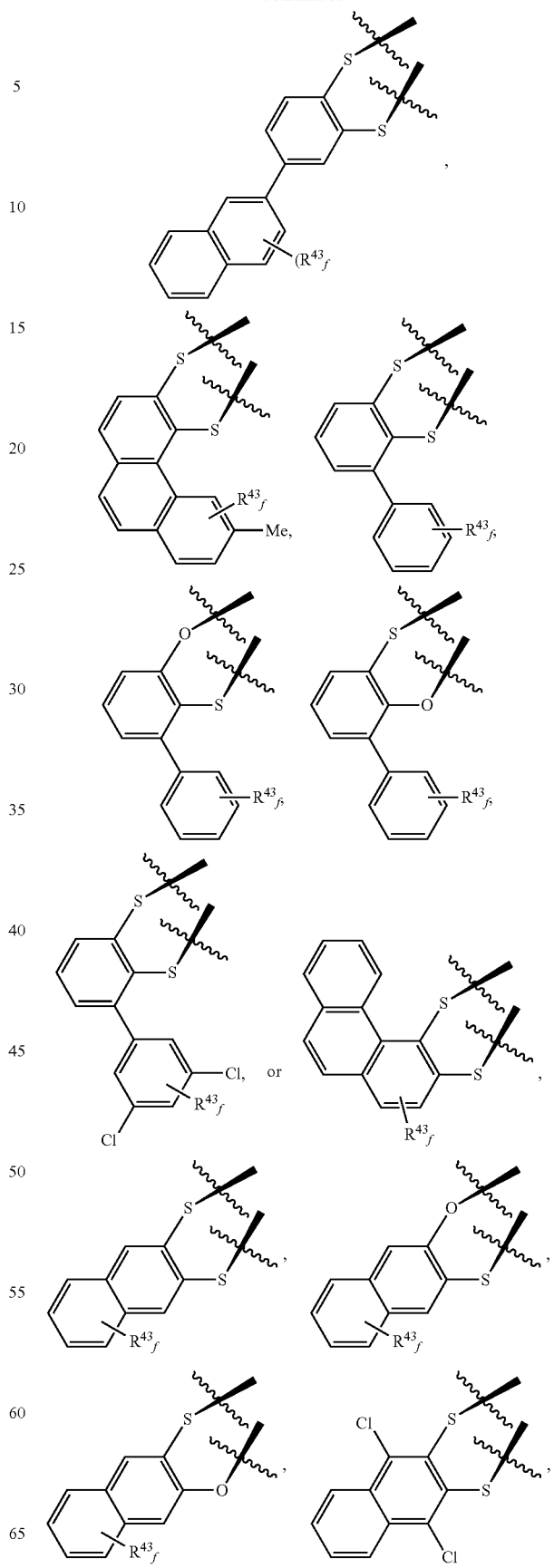

-continued

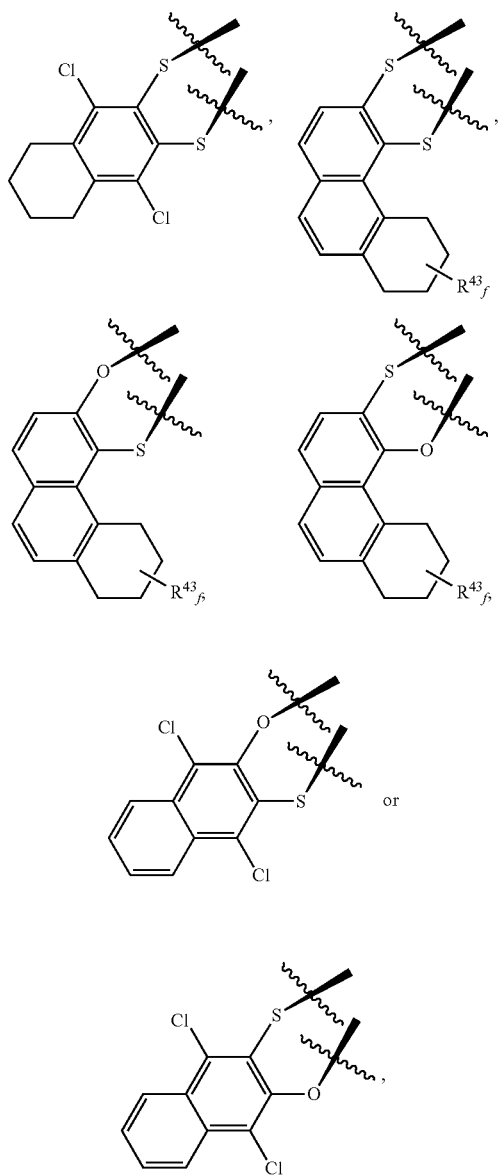

Wherein, $R^{43}$ is optionally substituted $C_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, and "f" is 0, 1, 2, 3, or 4.

In one embodiment, the invention provides a compound wherein the moiety of Formula (I) is

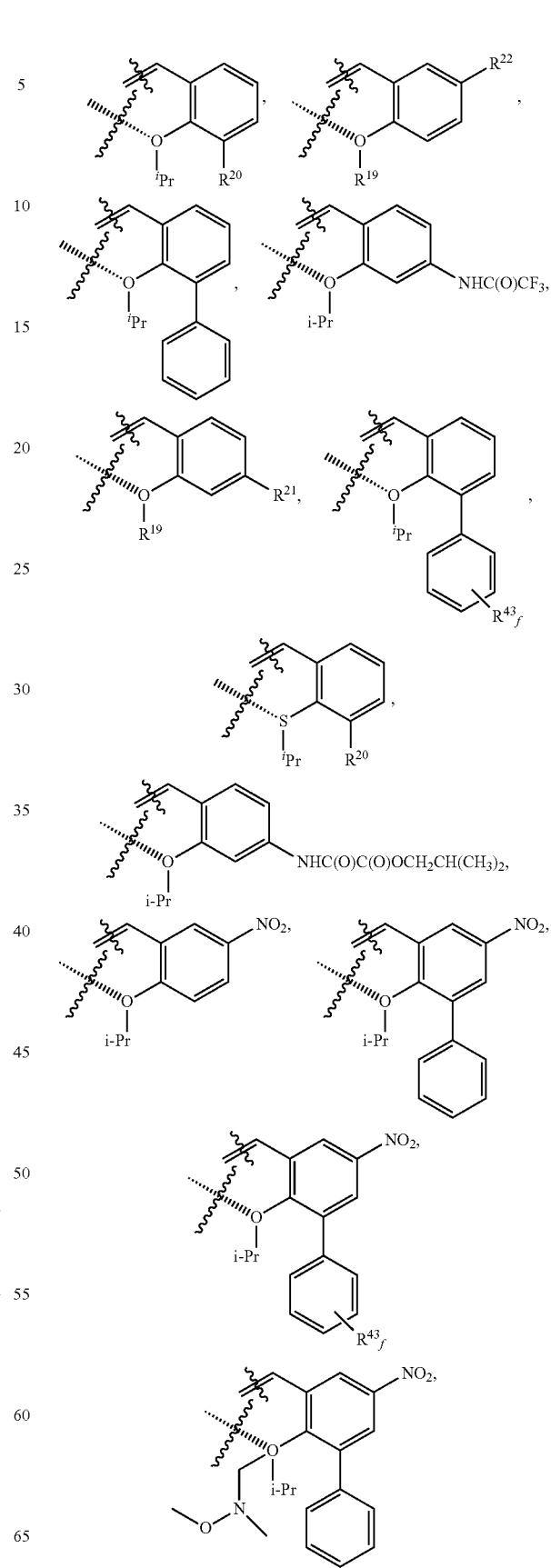

35
-continued
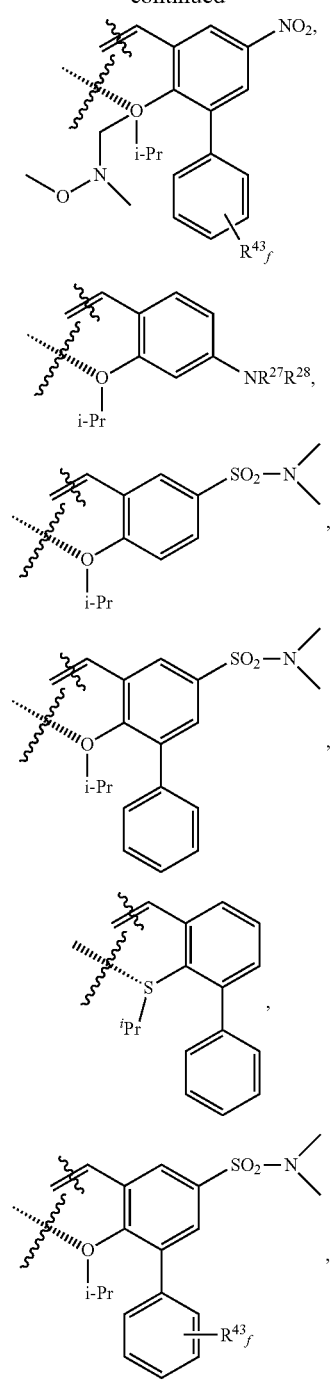
36
-continued
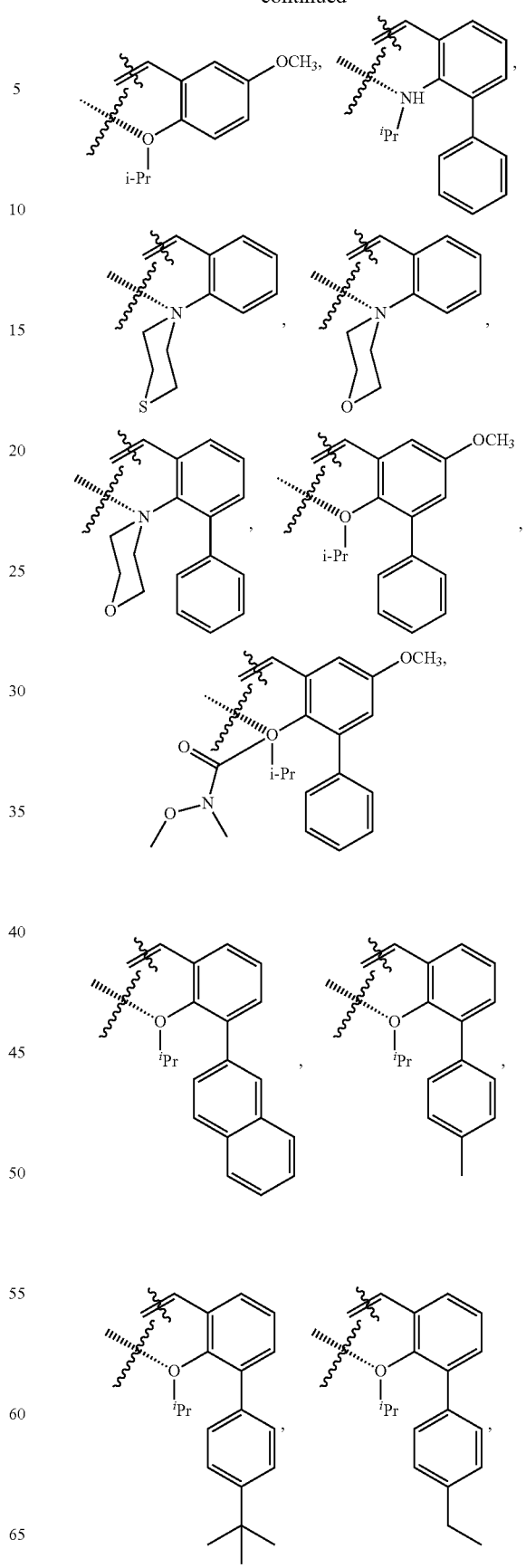

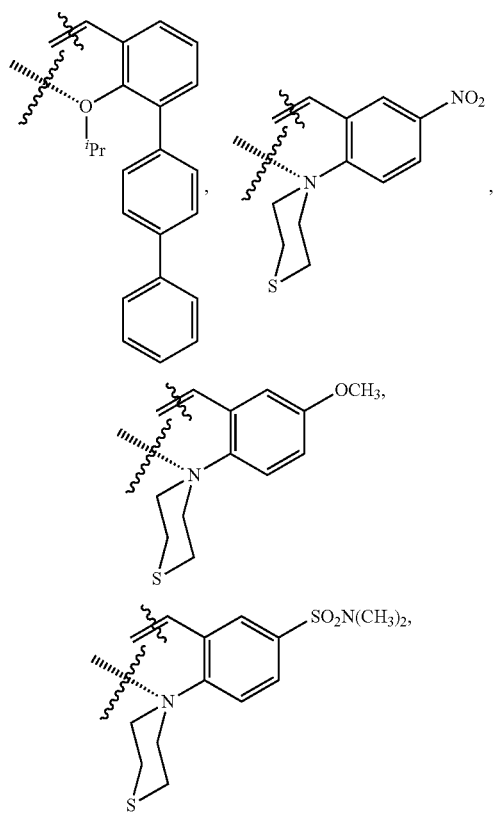
In one embodiment, the invention provides a compound wherein the moiety
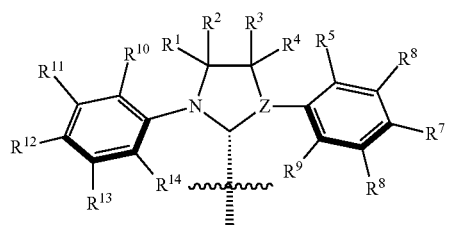
of Formula (I) is
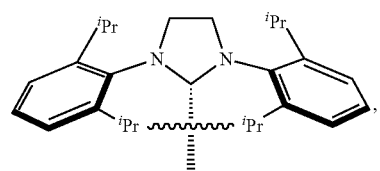
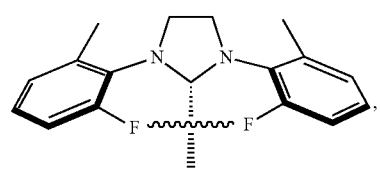
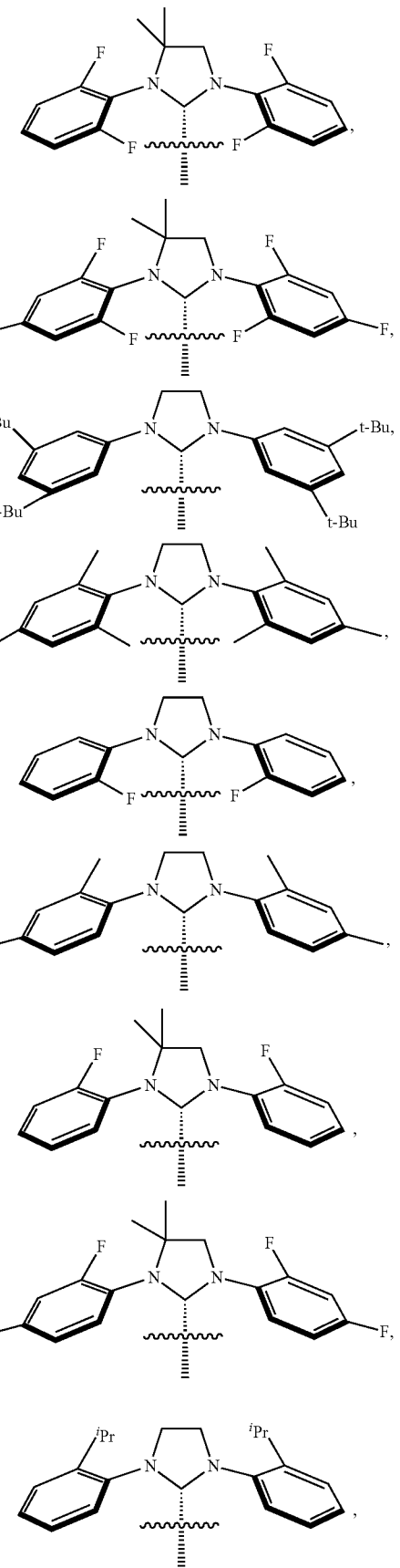

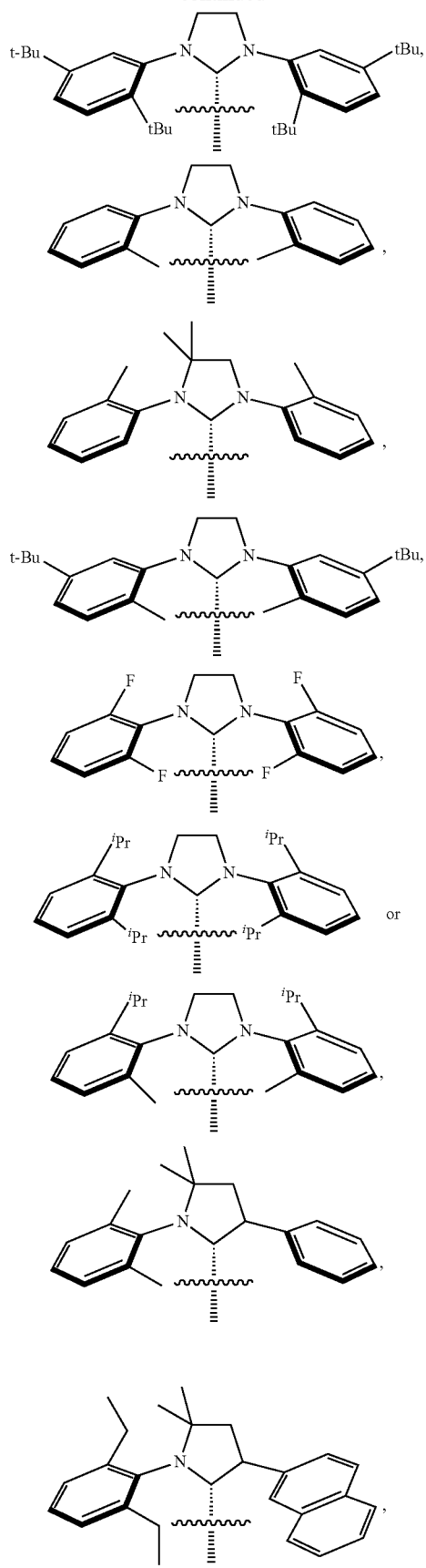
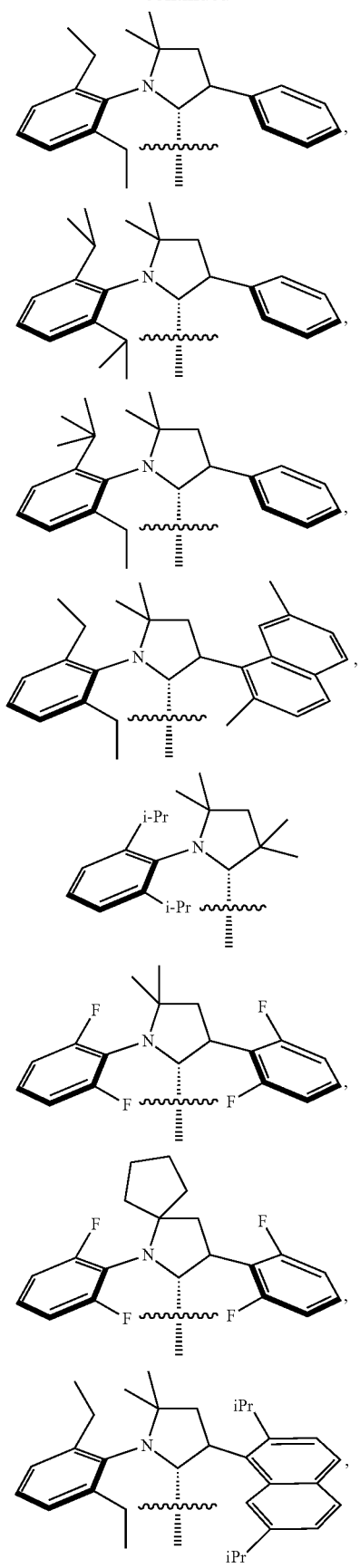

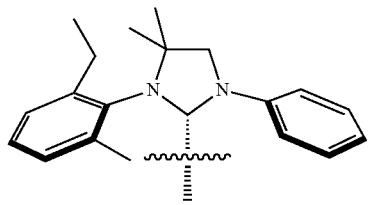
In one embodiment, the invention provides a compound of Formula (I) is selected from:
C813
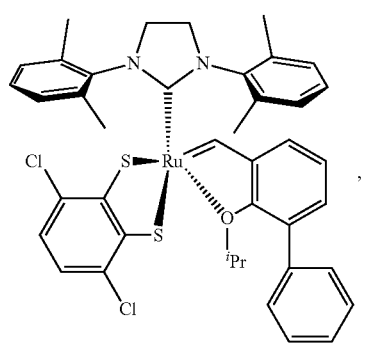
,
C857
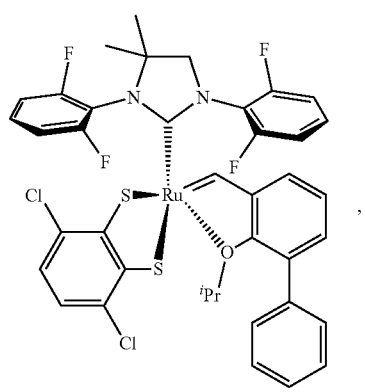
,
C894
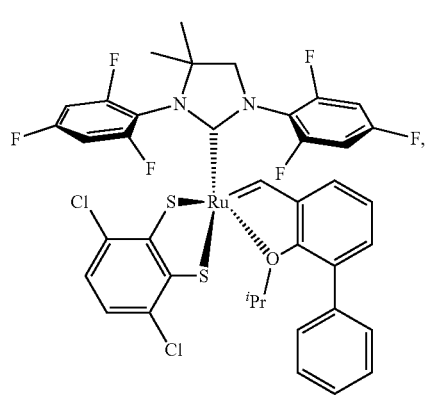
C981
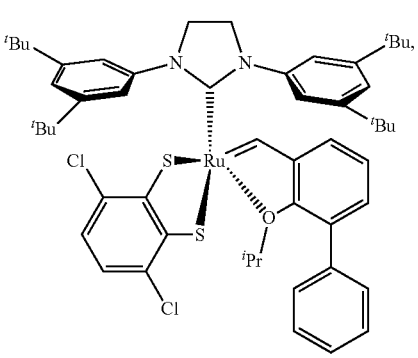
C849
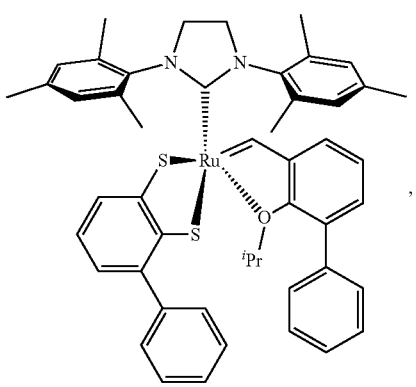
,
C823
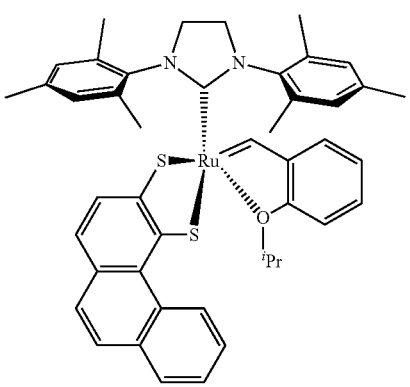
,
C797

C813
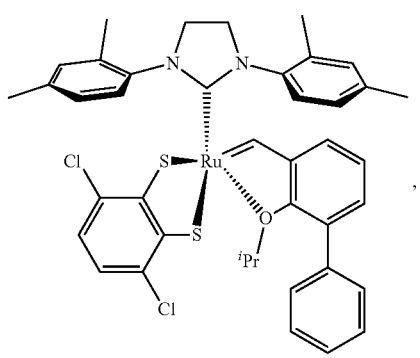
C793
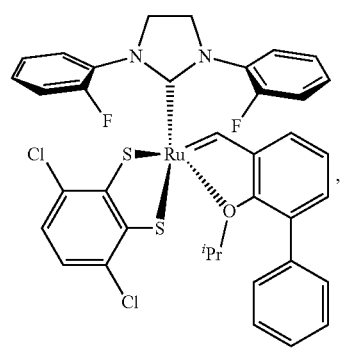
C821
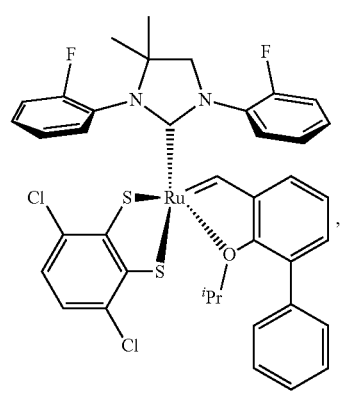
C782
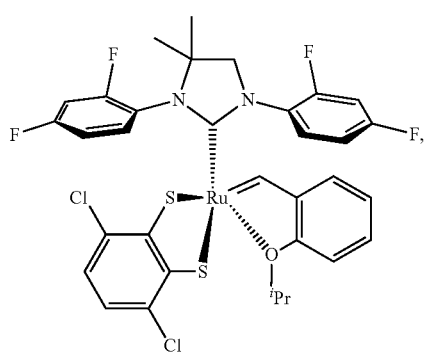
C841
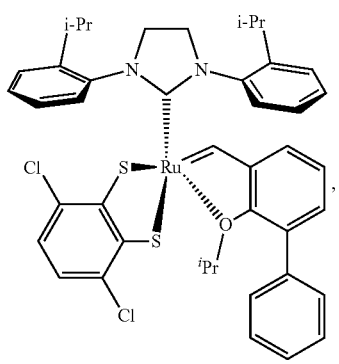
C982
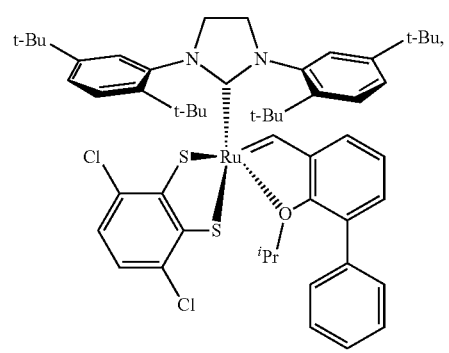
C785
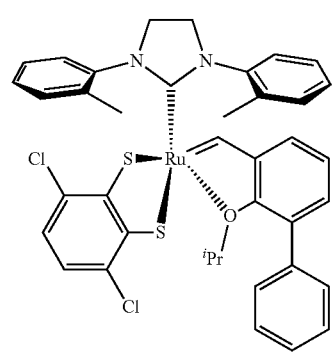
C814
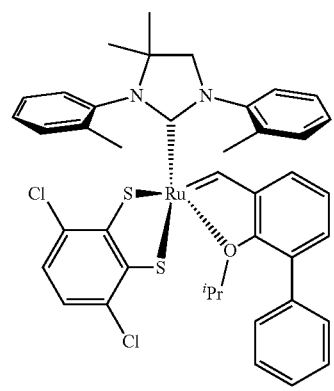

C814
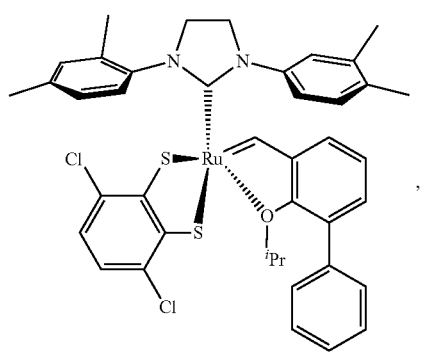
C786
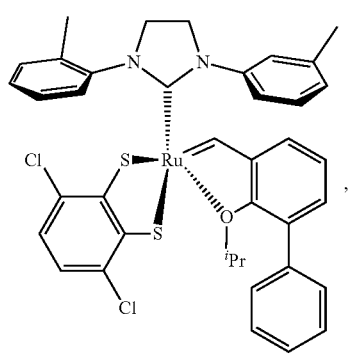
C842
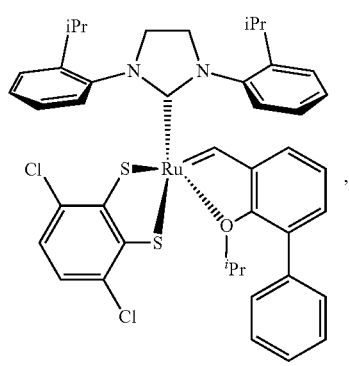
C753
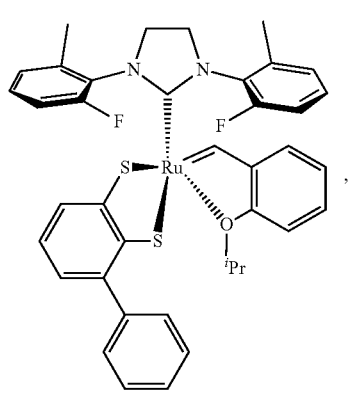
C727
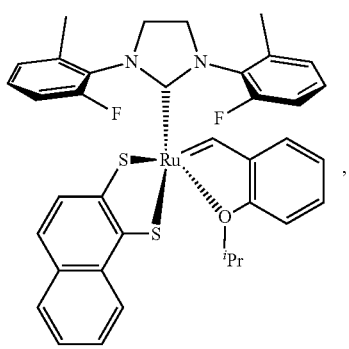
C821
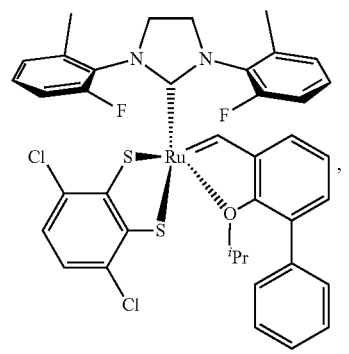
C864
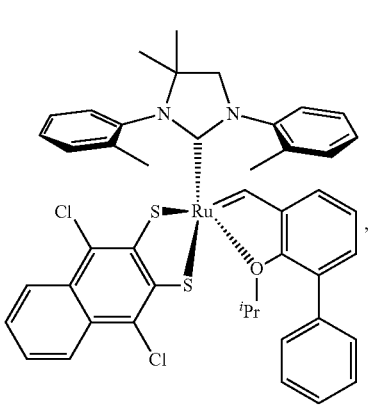
C777
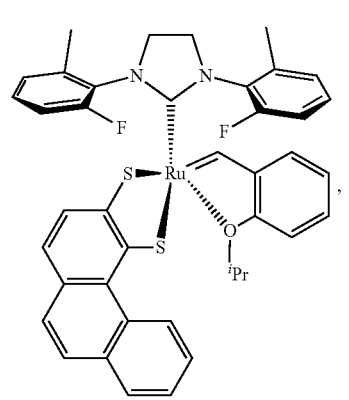

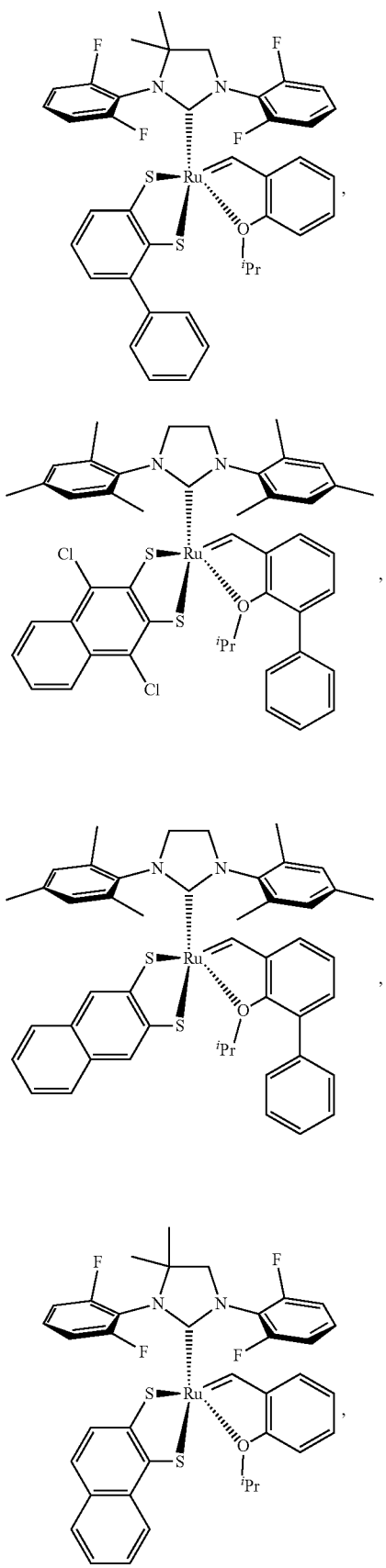
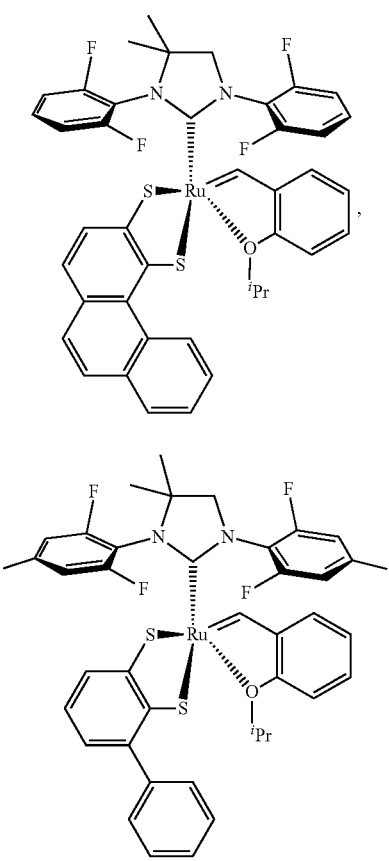

-continued
C912
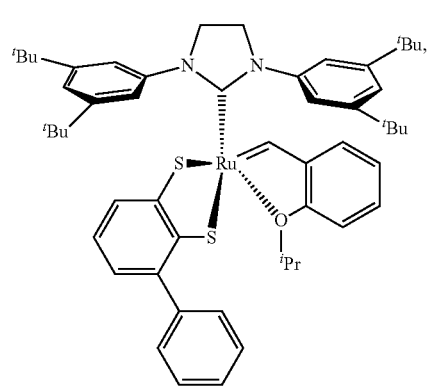
C886
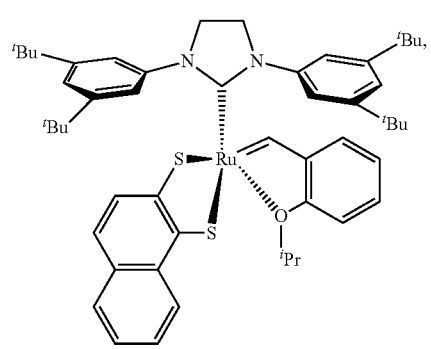
C936
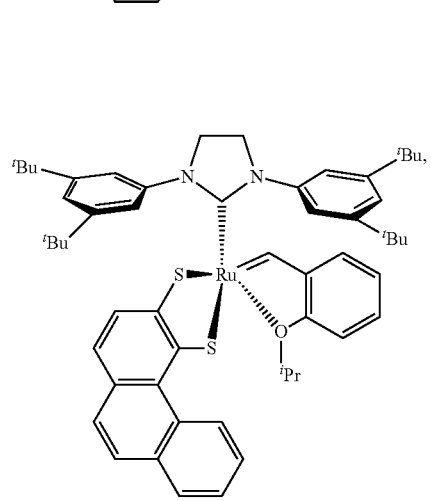
C857
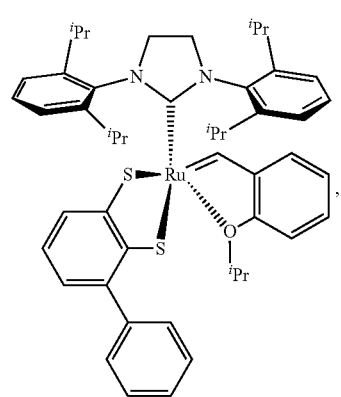
-continued
C831c
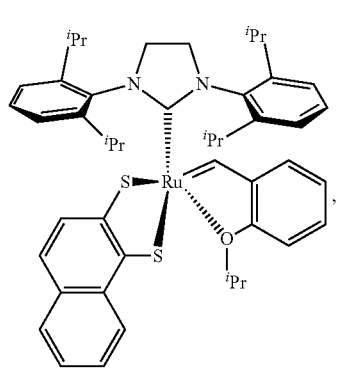
C881
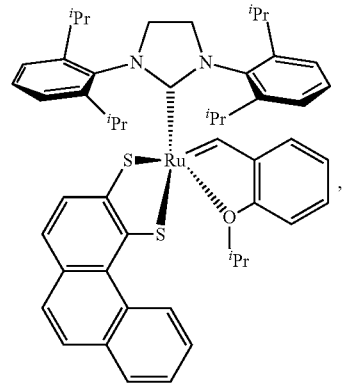
C789
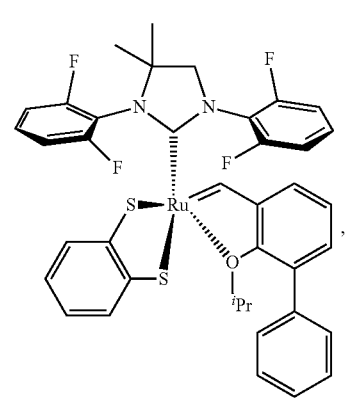
C820
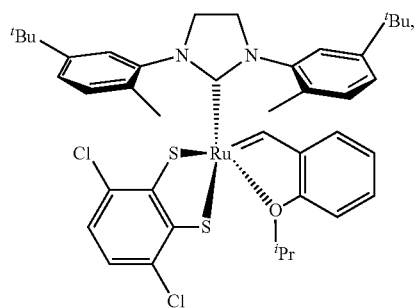

-continued
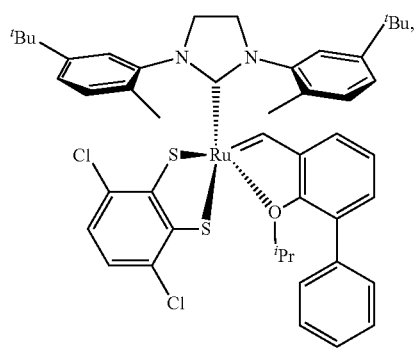
C896z
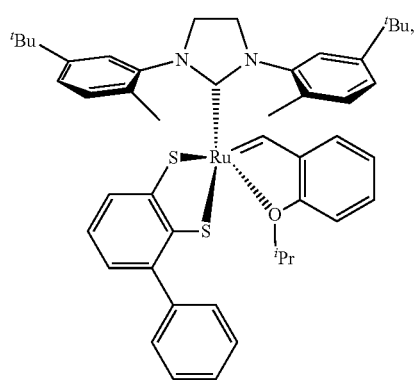
C827z
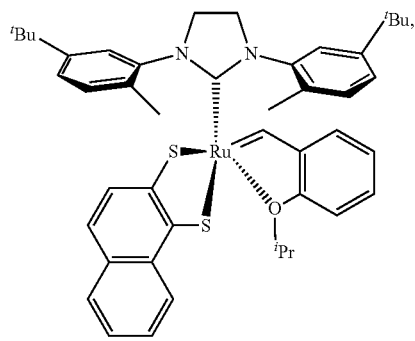
C801z
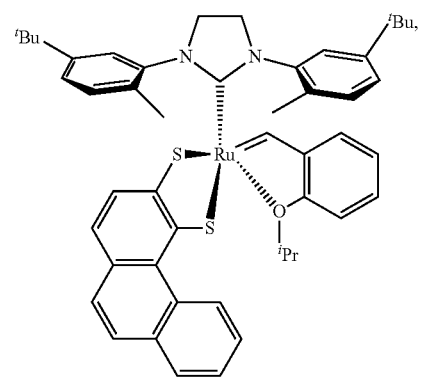
C853
-continued
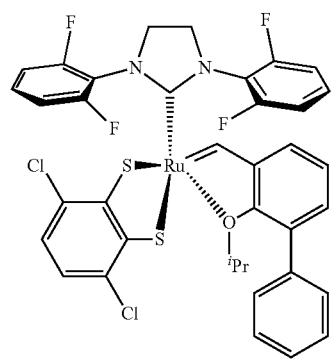
C830
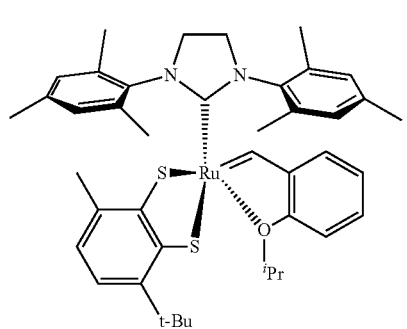
C767
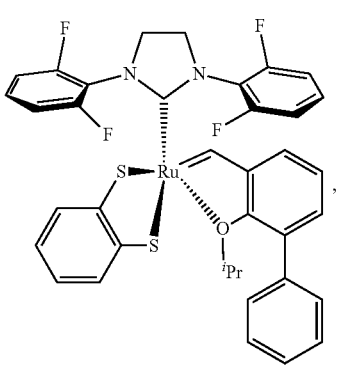
C761
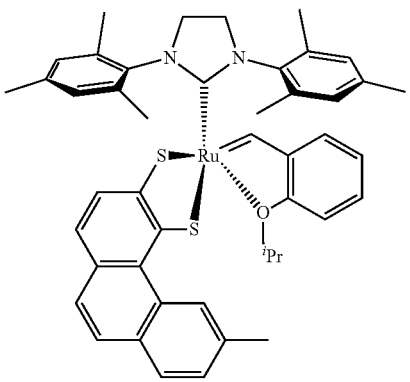
C811

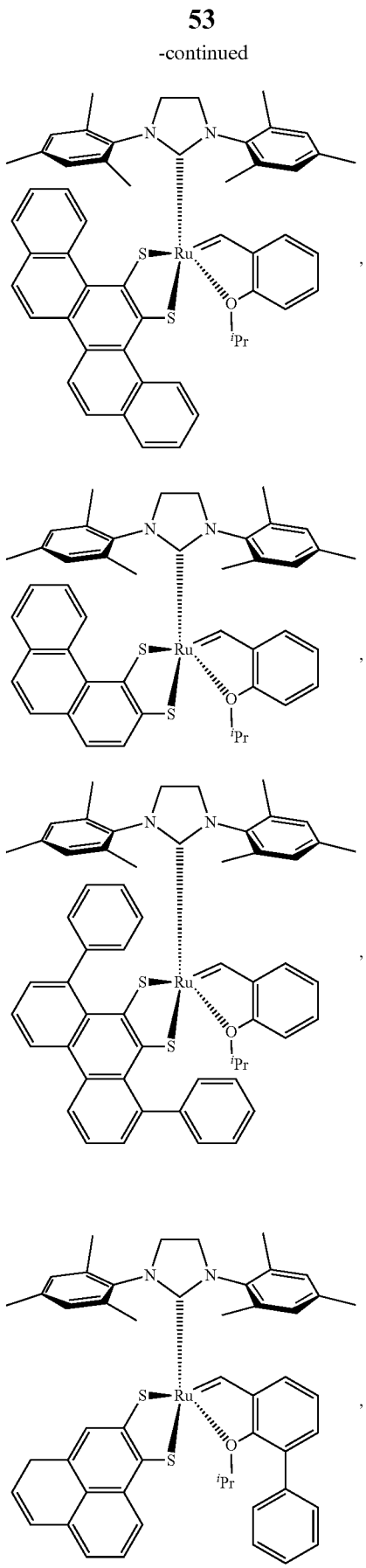

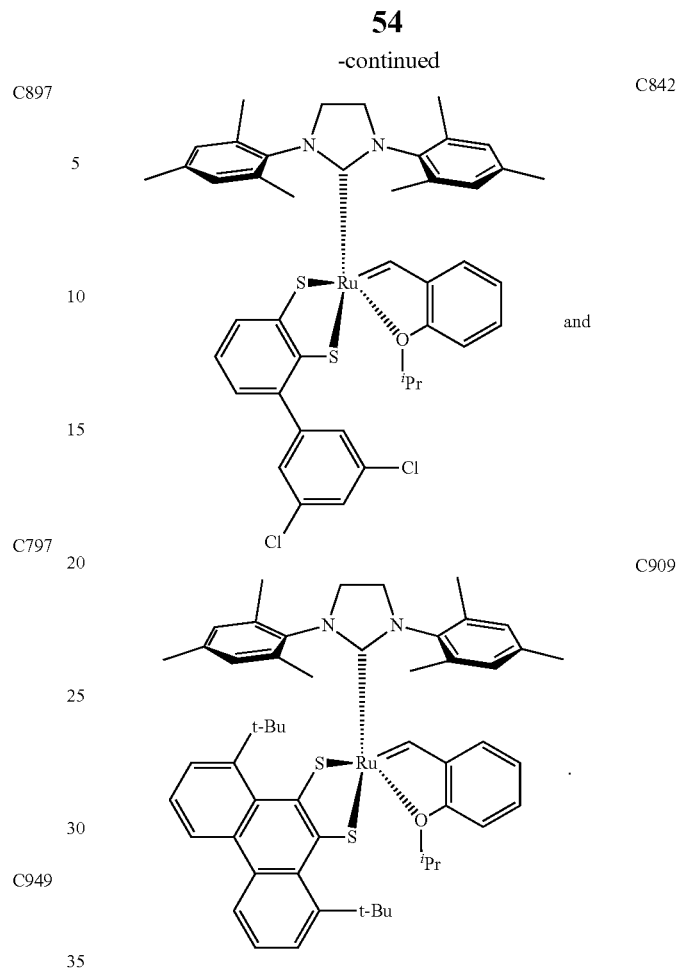

It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of an olefinic substrate.

The catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

When expressed as the molar ratio of olefin to catalyst, the catalyst (the "olefin to catalyst ratio"), loading will generally be present in an amount that ranges from a low of about 10,000,000:1, 1,000,000:1, 500,000:1 or 200,00:1, to a high of about 100,000:160,000:1, 50,000:1, 45.000:1, 40,000:1, 30,000:1, 20,000:1, 10,000:1, 5,000:1, or 1,000:1.

EMBODIMENTS

In one embodiment, the invention provides a method for producing one E-macrocyclic product represented by Formula (III), wherein: $R^{r2}$ is H or linear $C_{1-3}$ alkyl; n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and a terminal olefin, represented by Formula (II), wherein: n is 1, 2, 3, 4, 5 or 6; m is 4, 5, 6 or 7; R is H, linear or branched $C_{1-12}$ alkyl; $R^{r1}$ is H, linear or branched $C_{1-12}$ alkyl; $R^{r2}$ is H or linear $C_{1-3}$ alkyl; and with the proviso that only one of R and $R^{r1}$ can be H; to a macrocyclic ring-closing metathesis reaction in the presence of a stereoretentive ruthenium olefin metathesis catalyst represented by Formula (I), wherein X is O or S; Y is O or S; Z is N or $CR^{32}$; W is O, halogen, $NR^{33}$ or S; $R^1$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^2$ can form a spiro compound or together with $R^3$ or together with $R^4$ can form a polycyclic ring; $R^2$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^1$ can form a spiro compound or together with $R^3$ or together with $R^4$ can form a polycyclic ring; $R^3$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ or together with $R^1$ can form a polycyclic ring or together with $R^4$ can form a spiro compound; $R^4$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^3$ can form a spiro compound or together with $R^2$ or together with $R^1$ can form a polycyclic ring; $R^5$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^6$ can form an optionally substituted polycyclic ring; $R^6$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^5$ or together with $R^7$ can form an optionally substituted polycyclic ring; $R^7$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl optionally substituted $C_{3-8}$ cycloalkenyl, or together with $R^6$ or together with $R^8$ can form an optionally substituted polycyclic ring; $R^8$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^7$ or together with $R^9$ can form an optionally substituted polycyclic ring; $R^9$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^8$ can form an optionally substituted polycyclic ring; $R^{10}$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ can form an optionally substituted polycyclic ring; $R^{11}$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{10}$ or together with $R^{12}$ can form an optionally substituted polycyclic ring; $R^{12}$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ or together with $R^{13}$ can form an optionally substituted polycyclic ring; $R^{13}$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{14}$ or together with $R^{12}$ can form an optionally substituted polycyclic ring; $R^{14}$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{13}$ can form a polycyclic ring; $R^{15}$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ can form an optionally substituted polycyclic ring; $R^{16}$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{15}$ or together with $R^{17}$ can form an optionally substituted polycyclic ring; $R^{17}$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ or together with $R^{16}$ can form an optionally substituted polycyclic ring; $R^{18}$ is H, optionally substituted $C_{1-24}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{17}$ can form an optionally substituted polycyclic ring; $R^{19}$ is H, optionally substituted $C_{1-24}$ alkyl, $-C(R^{34})(R^{35})COOR^{36}$, $-C(R^{34})(R^{35})C(O)H$, $-C(R^{34})(R^{35})C(O)R^{37}$, $-C(R^{34})(R^{35})CR^{38}(OR^{39})(OR^{40})$, $-C(R^{34})(R^{35})C(O)NR^{41}R^{42}$, $-C(R^{34})(R^{35})C(O)NR^{41}OR^{40}$, $-C(O)R^{25}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{33}$ can form an optionally substituted heterocyclic ring or is nil when W is halogen; $R^{20}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ can form a polycyclic ring; $R^{21}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{20}$ or together with $R^{22}$ can form a polycyclic ring; $R^{22}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ or together with $R^{23}$ can form a polycyclic ring; $R^{23}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{22}$ can form a polycyclic ring; $R^{24}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl; $R^{25}$ is OH, $OR^{30}$, $NR^{27}R^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{29}$ is H, optionally substituted $C_{1-24}$ alkyl, $OR^{26}$, $-NR^{27}R^{28}$, optionally substituted heterocycle, optionally substituted $C_{3-8}$ cycloalkyl, optionally substituted $C_{5-24}$ aryl or optionally substituted $C_{3-8}$ cycloalkenyl; $R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{31}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{32}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{33}$ is H, optionally substituted $C_{1-24}$ alkyl, optionally substituted $C_{3-8}$ cycloalkyl, optionally substituted heterocycle, optionally substituted $C_{5-24}$ aryl, optionally substituted $C_{3-8}$ cycloalkenyl, or together with $R^{19}$ can form an optionally substituted heterocyclic ring; $R^{34}$ is H, optionally substituted $C_{1-12}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{35}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{36}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{37}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{38}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{39}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{40}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{41}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; $R^{42}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and x is 1 or 2.

In one embodiment, the invention provides a method for producing one E-macrocyclic product represented by Formula (III), wherein: $R'^2$ is H or linear $C_{1-3}$ alkyl; n is 1, 2, 3, 4, 5 or 6; m is 4, 5, 6, or 7; and wherein the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefin or bearing one E-olefin and one terminal olefin, represented by Formula (II), wherein: n is 1, 2, 3, 4, 5 or 6; m is 4, 5, 6 or 7; R is H, linear or branched $C_{1-12}$ alkyl; $R'^1$ is H, linear or branched $C_{1-12}$ alkyl; $R'^2$ is H or linear $C_{1-3}$ alkyl; and with the proviso that only one of R and $R'^1$ can be H; to a macrocyclic ring-closing metathesis reaction in the presence of a stereoretentive ruthenium olefin metathesis catalyst represented by Formula (I), wherein: X is S; Y is S; Z is N or $CR^{32}$; W is O, $NR^{33}$ or S; $R^1$ is H, optionally substituted $C_{1-12}$ alkyl, halogen; $R^2$ is H, optionally substituted $C_{1-12}$ alkyl, halogen; $R^3$ is H optionally substituted $C_{1-12}$ alkyl, halogen; $R^4$ is H, optionally substituted $C_{1-12}$ alkyl, halogen; $R^5$ is H, optionally substituted $C_{1-12}$ alkyl, halogen; $R^6$ is H, optionally substituted $C_{1-12}$ alkyl, halogen; $R^7$ is H, optionally substituted $C_{1-12}$ alkyl, halogen; $R^8$ is H, optionally substituted $C_{1-12}$ alkyl, halogen; $R^9$ is H, optionally substituted $C_{1-12}$ alkyl, halogen; $R^{10}$ is H, optionally substituted $C_{1-12}$ alkyl, halogen; $R^{11}$ is H, optionally substituted $C_{1-12}$ alkyl, halogen; $R^{12}$ is H, optionally substituted $C_{1-12}$ alkyl, halogen; $R^{13}$ is H, optionally substituted $C_{1-12}$ alkyl, halogen; $R^{14}$ is H, optionally substituted $C_{1-12}$ alkyl, halogen; $R^{15}$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl; $R^{16}$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl; $R^{17}$ is H, optionally substituted $C_{1-12}$ alkyl, halogen,—optionally substituted heterocycle, optionally substituted $C_{3-8}$ cycloalkyl, optionally substituted $C_{6-10}$ aryl or optionally substituted $C_{3-8}$ cycloalkenyl, or together with $R^{18}$ can form a polycyclic ring; $R^{18}$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl, or together with $R^{17}$ can form a polycyclic ring; $R^{19}$ is H, optionally substituted $C_{1-12}$ alkyl, $-C(R^{34})(R^{35})-COOR^{36}$, $-C(R^{34})(R^{35})-C(O)H$, $-C(R^{34})(R^{35})-C(O)R^{37}$, $-C(R^{34})(R^{35})-CR^{38}(OR^{39})(OR^{40})$, $-C(R^{34})(R^{35})-C(O)-NR^{41}R^{42}$, $-C(R^{34})(R^{35})-C(O)-NR^{41}OR^{40}$, $-C(O)R^{25}$, optionally substituted heterocycle, optionally substituted $C_{3-8}$ cycloalkyl, optionally substituted $C_{6-10}$ aryl, optionally substituted $C_{3-8}$ cycloalkenyl, or together with $R^{33}$ can form an optionally substituted heterocyclic ring; $R^{20}$ is H, optionally substituted $C_{1-12}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{21}$ can form a polycyclic ring; $R^{21}$ is H, optionally substituted $C_{1-12}$ alkyl, halogen, $-NR^{27}R^{28}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{20}$ or together with $R^{22}$ can form a polycyclic ring; $R^{22}$ is H, optionally substituted $C_{1-12}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{21}$ or together with $R^{23}$ can form a polycyclic ring; $R^{23}$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl or together with $R^{22}$ can form a polycyclic ring; $R^{24}$ is H; $R^{25}$ is OH, $OR^{30}$, $NR^{27}R^{28}$, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$cycloalkenyl; $R^{26}$ is H, optionally substituted $C_{1-12}$ alkyl, optionally substituted $C_{3-8}$cycloalkyl, optionally substituted heterocycle, optionally substituted $C_{6-12}$ aryl or optionally substituted $C_{3-8}$ cycloalkenyl; $R^{27}$ is H, optionally substituted $C_{1-12}$ alkyl, optionally substituted $C_{3-8}$ cycloalkyl, optionally substituted heterocycle, optionally substituted $C_{6-12}$ aryl or optionally substituted $C_{3-8}$ cycloalkenyl; $R^{28}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{29}$ is H, optionally substituted $C_{1-12}$ alkyl, $OR^{26}$, $-NR^{27}R^{28}$, optionally substituted heterocycle, optionally substituted $C_{3-8}$ cycloalkyl, optionally substituted $C_{6-10}$ aryl or optionally substituted $C_{3-8}$ cycloalkenyl; $R^{30}$ is optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{31}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{32}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{33}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl, or together with $R^{19}$ can form an optionally substituted heterocyclic ring; $R^{34}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{35}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{36}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{37}$ is optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{38}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{39}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{40}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{41}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{42}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; and x is 1 or 2.

In one embodiment, the invention provides a method for producing at least one E-macrocyclic product represented by Formula (III), wherein: $R'^2$ is H or linear $C_{1-3}$ alkyl n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (II), wherein: n is 1, 2, 3, 4, 5 or 6; m is 4, 5, 6 or 7; R is H, linear or branched $C_{1-12}$ alkyl; $R^{r1}$ is H, linear or branched $C_{1-12}$ alkyl; $R'^2$ is H or linear $C_{1-3}$ alkyl; and with the proviso that only one of R and $R^{r1}$ can be H; to a macrocyclic ring-closing metathesis reaction in the presence of a stereoretentive ruthenium olefin metathesis catalyst represented by Formula (I), wherein: X is S; Y is S; Z is N or $CR^{32}$; W is O, $NR^{33}$ or S; $R^1$ is Me, Et, i-Pr, n-Pr, n-Bu, t-Bu, s-Bu or H; $R^2$ is Me, Et, i-Pr, n-Pr, n-Bu, t-Bu, s-Bu or H; $R^3$ is H, Me, Et, i-Pr, n-Pr, n-Bu, t-Bu, or s-Bu; $R^4$ is H, Me, Et, i-Pr, n-Pr, n-Bu, t-Bu, or s-Bu; $R^5$ is H, F, Cl, Br, I, Me, Et, i-Pr, n-Pr, n-Bu, t-Bu, or s-Bu; $R^6$ is H, F, Cl, Br, I, Me, Et, i-Pr, n-Pr, n-Bu, t-Bu, or s-Bu; $R^7$ is H, F, Cl, Br, I, Me, Et, i-Pr, n-Pr, n-Bu, t-Bu, or s-Bu; $R^8$ is H, F, Cl, Br, I, Me, Et, i-Pr, n-Pr, n-Bu, t-Bu, or s-Bu; $R^9$ is H, F, Cl, Br, I, Me, Et, i-Pr, n-Pr, n-Bu, t-Bu, or s-Bu; $R^{10}$ is H, F, Cl, Br, I, Me, Et, i-Pr, n-Pr, n-Bu, t-Bu, or s-Bu; $R^{11}$ is H, Me, F, Cl, Br, I, Et, i-Pr, n-Pr, n-Bu, t-Bu, or s-Bu; $R^{12}$ is H, F, Cl, Br, I, Me, Et, i-Pr, n-Pr, n-Bu, t-Bu, or s-Bu; $R^{13}$ is H, Me, F, Cl, Br, I, Et, n-Pr, i-Pr, n-Bu, t-Bu or s-Bu; $R^{14}$ is F, Cl, Br, I, Me, Et, i-Pr, n-Pr, n-Bu, t-Bu, s-Bu or H; $R^{15}$ is H, Me, Et, i-Pr, n-Pr, n-Bu, t-Bu, s-Bu, F, Br, I, Cl, or together with $R^{16}$ forms a naphthyl or a phenanthryl ring; $R^{16}$ is H, F, Cl, Br, I, or together with $R^{15}$ forms a naphthyl or a phenanthryl ring; $R^{17}$ is H, F, Cl, Br, I, or together with $R^{18}$ forms a naphthyl, or a phenanthryl ring; $R^{18}$ is H, Cl, F, Br, I, 3,5-dichloro-phenyl, phenyl, Me, Et, i-Pr, n-Pr, n-Bu, t-Bu, s-Bu or together with $R^{17}$ forms a naphthyl, or a phenanthryl; $R^{19}$ is H, phenyl, $C_{1-6}$ alkyl, —$C(R^{34})(R^{35})$ $COOR^{36}$, —$C(R^{34})(R^{35})$ $C(O)H$, —$C(R^{34})(R^{35})$ $C(O)R^{37}$, —$C(R^{34})(R^{35})$ $CR^{38}(OR^{39})(OR^{40})$, —$C(R^{34})(R^{35})$ $C(O)$ $NR^{41}R^{42}$, —$C(R^{34})(R^{35})$ $C(O)$ $NR^{41}OR^{40}$; $R^{20}$ is H, F, Cl, Br, I, Me, Et, i-Pr, n-Pr, n-Bu, t-Bu, s-Bu, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, pyridine, piperidine, imidazole, indolizine, indazole, optionally substituted $C_{3-8}$ cycloalkyl, phenyl, naphthalene, or cyclohexene; $R^{21}$ is H, phenyl, Me, Et, i-Pr, n-Pr, n-Bu, t-Bu, s-Bu, —$NR^{27}R^{28}$ F, Cl, Br, or I; $R^{22}$ is H, Me, Et, i-Pr, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, pyridine, piperidine, imidazole, indolizine, indazole, cyclohexyl, phenyl, naphthalene, cyclohexene F, Cl, Br, or I; $R^{22}$ is H, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, or —SR; $R^{23}$ is H, F, Cl, Br, I, phenyl, Me, Et, i-Pr, n-Pr, n-Bu, t-Bu, or s-Bu; $R^{24}$ is H; $R^{24}$ is H, or Me; $R^{25}$ is OH, $OR^{30}$, $NR^{27}R^{28}$, Me, Et, or i-Pr, $R^{26}$ is H, Me, Et, i-Pr, n-Pr, n-Bu, t-Bu, or s-Bu; $R^{27}$ is H, Me, Et, or i-Pr; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, or —$NR^{27}R^{28}$; $R^{30}$ is Me, Et, i-Pr, n-Pr, n-Bu, t-Bu, or s-Bu; $R^{31}$ is H, Me, Et, i-Pr, n-Pr, n-Bu, t-Bu, or s-Bu; $R^{32}$ is Me, Et, n-Pr or H; $R^{33}$ is H, Me, Et, Me, Et, i-Pr, n-Pr, n-Bu, t-Bu, s-Bu, or together with $R^{19}$ forms a morpholino, a thiomorpholino, a pyrrolidino, a piperidino, or a piperazino ring; $R^{34}$ is H, Me, Et, i-Pr, n-Pr, n-Bu, t-Bu, or s-Bu; $R^{35}$ is H, or Me, Et, i-Pr, n-Pr, n-Bu, t-Bu, or s-Bu; $R^{36}$ is H, Me, Et, i-Pr, n-Pr, n-Bu, t-Bu, or s-Bu; $R^{37}$ is Me, Et, i-Pr, n-Pr, n-Bu, t-Bu, or s-Bu; $R^{38}$ is H or Me, Et, i-Pr, n-Pr, n-Bu, t-Bu, or s-Bu; $R^{39}$ is H, Me, Et, i-Pr, n-Pr, n-Bu, t-Bu, or s-Bu; $R^{40}$ is H, Me, Et, i-Pr, n-Pr, n-Bu, t-Bu, or s-Bu; $R^{41}$ is H, Me, Et, i-Pr, n-Pr, n-Bu, t-Bu, or s-Bu; $R^{42}$ is H, Me, Et, i-Pr, n-Pr, n-Bu, t-Bu, or s-Bu; and x is 1 or 2.

In one embodiment, the invention provides a method for producing at least one E-macrocyclic product represented by Formula (III), wherein: $R^{r2}$ is H or linear $C_{1-3}$ alkyl; n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (II) wherein: n is 1, 2, 3, 4, 5 or 6; m is 4, 5, 6 or 7; R is H, linear or branched $C_{1-12}$ alkyl; $R^{r1}$ is H, linear or branched $C_{1-12}$ alkyl; $R^{r2}$ is H or linear $C_{1-3}$ alkyl; and with the proviso that only one of R and $R^{r1}$ can be H; to a macrocyclic ring-closing metathesis reaction in the presence of a stereoretentive ruthenium olefin metathesis catalyst represented by Formula (I), wherein: X is S; Y is S; Z is N; W is O; $R^1$ is Me or H; $R^2$ is Me or H; $R^3$ is H; $R^4$ is H; $R^5$ is H, F, Me, t-Bu or i-Pr; $R^6$ is H or t-Bu; $R^7$ is H, F or Me; $R^8$ is H, F or t-Bu; $R^9$ is H, F, Me, t-Bu or i-Pr, $R^{10}$ is H, F, Me, t-Bu or i-Pr; $R^{11}$ is H or t-Bu; $R^{12}$ is H, F or Me; $R^{13}$ is H, F or t-Bu; $R^{14}$ is F, Me, i-Pr, t-Bu or H; $R^{15}$ is H, Me, F, Br, I, Cl, or together with $R^{16}$ forms a naphthyl; $R^{16}$ is H, or together with $R^{15}$ forms a naphthyl; $R^{17}$ is H or together with $R^{18}$ forms a naphthyl, or a phenanthryl ring; $R^{18}$ is Cl, F, Br, I, 3,5-dichloro-phenyl, phenyl, t-Bu or together with $R^{17}$ forms a naphthyl, or a phenanthryl ring; $R^{19}$ is i-Pr; $R^{20}$ is H or phenyl; $R^{21}$ is H; $R^{22}$ is H, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$; $R^{23}$ is H; $R^{24}$ is H; $R^{25}$ is OH, $OR^{30}$, $NR^{27}R^{28}$, Me, Et, or i-Pr; $R^{26}$ is H, Me, Et, i-Pr, n-Pr, n-Bu, t-Bu, or s-Bu; $R^{27}$ is H, Me, Et, i-Pr, n-Pr, n-Bu, t-Bu, or s-Bu; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, —$NR^{27}R^{28}$; $R^{30}$ is Me, Et, i-Pr, n-Pr, n-Bu, t-Bu, or s-Bu; and $R^{31}$ is H, Me, Et, i-Pr, n-Pr, n-Bu, t-Bu, or s-Bu.

In one embodiment, the invention provides a method for producing at least one E-macrocyclic product represented by Formula (III), wherein: $R^{r2}$ is H or linear $C_{1-3}$ alkyl; n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (II) wherein $R^{r1}$ is H, linear or branched $C_{1-12}$ alkyl; $R^{r2}$ is H or linear $C_{1-3}$ alkyl; and with the proviso that only one of R and $R^{r1}$ can be H; n is 1, 2, 3, 4, 5 or 6; and m is 4, 5, 6 or 7; to a ring-closing metathesis reaction in the presence of a stereoretentive ruthenium olefin metathesis catalyst represented by Formula (I), wherein: X is S; Y is S; Z is N; W is O; $R^1$ is Me; $R^2$ is Me; $R^3$ is H; $R^4$ is H; $R^5$ is F; $R^6$ is H; $R^7$ is H or F; $R^8$ is H; $R^9$ is F; $R^{10}$ is F; $R^{11}$ is H; $R^{12}$ is H; $R^{13}$ is H; $R^{14}$ is F; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (III), wherein: $R^{r2}$ is H or linear $C_{1-3}$ alkyl; n is 1, 2, 3, 4, 5 or 6; m is 4, 5, 6, or 7; and the E-macrocyclic product of Formula (III) is a twelve, thirteen fourteen, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (II) wherein $R^{r1}$ is H, linear or branched $C_{1-12}$ alkyl; $R^{r2}$ is H or linear $C_{1-3}$ alkyl; and with the proviso that only one of R and $R^{r1}$ can be H; n is 1, 2, 3, 4, 5 or 6; and m is 4, 5, 6 or 7; to a ring-closing metathesis reaction in the presence of a stereoretentive ruthenium olefin metathesis catalyst represented by Formula (I), wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (III), wherein: $R^{r2}$ is H or Me; n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (II) wherein R is H, Me, Et, n-Pr or n-Bu; $R^{r1}$ is H, Me, Et, n-Pr or n-Bu; $R^{r2}$ is H or Me; n is 1, 2, 3, 4, 5 or 6; and m is 4, 5, 6 or 7; with the proviso that only one of R and $R^{r1}$ can be H; to a ring-closing metathesis reaction in the presence of a stereoretentive ruthenium olefin metathesis catalyst represented by Formula (I), as defined herein.

In one embodiment, the invention provides a method for producing at least one E-macrocyclic product represented by Formula (III), wherein: $R^{r2}$ is H or Me; n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (II) wherein R is H, Me, Et, n-Pr or n-Bu; $R^{r1}$ is H, Me, Et, n-Pr or n-Bu; $R^{r2}$ is H or Me; n is 1, 2, 3, 4, 5 or 6; and m is 4, 5, 6 or 7; with the proviso that only one of R and $R^{r1}$ can be H; to a ring-closing metathesis reaction in the presence of a stereo-retentive ruthenium olefin metathesis catalyst represented by Formula (I), wherein: X is S; Y is S; Z is N or $CR^{32}$; W is O or $NR^{33}$; $R^1$ is H, linear or branched $C_{1-6}$ alkyl, or halogen; $R^2$ is H linear or branched $C_{1-6}$ alkyl, or halogen; $R^3$ is H, linear or branched $C_{1-6}$ alkyl, or halogen; $R^4$ is H, linear or branched $C_{1-6}$ alkyl or halogen; $R^5$ is H, linear or branched $C_{1-6}$ alkyl; $R^6$ is H, linear or branched $C_{1-6}$ alkyl; $R^7$ is H, linear or branched $C_{1-6}$ alkyl; $R^8$ is H or $C_{1-6}$ alkyl; $R^9$ is H, linear or branched $C_{1-6}$ alkyl; $R^{10}$ is H, linear or branched $C_{1-6}$ alkyl; $R^{11}$ is H, linear or branched $C_{1-6}$ alkyl; $R^{12}$ is H, linear or branched $C_{1-6}$ alkyl; $R^{13}$ is H, linear or branched $C_{1-6}$ alkyl or together with $R^{14}$ forms a naphthyl ring; $R^{14}$ is H, linear or branched $C_{1-6}$ alkyl or together with $R^{13}$ forms a naphthyl ring; $R^{15}$ is H, phenyl, linear or branched $C_{1-6}$ alkyl, halogen or together with $R^{16}$ forms a naphthyl ring; $R^{16}$ is H, phenyl, linear or branched $C_{1-6}$ alkyl, halogen or together with $R^{15}$ or together with $R^{17}$ forms a naphthyl ring; $R^{17}$ is H, phenyl, linear or branched $C_{1-6}$ alkyl, halogen or together with $R^{16}$ or together with $R^{18}$ forms a naphthyl ring; $R^{18}$ is H, phenyl, linear or branched $C_{1-6}$ alkyl, halogen or together with $R^{16}$ or together with $R^{18}$ forms a naphthyl ring; $R^{19}$ is H, phenyl, $C_{1-6}$alkyl, $-C(R^{34})(R^{35})$ $COOR^{36}$, $-C(R^{34})(R^{35})$ C(O)H, $-C(R^{34})(R^{35})$ C(O) $R^{37}$, $-C(R^{34})(R^{35})$ $CR^{38}(OR^{39})(OR^{40})$, $-C(R^{34})(R^{35})$ C(O) $NR^{41}R^{42}$, $-C(R^{34})(R^{35})$ C(O) $NR^{41}OR^{40}$ or together with $R^{33}$ forms a five, six or seven membered heterocyclic ring; $R^{20}$ is H, linear or branched $C_{1-16}$ alkyl, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, pyridine, piperidine, imidazole, indolizine, indazole, optionally substituted $C_{3-8}$ cycloalkyl, phenyl, naphthalene, cyclohexene or together with $R^{21}$ can form a polycycle; $R^{21}$ is H, phenyl, $-NR^{27}R^{28}$, linear or branched $C_{1-6}$ alkyl, halogen or together with $R^{20}$ or together with $R^{22}$ can form a polycycle; $R^{22}$ is H, linear or branched $C_{1-6}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, pyridine, piperidine, imidazole, indolizine, indazole, optionally substituted $C_{3-8}$ cycloalkyl, phenyl, naphthalene, cyclohexene or together with $R^{21}$ or together with $R^{23}$ can form a polycycle; $R^{23}$ is H, phenyl, linear or branched $C_{1-6}$ alkyl or together with $R^{22}$ can form a polycycle; $R^{24}$ is H, linear or branched $C_{1-6}$ alkyl; $R^{25}$ is OH, $OR^{30}$, $NR^{27}R^{28}$, linear or branched $C_{1-6}$ alkyl; $R^{26}$ is H, linear or branched $C_{1-6}$ alkyl; $R^{27}$ is H, linear or branched $C_{1-6}$ alkyl; $R^{28}$ is H, linear or branched $C_{1-6}$ alkyl; $R^{29}$ is H, linear or branched $C_{1-6}$ alkyl, $-NR^{27}R^{28}$; $R^{30}$ is optionally substituted $C_{1-6}$ alkyl, optionally substituted $C_{3-8}$ cycloalkyl, optionally substituted heterocycle, optionally substituted phenyl or optionally substituted $C_{3-8}$ cycloalkenyl; $R^{31}$ is H, linear or branched $C_{1-6}$ alkyl; $R^{32}$ is H, linear or branched $C_{1-6}$ alkyl; $R^{33}$ is H, linear or branched $C_{1-6}$ alkyl, or together with $R^{19}$ forms a five, six or seven membered heterocyclic ring; $R^{34}$ is H, or linear or branched $C_{1-6}$ alkyl; $R^{35}$ is H, or linear or branched $C_{1-6}$ alkyl; $R^{36}$ is H, linear or branched $C_{1-6}$ alkyl; $R^{37}$ is linear or branched $C_{1-6}$ alkyl; $R^{38}$ is H or linear or branched $C_{1-6}$ alkyl; $R^{39}$ is H, linear or branched $C_{1-6}$ alkyl; $R^{40}$ is H, linear or branched $C_{1-6}$ alkyl; $R^{41}$ is H, linear or branched $C_{1-6}$ alkyl; $R^{42}$ is H, linear or branched $C_{1-6}$ alkyl; and x is 1 or 2.

In one embodiment, the invention provides a method for producing at least one E-macrocyclic product represented by Formula (III), wherein: $R^{r2}$ is H or Me; n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (II) wherein R is H, Me, Et, n-Pr or n-Bu; $R^{r1}$ is H, Me, Et, n-Pr or n-Bu; $R^{r2}$ is H or Me; n is 1, 2, 3, 4, 5 or 6; and m is 4, 5, 6 or 7; with the proviso that only one of R and $R^{r1}$ can be H; to a ring-closing metathesis reaction in the presence of a stereo-retentive ruthenium olefin metathesis catalyst represented by Formula (I), wherein X is S; Y is S; Z is N; W is O; $R^1$ is Me or H; $R^2$ is Me or H; $R^3$ is H; $R^4$ is H; $R^5$ is H, F, Me, t-Bu or i-Pr; $R^6$ is H or t-Bu; $R^7$ is H, F or Me; $R^8$ is H, F or t-Bu; $R^9$ is H, F, Me, t-Bu or i-Pr; $R^{10}$ is H, F, Me, t-Bu or i-Pr, $R^{11}$ is H or t-Bu; $R^{12}$ is H, F or Me; $R^{13}$ is H, F or t-Bu; $R^{14}$ is F, Me, i-Pr, t-Bu or H; $R^{15}$ is H, Me, F, Br, I, Cl, or together with $R^{16}$ forms a naphthyl; $R^{16}$ is H, or together with $R^{15}$ forms a naphthyl; $R^{17}$ H or together with $R^{18}$ forms a naphthyl, or a phenanthryl ring; $R^{18}$ is Cl, F, Br, I, 3,5-dichloro-phenyl, phenyl, t-Bu or together with $R^{17}$ forms a naphthyl, or a phenanthryl ring; $R^{19}$ is i-Pr; $R^{20}$ is H or phenyl; $R^{21}$ is H; $R^{22}$ is H, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$; $R^{23}$ is H; $R^{24}$ is H; $R^{25}$ is OH, $OR^{30}$, $NR^{27}R^{28}$, Me, Et, or i-Pr, $R^{26}$ is H, Me, Et, i-Pr, n-Pr, n-Bu, t-Bu, or s-Bu; $R^{27}$ is H, Me, Et, i-Pr, n-Pr, n-Bu, t-Bu, or s-Bu; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, $-NR^{27}R^{28}$; $R^{30}$ is Me, Et, i-Pr, n-Pr, n-Bu, t-Bu, or s-Bu; and $R^{31}$ is H, Me, Et, i-Pr, n-Pr, n-Bu, t-Bu, or s-Bu.

In one embodiment, the invention provides a method for producing at least one E-macrocyclic product represented by Formula (III), wherein: $R^{r2}$ is H or Me; n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (II) wherein R is H, Me, Et, n-Pr or n-Bu; $R^{r1}$ is H, Me, Et, n-Pr or n-Bu; $R^{r2}$ is H or Me; n is 1, 2, 3, 4, 5 or 6; and m is 4, 5, 6 or 7; with the proviso that only one of R and $R^{r1}$ can be H; to a ring-closing metathesis reaction in the presence of a stereo-retentive ruthenium olefin metathesis catalyst represented by Formula (I), wherein: X is S; Y is S; Z is N or $CR^{32}$; W is O, $NR^{33}$ or S; $R^1$ is Me, Et, i-Pr, n-Pr, n-Bu, t-Bu, s-Bu or H; $R^2$ is Me, Et, i-Pr, n-Pr, n-Bu, t-Bu, s-Bu or H; $R^3$ is H, Me, Et, i-Pr, n-Pr, n-Bu, t-Bu, or s-Bu; $R^4$ is H, Me, Et, i-Pr, n-Pr, n-Bu, t-Bu, or s-Bu; $R^5$ is H, F, Cl, Br, I, Me, Et, i-Pr, n-Pr, n-Bu, t-Bu, or s-Bu; $R^6$ is H, F, Cl, Br, I, Me, Et, i-Pr, n-Pr, n-Bu, t-Bu, or s-Bu; $R^7$ is H, F, Cl, Br, I, Me, Et, i-Pr, n-Pr, n-Bu, t-Bu, or s-Bu; $R^8$ is H, F, Cl, Br, I, Me, Et, i-Pr, n-Pr, n-Bu, t-Bu, or s-Bu; $R^9$ is H, F, Cl, Br, I, Me, Et, i-Pr, n-Pr, n-Bu, t-Bu, or s-Bu; $R^{10}$ is H, F, Cl, Br, I, Me, Et, i-Pr, n-Pr, n-Bu, t-Bu, or s-Bu; $R^{11}$ is H, Me, F, Cl, Br, I, Et, i-Pr, n-Pr, n-Bu, t-Bu, or s-Bu; $R^{12}$ is H, F, Cl, Br, I, Me, Et, i-Pr, n-Pr, n-Bu, t-Bu, or s-Bu; $R^{13}$ is H, Me, F, Cl, Br, I, Et, n-Pr, i-Pr, n-Bu, t-Bu or s-Bu; $R^{14}$ is F, Cl, Br, I, Me, Et, i-Pr, n-Pr, n-Bu, t-Bu, s-Bu or H; $R^{15}$ is H, Me, Et, i-Pr, n-Pr, n-Bu, t-Bu, s-Bu, F, Br, I, Cl, or together with $R^{16}$ forms a naphthyl or a phenanthryl ring; $R^{16}$ is H, F, Cl, Br, I, or together with $R^{15}$ forms a naphthyl or a phenanthryl ring; $R^{17}$ is H, F, Cl, Br, I, or together with $R^{18}$ forms a naphthyl, or a phenanthryl ring; $R^{18}$ is H, Cl, F, Br, I, 3,5-dichloro-phenyl, phenyl, Me, Et, i-Pr, n-Pr, n-Bu, t-Bu, s-Bu or together with $R^{17}$ forms a naphthyl, or a phenanthryl; $R^{19}$ is H, phenyl, $C_{1-6}$ alkyl, —C($R^{34}$)($R^{35}$) COOR$^{36}$, —C($R^{34}$)($R^{35}$) C(O)H, —C($R^{34}$)($R^{35}$) C(O)$R^{37}$, —C($R^{34}$)($R^{35}$) CR$^{38}$(OR$^{39}$)(OR$^{40}$), —C($R^{34}$)($R^{35}$) C(O) NR$^{41}$R$^{42}$, —C($R^{34}$)($R^{35}$) C(O) NR$^{41}$OR$^{40}$; $R^{20}$ is H, F, Cl, Br, I, Me, Et, i-Pr, n-Pr, n-Bu, t-Bu, s-Bu, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, pyridine, piperidine, imidazole, indolizine, indazole, optionally substituted $C_{3-8}$ cycloalkyl, phenyl, naphthalene, or cyclohexene; $R^{21}$ is H, phenyl, Me, Et, i-Pr, n-Pr, n-Bu, t-Bu, s-Bu, —NR$^{27}$R$^{28}$ F, Cl, Br, or I; $R^{22}$ is H, Me, Et, i-Pr, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, pyridine, piperidine, imidazole, indolizine, indazole, cyclohexyl, phenyl, naphthalene, cyclohexene F, Cl, Br, or I; $R^{22}$ is H, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, or —SR$^{31}$; $R^{23}$ is H, F, Cl, Br, I, phenyl, Me, Et, i-Pr, n-Pr, n-Bu, t-Bu, or s-Bu; $R^{24}$ is H; $R^{24}$ is H, or Me; $R^{25}$ is OH, OR$^{30}$, NR$^{27}$R$^{28}$, Me, Et, or i-Pr; $R^{26}$ is H, Me, Et, i-Pr, n-Pr, n-Bu, t-Bu, or s-Bu; $R^{27}$ is H, Me, Et, or i-Pr; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, or —NR$^{27}$R$^{28}$; $R^{30}$ is Me, Et, i-Pr, n-Pr, n-Bu, t-Bu, or s-Bu; $R^{31}$ is H, Me, Et, i-Pr, n-Pr, n-Bu, t-Bu, or s-Bu; $R^{32}$ is Me, Et, n-Pr or H; $R^{33}$ is H, Me, Et, Me, Et, i-Pr, n-Pr, n-Bu, t-Bu, s-Bu, or together with $R^{19}$ forms a morpholino, a thio-morpholino, a pyrrolidino, a piperidino, or a piperazino ring; $R^{34}$ is H, Me, Et, i-Pr, n-Pr, n-Bu, t-Bu, or s-Bu; $R^{35}$ is H, or Me, Et, i-Pr, n-Pr, n-Bu, t-Bu, or s-Bu; $R^{36}$ is H, Me, Et, i-Pr, n-Pr, n-Bu, t-Bu, or s-Bu; $R^{37}$ is Me, Et, i-Pr, n-Pr, n-Bu, t-Bu, or s-Bu; $R^{38}$ is H or Me, Et, i-Pr, n-Pr, n-Bu, t-Bu, or s-Bu; $R^{39}$ is H, Me, Et, i-Pr, n-Pr, n-Bu, t-Bu, or s-Bu; $R^{40}$ is H, Me, Et, i-Pr, n-Pr, n-Bu, t-Bu, or s-Bu; $R^{41}$ is H, Me, Et, i-Pr, n-Pr, n-Bu, t-Bu, or s-Bu; $R^{42}$ is H, Me, Et, i-Pr, n-Pr, n-Bu, t-Bu, or s-Bu; and x is 1 or 2.

In one embodiment, the invention provides a method for producing at least one E-macrocyclic product represented by Formula (III), wherein: $R^{r2}$ is H or Me; n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (II) wherein R is H, Me, Et, n-Pr or n-Bu; $R^{r1}$ is H, Me, Et, n-Pr or n-Bu; $R^{r2}$ is H or Me; n is 1, 2, 3, 4, 5 or 6; and m is 4, 5, 6 or 7; with the proviso that only one of R and $R^{r1}$ can be H; to a ring-closing metathesis reaction in the presence of a stereoretentive ruthenium olefin metathesis catalyst represented by Formula (I), wherein: X is S; Y is S; Z is N; W is O; $R^1$ is Me; $R^2$ is Me; $R^3$ is H; $R^4$ is H; $R^5$ is F; $R^6$ is H; $R^7$ is H or F; $R^8$ is H; $R^9$ is F; $R^{10}$ is F; $R^{11}$ is H; $R^{12}$ is H; $R^{13}$ is H; $R^{14}$ is F; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (III), wherein: $R^{r2}$ is H or Me; n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (II) wherein R is H, Me, Et, n-Pr or n-Bu; $R^{r1}$ is H, Me, Et, n-Pr or n-Bu; $R^{r2}$ is H or Me; n is 1, 2, 3, 4, 5 or 6; and m is 4, 5, 6 or 7; with the proviso that only one of R and $R^{r1}$ can be H; to a ring-closing metathesis reaction in the presence of a stereoretentive ruthenium olefin metathesis catalyst represented by Formula (I), wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (III), wherein: $R^{r2}$ is H; n is 2; m is 4, 6, or 7; and the E-macrocyclic product of Formula (III) is a twelve, fourteen, fifteen-membered ring with an E-selectivity of 95, or 98, or 99, or >99%; comprising: subjecting a diene substrate bearing one E-olefin and one terminal olefin, represented by Formula (II) wherein R is Me; $R^{r1}$ is Me; $R^{r2}$ is H; n is 2; and m is 4, 6 or 7; to a ring-closing metathesis reaction in the presence of a stereoretentive ruthenium olefin metathesis catalyst represented by Formula (I), as defined herein.

In one embodiment, the invention provides a method for producing at least one E-macrocyclic product represented by Formula (III), wherein: $R^{r2}$ is H; n is 2; m is 4, 6, or 7; and the E-macrocyclic product of Formula (III) is a twelve, fourteen, fifteen-membered ring with an E-selectivity of 95, or 98, or 99, or >99%; comprising: subjecting a diene substrate bearing two E-olefins represented by Formula (II) wherein R is Me; $R^{r1}$ is Me; $R^{r2}$ is H; n is 2; and m is 4, 6 or 7; to a ring-closing metathesis reaction in the presence of a stereoretentive ruthenium olefin metathesis catalyst represented by Formula (I), wherein: X is S; Y is S; Z is N or S; W is O, NR$^{33}$ or S; $R^1$ is Me, Et, i-Pr, n-Pr, n-Bu, t-Bu, s-Bu or H; $R^2$ is Me, Et, i-Pr, n-Pr, n-Bu, t-Bu, s-Bu or H; $R^3$ is H, Me, Et, i-Pr, n-Pr, n-Bu, t-Bu, or s-Bu; $R^4$ is H, Me, Et, i-Pr, n-Pr, n-Bu, t-Bu, or s-Bu; $R^5$ is H, F, Cl, Br, I, Me, Et, i-Pr, n-Pr, n-Bu, t-Bu, or s-Bu; $R^6$ is H, F, Cl, Br, I, Me, Et, i-Pr, n-Pr, n-Bu, t-Bu, or s-Bu; $R^7$ is H, F, Cl, Br, I, Me, Et, i-Pr, n-Pr, n-Bu, t-Bu, or s-Bu; $R^8$ is H, F, Cl, Br, I, Me, Et, i-Pr, n-Pr, n-Bu, t-Bu, or s-Bu; $R^9$ is H, F, Cl, Br, I, Me, Et, i-Pr, n-Pr, n-Bu, t-Bu, or s-Bu; $R^{10}$ is H, F, Cl, Br, I, Me, Et, i-Pr, n-Pr, n-Bu, t-Bu, or s-Bu; $R^{11}$ is H, Me, F, Cl, Br, I, Et, i-Pr, n-Pr, n-Bu, t-Bu, or s-Bu; $R^{12}$ is H, F, Cl, Br, I, Me, Et, i-Pr, n-Pr, n-Bu, t-Bu, or s-Bu; $R^{13}$ is H, Me, F, Cl, Br, I, Et, n-Pr, i-Pr, n-Bu, t-Bu or s-Bu; $R^{14}$ is F, Cl, Br, I, Me, Et, i-Pr, n-Pr, n-Bu, t-Bu, s-Bu or H; $R^{15}$ is H, Me, Et, i-Pr, n-Pr, n-Bu, t-Bu, s-Bu, F, Br, I, Cl, or together with $R^{16}$ forms a naphthyl or a phenanthryl ring; $R^{16}$ is H, F, Cl, Br, I, or together with $R^{15}$ forms a naphthyl or a phenanthryl ring; $R^{17}$ is H, F, Cl, Br, I, or together with $R^{18}$ forms a naphthyl, or a phenanthryl ring; $R^{18}$ is H, Cl, F, Br, I, 3,5-dichloro-phenyl, phenyl, Me, Et, i-Pr, n-Pr, n-Bu, t-Bu, s-Bu or together with $R^{17}$ forms a naphthyl, or a phenanthryl; $R^{19}$ is H, phenyl, $C_{1-6}$ alkyl, —C($R^{34}$)($R^{35}$) COOR$^{36}$, —C($R^{34}$)($R^{35}$) C(O)H, —C($R^{34}$)($R^{35}$) C(O)$R^{37}$, —C($R^{34}$)($R^{35}$) CR$^{38}$(OR$^{39}$)(OR$^{40}$), —C($R^{34}$)($R^{35}$) C(O) NR$^{41}$R$^{42}$, —C($R^{34}$)($R^{35}$) C(O) NR$^{41}$OR$^{40}$; $R^{20}$ is H, F, Cl, Br, I, Me, Et, i-Pr, n-Pr, n-Bu, t-Bu, s-Bu, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, pyridine, piperidine, imidazole, indolizine, indazole, optionally substituted $C_{3-8}$ cycloalkyl, phenyl, naphthalene, or cyclohexene; $R^{21}$ is H, phenyl, Me, Et, i-Pr, n-Pr, n-Bu, t-Bu, s-Bu, —NR$^{27}$R$^{28}$ F, Cl, Br, or I; $R^{22}$ is H, Me, Et, i-Pr, halogen, —C(O)$R^{25}$, —OR$^{26}$, CN, —NR$^{27}$R$^{28}$, NO$_2$, —CF$_3$, —S(O)$_x$R$^{29}$, —P(O)

(OH)$_2$, —OP(O)(OH)$_2$, —SR$^{31}$, pyridine, piperidine, imidazole, indolizine, indazole, cyclohexyl, phenyl, naphthalene, cyclohexene F, Cl, Br, or I; R$^{22}$ is H, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, or —SR$^{31}$; R$^{23}$ is H, F, Cl, Br, I, phenyl, Me, Et, i-Pr, n-Pr, n-Bu, t-Bu, or s-Bu; R$^{24}$ is H; R$^{24}$ is H, or Me; R$^{25}$ is OH, OR$^{30}$, NR$^{27}$R$^{28}$, Me, Et, or i-Pr; R$^{26}$ is H, Me, Et, i-Pr, n-Pr, n-Bu, t-Bu, or s-Bu; R$^{27}$ is H, Me, Et, or i-Pr; R$^{28}$ is H Me, Et, i-Pr, n-Pr, n-Bu, t-Bu, or s-Bu; R$^{29}$ is H, Me, Et, i-Pr, n-Pr, n-Bu, t-Bu, s-Bu, or —NR$^{27}$R$^{28}$; R$^{30}$ is Me, Et, i-Pr, n-Pr, n-Bu, t-Bu, or s-Bu; R$^{31}$ is H, Me, Et, i-Pr, n-Pr, n-Bu, t-Bu, or s-Bu; R$^{32}$ is Me, Et, n-Pr or H; R$^{33}$ is H, Me, Et, Me, Et, i-Pr, n-Pr, n-Bu, t-Bu, s-Bu, or together with R$^{19}$ forms a morpholino, a thio-morpholino, a pyrrolidino, a piperidino, or a piperazino ring; R$^{34}$ is H, Me, Et, i-Pr, n-Pr, n-Bu, t-Bu, or s-Bu; R$^{35}$ is H, or Me, Et, i-Pr, n-Pr, n-Bu, t-Bu, or s-Bu; R$^{36}$ is H, Me, Et, i-Pr, n-Pr, n-Bu, t-Bu, or s-Bu; R$^{37}$ is Me, Et, i-Pr, n-Pr, n-Bu, t-Bu, or s-Bu; R$^{38}$ is H or Me, Et, i-Pr, n-Pr, n-Bu, t-Bu, or s-Bu; R$^{39}$ is H, Me, Et, i-Pr, n-Pr, n-Bu, t-Bu, or s-Bu; R$^{40}$ is H, Me, Et, i-Pr, n-Pr, n-Bu, t-Bu, or s-Bu; R$^{41}$ is H, Me, Et, i-Pr, n-Pr, n-Bu, t-Bu, or s-Bu; R$^{42}$ is H, Me, Et, i-Pr, n-Pr, n-Bu, t-Bu, or s-Bu; and x is 1 or 2.

In one embodiment, the invention provides a method for producing at least one E-macrocyclic product represented by Formula (III), wherein: R$^{r2}$ is H; n is 2; m is 4, 6, or 7; and the E-macrocyclic product of Formula (III) is a twelve, fourteen, fifteen-membered ring with an E-selectivity of 95, or 98, or 99, or >99%; comprising: subjecting a diene substrate bearing two E-olefins represented by Formula (II) wherein R is Me; R$^{r1}$ is Me; R$^{r2}$ is H; n is 2; and m is 4, 6 or 7; to a ring-closing metathesis reaction in the presence of a stereoretentive ruthenium olefin metathesis catalyst represented by Formula (I), wherein: X is S; Y is S; Z is N; W is O; R$^1$ is Me or H; R$^2$ is Me or H; R$^3$ is H; R$^4$ is H; R$^5$ is H, F, Me, t-Bu or i-Pr; R$^6$ is H or t-Bu; R$^7$ is H, F or Me; R$^8$ is H, F or t-Bu; R$^9$ is H, F, Me, t-Bu or i-Pr, R$^{10}$ is H, F, Me, t-Bu or i-Pr; R$^{11}$ is H or t-Bu; R$^{12}$ is H, F or Me; R$^{13}$ is H, F or t-Bu; R$^{14}$ is F, Me, i-Pr, t-Bu or H; R$^{15}$ is H, Me, F, Br, I, Cl, or together with R$^{16}$ forms a naphthyl; R$^{16}$ is H, or together with R$^{15}$ forms a naphthyl; R$^{17}$ is H or together with R$^{18}$ forms a naphthyl, or a phenanthryl ring; R$^{18}$ is Cl, F, Br, I, 3,5-dichloro-phenyl, phenyl, t-Bu or together with R$^{17}$ forms a naphthyl, or a phenanthryl ring; R$^{19}$ is i-Pr; R$^{20}$ is H or phenyl; R$^{21}$ is H; R$^{22}$ is H, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$; R$^{23}$ is H; R$^{24}$ is H; R$^{25}$ is OH, OR$^{30}$, NR$^{27}$R$^{28}$, Me, Et, or i-Pr; R$^{26}$ is H, Me, Et, i-Pr, n-Pr, n-Bu, t-Bu, or s-Bu; R$^{27}$ is H, Me, Et, i-Pr, n-Pr, n-Bu, t-Bu, or s-Bu; R$^{28}$ is H, Me, Et, i-Pr, n-Pr, n-Bu, t-Bu, or s-Bu; R$^{29}$ is H, Me, Et, i-Pr, n-Pr, n-Bu, t-Bu, s-Bu, —NR$^{27}$R$^{28}$; R$^{30}$ is Me, Et, i-Pr, n-Pr, n-Bu, t-Bu, or s-Bu; and R$^{31}$ is H, Me, Et, i-Pr, n-Pr, n-Bu, t-Bu, or s-Bu.

In one embodiment, the invention provides a method for producing at least one E-macrocyclic product represented by Formula (III), wherein: R$^{r2}$ is H; n is 2; m is 4, 6, or 7; and the E-macrocyclic product of Formula (III) is a twelve, fourteen, fifteen-membered ring with an E-selectivity of 95, or 98, or 99, or >99%; comprising: subjecting a diene substrate bearing two E-olefins represented by Formula (II) wherein R is Me; R$^{r1}$ is Me; R$^{r2}$ is H; n is 2; and m is 4, 6 or 7; to a ring-closing metathesis reaction in the presence of a stereoretentive ruthenium olefin metathesis catalyst represented by Formula (I), wherein: X is S; Y is S; Z is N; W is O; R$^1$ is Me; R$^2$ is Me; R$^3$ is H; R$^4$ is H; R$^5$ is F; R$^6$ is H; R$^7$ is H or F; R$^8$ is H; R$^9$ is F; R$^{10}$ is F; R$^{11}$ is H; R$^{12}$ is H; R$^{13}$ is H; R$^{14}$ is F; R$^{15}$ is Cl; R$^{16}$ is H; R$^{17}$ is H; R$^{18}$ is Cl; R$^{19}$ is i-Pr; R$^{20}$ is phenyl; R$^{21}$ is H; R$^{22}$ is H; R$^{23}$ is H; and R$^{24}$ is H.

In one embodiment, the invention provides a method for producing at least one E-macrocyclic product represented by Formula (III), wherein: R$^{r2}$ is H; n is 2; m is 4, 6, or 7; and the E-macrocyclic product of Formula (III) is a twelve, fourteen, fifteen-membered ring with an E-selectivity of 95, or 98, or 99, or >99%; comprising: subjecting a diene substrate bearing two E-olefins represented by Formula (II) wherein R is Me; R$^{r1}$ is Me; R$^{r2}$ is H; n is 2; and m is 4, 6 or 7; to a ring-closing metathesis reaction in the presence of a stereoretentive ruthenium olefin metathesis catalyst represented by Formula (I), wherein: X is S; Y is S; Z is N; W is O; R$^1$ is H; R$^2$ is H; R$^3$ is H; R$^4$ is H; R$^5$ is Me; R$^6$ is H; R$^7$ is Me; R$^8$ is H; R$^9$ is Me; R$^{10}$ is Me; R$^{11}$ is H; R$^{12}$ is Me; R$^{13}$ is H; R$^{14}$ is Me; R$^{15}$ is Cl; R$^{16}$ is H; R$^{17}$ is H; R$^{18}$ is Cl; R$^{19}$ is i-Pr, R$^{20}$ is phenyl; R$^{21}$ is H; R$^{22}$ is H; R$^{23}$ is H; and R$^{24}$ is H.

In one embodiment, the invention provides a method for producing at least one E-macrocyclic product represented by Formula (III), wherein: R$^{r2}$ is Me; n is 1; m is 5; and the E-macrocyclic product of Formula (III) is a twelve-membered ring with an E-selectivity of 95, or 98, or 99, or >99%; comprising: subjecting a diene substrate bearing two E-olefins represented by Formula (II) wherein R is Me; R$^{r1}$ is Me; R$^{r2}$ is Me; n is 1; and m is 5; to a ring-closing metathesis reaction in the presence of a stereoretentive ruthenium olefin metathesis catalyst represented by Formula (I), as defined herein.

In one embodiment, the invention provides a method for producing at least one E-macrocyclic product represented by Formula (III), wherein: R$^{r2}$ is Me; n is 1; m is 5; and the E-macrocyclic product of Formula (III) is a twelve-membered ring with an E-selectivity of 95, or 98, or 99, or >99%; comprising: subjecting a diene substrate bearing two E-olefins represented by Formula (II) wherein R is Me; R$^{r1}$ is Me; R$^{r2}$ is Me; n is 1; and m is 5; to a ring-closing metathesis reaction in the presence of a stereoretentive ruthenium olefin metathesis catalyst represented by Formula (I), wherein: X is S; Y is S; Z is N or CR$^{32}$; W is O, NR$^{33}$ or S; R$^1$ is Me, Et, i-Pr, n-Pr, n-Bu, t-Bu, s-Bu or H; R$^2$ is Me, Et, i-Pr, n-Pr, n-Bu, t-Bu, s-Bu or H; R$^3$ is H, Me, Et, i-Pr, n-Pr, n-Bu, t-Bu, or s-Bu; R$^4$ is H, Me, Et, i-Pr, n-Pr, n-Bu, t-Bu, or s-Bu; R$^5$ is H, F, Cl, Br, I, Me, Et, i-Pr, n-Pr, n-Bu, t-Bu, or s-Bu; R$^6$ is H, F, Cl, Br, I, Me, Et, i-Pr, n-Pr, n-Bu, t-Bu, or s-Bu; R$^7$ is H, F, Cl, Br, I, Me, Et, i-Pr, n-Pr, n-Bu, t-Bu, or s-Bu; R$^8$ is H, F, Cl, Br, I, Me, Et, i-Pr, n-Pr, n-Bu, t-Bu, or s-Bu; R$^9$ is H, F, Cl, Br, I, Me, Et, i-Pr, n-Pr, n-Bu, t-Bu, or s-Bu; R$^{10}$ is H, F, Cl, Br, I, Me, Et, i-Pr, n-Pr, n-Bu, t-Bu, or s-Bu; R$^{11}$ is H, Me, F, Cl, Br, I, Et, i-Pr, n-Pr, n-Bu, t-Bu, or s-Bu; R$^{12}$ is H, F, Cl, Br, I, Me, Et, i-Pr, n-Pr, n-Bu, t-Bu, or s-Bu; R$^{13}$ is H, Me, F, Cl, Br, I, Et, n-Pr, i-Pr, n-Bu, t-Bu or s-Bu; R$^{14}$ is F, Cl, Br, I, Me, Et, i-Pr, n-Pr, n-Bu, t-Bu, s-Bu or H; R$^{15}$ is H, Me, Et, i-Pr, n-Pr, n-Bu, t-Bu, s-Bu, F, Br, I, Cl, or together with R$^{16}$ forms a naphthyl or a phenanthryl ring; R$^{16}$ is H, F, Cl, Br, I, or together with R$^{15}$ forms a naphthyl or a phenanthryl ring; R$^{17}$ is H, F, Cl, Br, I, or together with R$^{18}$ forms a naphthyl, or a phenanthryl ring; R$^{18}$ is H, Cl, F, Br, I, 3,5-dichloro-phenyl, phenyl, Me, Et, i-Pr, n-Pr, n-Bu, t-Bu, s-Bu or together with R$^{17}$ forms a naphthyl, or a phenanthryl; R$^{19}$ is H, phenyl, C$_{1-6}$ alkyl, —C(R$^{34}$)(R$^{35}$) COOR$^{36}$, —C(R$^{34}$)(R$^{35}$) C(O)H, —C(R$^{34}$)(R$^{35}$) C(O)R$^{37}$, —C(R$^{34}$)(R$^{35}$) CR$^{38}$(OR$^{39}$)(OR$^{40}$), —C(R$^{34}$)(R$^{35}$) C(O) NR$^{41}$R$^{42}$, —C(R$^{34}$)(R$^{35}$) C(O) NR$^{41}$OR$^{40}$; R$^{20}$ is H, F, Cl, Br, I, Me, Et, i-Pr, n-Pr, n-Bu, t-Bu, s-Bu, —C(O)R$^{25}$, —OR$^{26}$, CN, —NR$^{27}$R$^{28}$, NO$_2$, —CF$_3$, —S(O)$_x$R$^{29}$, —P(O)

(OH)$_2$, —OP(O)(OH)$_2$, —SR$^{31}$, pyridine, piperidine, imidazole, indolizine, indazole, optionally substituted C$_{3-8}$ cycloalkyl, phenyl, naphthalene, or cyclohexene; R$^{21}$ is H, phenyl, Me, Et, i-Pr, n-Pr, n-Bu, t-Bu, s-Bu, —NR$^{27}$R$^{28}$ F, Cl, Br, or I; R$^{22}$ is H, Me, Et, i-Pr, halogen, —C(O)R$^{25}$, —OR$^{26}$, CN, —NR$^{27}$R$^{28}$, NO$_2$, —CF$_3$, —S(O)$_x$R$^{29}$, —P(O) (OH)$_2$, —OP(O)(OH)$_2$, —SR$^{31}$, pyridine, piperidine, imidazole, indolizine, indazole, cyclohexyl, phenyl, naphthalene, cyclohexene F, Cl, Br, or I; R$^{22}$ is H, —C(O)R$^{25}$, —OR$^{26}$, CN, —NR$^{27}$R$^{28}$, NO$_2$, —CF$_3$, —S(O)$_x$R$^{29}$, —P(O) (OH)$_2$, —OP(O)(OH)$_2$, or —SR$^{31}$; R$^{23}$ is H, F, Cl, Br, I, phenyl, Me, Et, i-Pr, n-Pr, n-Bu, t-Bu, or s-Bu; R$^{24}$ is H; R$^{24}$ is H, or Me; R$^{25}$ is OH, OR$^{30}$, NR$^{27}$R$^{28}$, Me, Et, or i-Pr; R$^{26}$ is H, Me, Et, i-Pr, n-Pr, n-Bu, t-Bu, or s-Bu; R$^{27}$ is H, Me, Et, or i-Pr; R$^{28}$ is H, Me, Et, i-Pr, n-Pr, n-Bu, t-Bu, or s-Bu; R$^{29}$ is H, Me, Et, i-Pr, n-Pr, n-Bu, t-Bu, s-Bu, or —NR$^{27}$R$^{28}$; R$^{30}$ is Me, Et, i-Pr, n-Pr, n-Bu, t-Bu, or s-Bu; R$^{31}$ is H, Me, Et, i-Pr, n-Pr, n-Bu, t-Bu, or s-Bu; R$^{32}$ is Me, Et, n-Pr or H; R$^{33}$ is H, Me, Et, Me, Et, i-Pr, n-Pr, n-Bu, t-Bu, s-Bu, or together with R$^{19}$ forms a morpholino, a thio-morpholino, a pyrrolidino, a piperidino, or a piperazino ring; R$^{34}$ is H, Me, Et, i-Pr, n-Pr, n-Bu, t-Bu, or s-Bu; R$^{35}$ is H, or Me, Et, i-Pr, n-Pr, n-Bu, t-Bu, or s-Bu; R$^{36}$ is H, Me, Et, i-Pr, n-Pr, n-Bu, t-Bu, or s-Bu; R$^{37}$ is Me, Et, i-Pr, n-Pr, n-Bu, t-Bu, or s-Bu; R$^{38}$ is H or Me, Et, i-Pr, n-Pr, n-Bu, t-Bu, or s-Bu; R$^{39}$ is H, Me, Et, i-Pr, n-Pr, n-Bu, t-Bu, or s-Bu; R$^{40}$ is H, Me, Et, i-Pr, n-Pr, n-Bu, t-Bu, or s-Bu; R$^{41}$ is H, Me, Et, i-Pr, n-Pr, n-Bu, t-Bu, or s-Bu; R$^{42}$ is H, Me, Et, i-Pr, n-Pr, n-Bu, t-Bu, or s-Bu; and x is 1 or 2.

In one embodiment, the invention provides a method for producing at least one E-macrocyclic product represented by Formula (II), wherein: R$^{r2}$ is Me; n is 1; m is 5; and the E-macrocyclic product of Formula (III) is a twelve-membered ring with an E-selectivity of 95, or 98, or 99, or >99%; comprising: subjecting a diene substrate bearing two E-olefins represented by Formula (II) wherein R is Me; R$^{r1}$ is Me; R$^{r2}$ is Me; n is 1; and m is 5; to a ring-closing metathesis reaction in the presence of a stereoretentive ruthenium olefin metathesis catalyst represented by Formula (I), wherein: X is S; Y is S; Z is N; W is O; R$^1$ is Me or H; R$^2$ is Me or H; R$^3$ is H; R$^4$ is H; R$^5$ is H, F, Me, t-Bu or i-Pr; R$^6$ is H or t-Bu; R$^7$ is H, F or Me; R$^8$ is H, F or t-Bu; R$^9$ is H, F, Me, t-Bu or i-Pr, R$^{10}$ is H, F, Me, t-Bu or i-Pr; R$^{11}$ is H or t-Bu; R$^{12}$ is H, F or Me; R$^{13}$ is H, F or t-Bu; R$^{14}$ is F, Me, i-Pr, t-Bu or H; R$^{15}$ is H, Me, F, Br, I, Cl, or together with R$^{16}$ forms a naphthyl; R$^{16}$ is H, or together with R$^{15}$ forms a naphthyl; R$^{17}$ is H or together with R$^{18}$ forms a naphthyl, or a phenanthryl ring; R$^{18}$ is Cl, F, Br, I, 3,5-dichloro-phenyl, phenyl, t-Bu or together with R$^{17}$ forms a naphthyl, or a phenanthryl ring; R$^{19}$ is i-Pr; R$^{20}$ is H or phenyl; R$^{21}$ is H; R$^{22}$ is H, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$; R$^{23}$ is H; R$^{24}$ is H; R$^{25}$ is OH, OR$^{30}$, NR$^{27}$R$^{28}$, Me, Et, or i-Pr; R$^{26}$ is H, Me, Et, i-Pr, n-Pr, n-Bu, t-Bu, or s-Bu; R$^{27}$ is H, Me, Et, i-Pr, n-Pr, n-Bu, t-Bu, or s-Bu; R$^{28}$ is H, Me, Et, i-Pr, n-Pr, n-Bu, t-Bu, or s-Bu; R$^{29}$ is H, Me, Et, i-Pr, n-Pr, n-Bu, t-Bu, s-Bu, —NR$^{27}$R$^{28}$; R$^{30}$ is Me, Et, i-Pr, n-Pr, n-Bu, t-Bu, or s-Bu; and R$^{31}$ is H, Me, Et, i-Pr, n-Pr, n-Bu, t-Bu, or s-Bu.

In one embodiment, the invention provides a method for producing at least one E-macrocyclic product represented by Formula (III), wherein: R$^{r2}$ is Me; n is 1; m is 5; and the E-macrocyclic product of Formula (III) is a twelve-membered ring with an E-selectivity of 95, or 98, or 99, or >99%; comprising: subjecting a diene substrate bearing two E-olefins represented by Formula (II) wherein R is Me; R$^{r1}$ is Me; R$^{r2}$ is Me; n is; and m is 5; to a ring-closing metathesis reaction in the presence of a stereoretentive ruthenium olefin metathesis catalyst represented by Formula (I), wherein: X is S; Y is S; Z is N; W is O; R$^1$ is Me; R$^2$ is Me; R$^3$ is H; R$^4$ is H; R$^5$ is F; R$^6$ is H; R$^7$ is H or F; R$^8$ is H; R$^9$ is F; R$^{10}$ is F; R$^{11}$ is H; R$^{12}$ is H; R$^{13}$ is H; R$^{14}$ is F; R$^{15}$ is Cl; R$^{16}$ is H; R$^{17}$ is H; R$^{18}$ is Cl; R$^{19}$ is i-Pr; R$^{20}$ is phenyl; R$^{21}$ is H; R$^{22}$ is H; R$^{23}$ is H; and R$^{24}$ is H.

In one embodiment, the invention provides a method for producing at least one E-macrocyclic product represented by Formula (III), wherein: R$^{r2}$ is Me; n is 1; m is 5; and the E-macrocyclic product of Formula (III) is a twelve-membered ring with an E-selectivity of 95, or 98, or 99, or >99%; comprising: subjecting a diene substrate bearing two E-olefins represented by Formula (I) wherein R is Me; R$^{r1}$ is Me; R$^{r2}$ is Me; n is 1; and m is 5; to a ring-closing metathesis reaction in the presence of a stereoretentive ruthenium olefin metathesis catalyst represented by Formula (I) wherein: X is S; Y is S; Z is N; W is O; R$^1$ is H; R$^2$ is H; R$^3$ is H; R$^4$ is H; R$^5$ is Me; R$^6$ is H; R$^7$ is Me; R$^8$ is H; R$^9$ is Me; R$^{10}$ is Me; R$^{11}$ is H; R$^{12}$ is Me; R$^{13}$ is H; R$^{14}$ is Me; R$^{15}$ is Cl; R$^{16}$ is H; R$^{17}$ is H; R$^{18}$ is Cl; R$^{19}$ is i-Pr; R$^{20}$ is phenyl; R$^{21}$ is H; R$^{22}$ is H; R$^{23}$ is H; and R$^{24}$ is H.

In one embodiment, the invention provides a method for producing at least one E-macrocyclic product represented by Formula (II), wherein: R$^{r2}$ is H; n is 1; m is 5, 6 or 7; and the E-macrocyclic product of Formula (III) is a twelve, thirteen, fourteen-membered ring with an E-selectivity of 95, or 98, or 99, or >99%; comprising: subjecting a diene substrate bearing two E-olefins represented by Formula (II) wherein R is Me; R$^{r1}$ is Me; R$^{r2}$ is H; n is 1; and m is 5, 6 or 7; to a ring-closing metathesis reaction in the presence of a stereoretentive ruthenium olefin metathesis catalyst represented by Formula (I), as defined herein.

In one embodiment, the invention provides a method for producing at least one E-macrocyclic product represented by Formula (III), wherein: R$^{r2}$ is H; n is 1; m is 5, 6 or 7; and the E-macrocyclic product of Formula (III) is a twelve, thirteen, fourteen-membered ring with an E-selectivity of 95, or 98, or 99, or >99%; comprising: subjecting a diene substrate bearing two E-olefins represented by Formula (II) wherein R is Me; R$^{r1}$ is Me; R$^{r2}$ is H; n is 1; and m is 5, 6 or 7; to a ring-closing metathesis reaction in the presence of a stereoretentive ruthenium olefin metathesis catalyst represented by Formula (I), wherein: X is S; Y is S; Z is N or CR$^{32}$; W is O, NR$^{33}$ or S; R$^1$ is Me, Et, i-Pr, n-Pr, n-Bu, t-Bu, s-Bu or H; R$^2$ is Me, Et, i-Pr, n-Pr, n-Bu, t-Bu, s-Bu or H; R$^3$ is H, Me, Et, i-Pr, n-Pr, n-Bu, t-Bu, or s-Bu; R$^4$ is H, Me, Et, i-Pr, n-Pr, n-Bu, t-Bu, or s-Bu; R$^5$ is H, F, Cl, Br, I, Me, Et, i-Pr, n-Pr, n-Bu, t-Bu, or s-Bu; R$^6$ is H, F, Cl, Br, I, Me, Et, i-Pr, n-Pr, n-Bu, t-Bu, or s-Bu; R$^7$ is H, F, Cl, Br, I, Me, Et, i-Pr, n-Pr, n-Bu, t-Bu, or s-Bu; R$^8$ is H, F, Cl, Br, I, Me, Et, i-Pr, n-Pr, n-Bu, t-Bu, or s-Bu; R$^9$ is H, F, Cl, Br, I, Me, Et, i-Pr, n-Pr, n-Bu, t-Bu, or s-Bu; R$^{10}$ is H, F, Cl, Br, I, Me, Et, i-Pr, n-Pr, n-Bu, t-Bu, or s-Bu; R$^{11}$ is H, Me, F, Cl, Br, I, Et, i-Pr, n-Pr, n-Bu, t-Bu, or s-Bu; R$^{12}$ is H, F, Cl, Br, I, Me, Et, i-Pr, n-Pr, n-Bu, t-Bu, or s-Bu; R$^{13}$ is H, Me, F, Cl, Br, I, Et, n-Pr, i-Pr, n-Bu, t-Bu or s-Bu; R$^{14}$ is F, Cl, Br, I, Me, Et, i-Pr, n-Pr, n-Bu, t-Bu, s-Bu or H; R$^{15}$ is H, Me, Et, i-Pr, n-Pr, n-Bu, t-Bu, s-Bu, F, Br, I, Cl, or together with R$^{16}$ forms a naphthyl or a phenanthryl ring; R$^{17}$ is H, F, Cl, Br, I, or together with R$^{15}$ forms a naphthyl or a phenanthryl ring; R$^{17}$ is H, F, Cl, Br, I, or together with R$^{18}$ forms a naphthyl, or a phenanthryl ring; R$^{18}$ is H, Cl, F, Br, I, 3,5-dichloro-phenyl, phenyl, Me, Et, i-Pr, n-Pr, n-Bu, t-Bu, s-Bu or together with R$^{17}$ forms a naphthyl, or a phenanthryl; R$^{19}$ is H, phenyl, C$_{1-6}$ alkyl, —C(R$^{34}$)(R$^{35}$) COOR$^{36}$, —C(R$^{34}$)(R$^{35}$) C(O)H, —C(R$^{34}$)(R$^{35}$) C(O)R$^{37}$, —C($R^{34}$)($R^{35}$) C$R^{38}$(O$R^{39}$)(O$R^{40}$), —C($R^{34}$)($R^{35}$) C(O) N$R^{41}R^{42}$, —C($R^{34}$)($R^{35}$) C(O) N$R^{41}$O$R^{40}$; $R^{20}$ is H, F, Cl, Br, I, Me, Et, i-Pr, n-Pr, n-Bu, t-Bu, s-Bu, —C(O)$R^{25}$, —O$R^{26}$, CN, —N$R^{27}R^{28}$, $NO_2$, —$CF_3$, —S(O)$_x R^{29}$, —P(O)(OH)$_2$, —OP(O)(OH)$_2$, —S$R^{31}$, pyridine, piperidine, imidazole, indolizine, indazole, optionally substituted $C_{3-8}$ cycloalkyl, phenyl, naphthalene, or cyclohexene; $R^{21}$ is H, phenyl, Me, Et, i-Pr, n-Pr, n-Bu, t-Bu, s-Bu, —N$R^{27}R^{28}$ F, Cl, Br, or I; $R^{22}$ is H, Me, Et, i-Pr, halogen, —C(O)$R^{25}$, —O$R^{26}$, CN, —N$R^{27}R^{28}$, $NO_2$, —$CF_3$, —S(O)$_x R^{29}$, —P(O)(OH)$_2$, —OP(O)(OH)$_2$, —S$R^{31}$, pyridine, piperidine, imidazole, indolizine, indazole, cyclohexyl, phenyl, naphthalene, cyclohexene F, Cl, Br, or I; $R^{22}$ is H, —C(O)$R^{25}$, —O$R^{26}$, CN, —N$R^{27}R^{28}$, $NO_2$, —$CF_3$, —S(O)$_x R^{29}$, —P(O)(OH)$_2$, —OP(O)(OH)$_2$, or —S$R^{31}$; $R^{23}$ is H, F, Cl, Br, I, phenyl, Me, Et, i-Pr, n-Pr, n-Bu, t-Bu, or s-Bu; $R^{24}$ is H; $R^{24}$ is H, or Me; $R^{25}$ is OH, O$R^{30}$, N$R^{27}R^{28}$, Me, Et, or i-Pr; $R^{26}$ is H, Me, Et, i-Pr, n-Pr, n-Bu, t-Bu, or s-Bu; $R^{27}$ is H, Me, Et, or i-Pr; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, or —N$R^{27}R^{28}$; $R^{30}$ is Me, Et, i-Pr, n-Pr, n-Bu, t-Bu, or s-Bu; $R^{31}$ is H, Me, Et, i-Pr, n-Pr, n-Bu, t-Bu, or s-Bu; $R^{32}$ is Me, Et, n-Pr or H; $R^{33}$ is H, Me, Et, Me, Et, i-Pr, n-Pr, n-Bu, t-Bu, s-Bu, or together with $R^{19}$ forms a morpholino, a thio-morpholino, a pyrrolidino, a piperidino, or a piperazino ring; $R^{34}$ is H, Me, Et, i-Pr, n-Pr, n-Bu, t-Bu, or s-Bu; $R^{35}$ is H, or Me, Et, i-Pr, n-Pr, n-Bu, t-Bu, or s-Bu; $R^{36}$ is H, Me, Et, i-Pr, n-Pr, n-Bu, t-Bu, or s-Bu; $R^{37}$ is Me, Et, i-Pr, n-Pr, n-Bu, t-Bu, or s-Bu; $R^{38}$ is H or Me, Et, i-Pr, n-Pr, n-Bu, t-Bu, or s-Bu; $R^{39}$ is H, Me, Et, i-Pr, n-Pr, n-Bu, t-Bu, or s-Bu; $R^{40}$ is H, Me, Et, i-Pr, n-Pr, n-Bu, t-Bu, or s-Bu; $R^{41}$ is H, Me, Et, i-Pr, n-Pr, n-Bu, t-Bu, or s-Bu; $R^{42}$ is H, Me, Et, i-Pr, n-Pr, n-Bu, t-Bu, or s-Bu; and x is 1 or 2.

In one embodiment, the invention provides a method for producing at least one E-macrocyclic product represented by Formula (I), wherein: $R'^2$ is H; n is 1; and m is 5, 6 or 7; and the E-macrocyclic product of Formula (III) is a twelve, thirteen, fourteen-membered ring with an E-selectivity of 95, or 98, or 99, or >99%; comprising: subjecting a diene substrate bearing two E-olefins represented by Formula (II) wherein R is Me; $R'^1$ is Me; $R'^2$ is H; n is 1; and m is 5, 6 or 7; to a ring-closing metathesis reaction in the presence of a stereoretentive ruthenium olefin metathesis catalyst represented by Formula (I), wherein: X is S; Y is S; Z is N; W is O; $R^1$ is Me or H; $R^2$ is Me or H; $R^3$ is H; $R^4$ is H; $R^5$ is H, F, Me, t-Bu or i-Pr; $R^6$ is H or t-Bu; $R^7$ is H, F or Me; $R^8$ is H, F or t-Bu; $R^9$ is H, F, Me, t-Bu or i-Pr; $R^{10}$ is H, F, Me, t-Bu or i-Pr; $R^{11}$ is H or t-Bu; $R^{12}$ is H, F or Me; $R^{13}$ is H, F or t-Bu; $R^{14}$ is F, Me, i-Pr, t-Bu or H; $R^{15}$ is H, Me, F, Br, I, Cl, or together with $R^{16}$ forms a naphthyl; $R^{16}$ is H, or together with $R^{15}$ forms a naphthyl; $R^{17}$ is H or together with $R^{18}$ forms a naphthyl, or a phenanthryl ring; $R^{18}$ is Cl, F, Br, I, 3,5-dichloro-phenyl, phenyl, t-Bu or together with $R^{17}$ forms a naphthyl, or a phenanthryl ring; $R^{19}$ is i-Pr, $R^{20}$ is H or phenyl; $R^{21}$ is H; $R^{22}$ is H, —C(O)$R^{25}$, —O$R^{26}$, CN, —N$R^{27}R^{28}$, $NO_2$, —$CF_3$, —S(O)$_x R^{29}$, —P(O)(OH)$_2$, —OP(O)(OH)$_2$, —S$R^{31}$; $R^{23}$ is H; $R^{24}$ is H; $R^{25}$ is OH, O$R^{30}$, N$R^{27}R^{28}$, Me, Et, or i-Pr; $R^{26}$ is H, Me, Et, i-Pr, n-Pr, n-Bu, t-Bu, or s-Bu; $R^{27}$ is H, Me, Et, i-Pr, n-Pr, n-Bu, t-Bu, or s-Bu; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, —N$R^{27}R^{28}$; $R^{30}$ is Me, Et, i-Pr, n-Pr, n-Bu, t-Bu, or s-Bu; and $R^{31}$ is H, Me, Et, i-Pr, n-Pr, n-Bu, t-Bu, or s-Bu.

In one embodiment, the invention provides a method for producing at least one E-macrocyclic product represented by Formula (III), wherein: $R'^2$ is H; n is 1; m is 5, 6 or 7; and the E-macrocyclic product of Formula (III) is a twelve, thirteen, fourteen-membered ring with an E-selectivity of 95, or 98, or 99, or >99%; comprising: subjecting a diene substrate bearing two E-olefins represented by Formula (II) wherein R is Me; $R'^1$ is Me; $R'^2$ is H; n is 1; and m is 5, 6 or 7; to a ring-closing metathesis reaction in the presence of a stereoretentive ruthenium olefin metathesis catalyst represented by Formula (I), wherein: X is S; Y is S; Z is N; W is O; $R^1$ is Me; $R^2$ is Me; $R^3$ is H; $R^4$ is H; $R^5$ is F; $R^6$ is H; $R^7$ is H or F; $R^8$ is H; $R^9$ is F; $R^{10}$ is F; $R^{11}$ is H; $R^{12}$ is H; $R^{13}$ is H; $R^{14}$ is F; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (III), wherein: $R'^2$ is H; n is 1; m is 5, 6 or 7; and the E-macrocyclic product of Formula (III) is a twelve, thirteen, fourteen-membered ring with an E-selectivity of 95, or 98, or 99, or >99%; comprising: subjecting a diene substrate bearing two E-olefins represented by Formula (II) wherein R is Me; $R'^1$ is Me; $R'^2$ is H; n is 1; and m is 5, 6 or 7; to a ring-closing metathesis reaction in the presence of a stereoretentive ruthenium olefin metathesis catalyst represented by Formula (I), wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr, $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (III), wherein: $R'^2$ is H; n is 3; m is 7; and the E-macrocyclic product of Formula (III) is a sixteen-membered ring with an E-selectivity of 95, or 98, or 99, or >99%; comprising: subjecting a diene substrate bearing one E-olefin and one terminal olefin represented by Formula (II) wherein R is Me; $R'^1$ is H; $R'^2$ is H; n is 3; and m is 7; to a ring-closing metathesis reaction in the presence of a stereoretentive ruthenium olefin metathesis catalyst represented by Formula (I), as defined herein.

In one embodiment, the invention provides a method for producing at least one E-macrocyclic product represented by Formula (II), wherein: $R'^2$ is H; n is 3; m is 7; and the E-macrocyclic product of Formula (III) is a sixteen-membered ring with an E-selectivity of 95, or 98, or 99, or >99%; comprising: subjecting a diene substrate bearing one E-olefin and one terminal olefin represented by Formula (II) wherein R is Me; $R'^1$ is H; $R'^2$ is H; n is 3; and m is 7; to a ring-closing metathesis reaction in the presence of a stereoretentive ruthenium olefin metathesis catalyst represented by Formula (I), wherein: X is S; Y is S; Z is N or C$R^{32}$; W is O, N$R^{33}$ or S; $R^1$ is Me, Et, i-Pr, n-Pr, n-Bu, t-Bu, s-Bu or H; $R^2$ is Me, Et, i-Pr, n-Pr, n-Bu, t-Bu, s-Bu or H; $R^3$ is H, Me, Et, i-Pr, n-Pr, n-Bu, t-Bu, or s-Bu; $R^4$ is H, Me, Et, i-Pr, n-Pr, n-Bu, t-Bu, or s-Bu; $R^5$ is H, F, Cl, Br, I, Me, Et, i-Pr, n-Pr, n-Bu, t-Bu, or s-Bu; $R^6$ is H, F, Cl, Br, I, Me, Et, i-Pr, n-Pr, n-Bu, t-Bu, or s-Bu; $R^7$ is H, F, Cl, Br, I, Me, Et, i-Pr, n-Pr, n-Bu, t-Bu, or s-Bu; $R^8$ is H, F, Cl, Br, I, Me, Et i-Pr, n-Pr, n-Bu, t-Bu, or s-Bu; $R^9$ is H, F, Cl, Br, I, Me, Et, i-Pr, n-Pr, n-Bu, t-Bu, or s-Bu; $R^{10}$ is H, F, Cl, Br, I, Me, Et, i-Pr, n-Pr, n-Bu, t-Bu, or s-Bu; $R^{11}$ is H, Me, F, Cl, Br, I, Et, i-Pr, n-Pr, n-Bu, t-Bu, or s-Bu; $R^{12}$ is H, F, Cl, Br, I, Me, Et, i-Pr, n-Pr, n-Bu, t-Bu, or s-Bu; $R^{13}$ is H, Me, F, Cl, Br, I, Et, n-Pr, i-Pr, n-Bu, t-Bu or s-Bu; $R^{14}$ is F, Cl, Br, I, Me, Et, i-Pr, n-Pr, n-Bu, t-Bu, s-Bu or H; $R^{15}$ is H, Me, Et, i-Pr, n-Pr, n-Bu, t-Bu, s-Bu, F, Br, I, Cl, or together with $R^{16}$ forms a naphthyl or a phenanthryl ring; $R^{16}$ is H, F, Cl, Br, I, or together with $R^{15}$ forms a naphthyl or a phenanthryl ring; $R^{17}$ is H, F, Cl, Br, I, or together with $R^{18}$ forms a naphthyl, or a phenanthryl ring; $R^{18}$ is H, Cl, F, Br, I, 3,5-dichloro-phenyl, phenyl, Me, Et, i-Pr, n-Pr, n-Bu, t-Bu, s-Bu or together with $R^{17}$ forms a naphthyl, or a phenanthryl; $R^{19}$ is H, phenyl, $C_{1-6}$ alkyl, —C($R^{34}$)($R^{35}$) COOR$^{36}$, —C($R^{34}$)($R^{35}$) C(O)H, —C($R^{34}$)($R^{35}$) C(O)R$^{37}$, —C($R^{34}$)($R^{35}$) CR$^{38}$(OR$^{39}$)(OR$^{40}$), —C($R^{34}$)($R^{35}$) C(O) NR$^{41}$R$^{42}$, —C($R^{34}$)($R^{35}$) C(O) NR$^{41}$OR$^{40}$; $R^{20}$ is H, F, Cl, Br, I, Me, Et, i-Pr, n-Pr, n-Bu, t-Bu, s-Bu, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, pyridine, piperidine, imidazole, indolizine, indazole, optionally substituted $C_{3-8}$ cycloalkyl, phenyl, naphthalene, or cyclohexene; $R^{21}$ is H, phenyl, Me, Et, i-Pr, n-Pr, n-Bu, t-Bu, s-Bu, —NR$^{27}$R$^{28}$ F, Cl, Br, or I; $R^{22}$ is H, Me, Et, i-Pr, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, pyridine, piperidine, imidazole, indolizine, indazole, cyclohexyl, phenyl, naphthalene, cyclohexene F, Cl, Br, or I; $R^{22}$ is H, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, or —SR$^{31}$; $R^{23}$ is H, F, Cl, Br, I, phenyl, Me, Et, i-Pr, n-Pr, n-Bu, t-Bu, or s-Bu; $R^{24}$ is H; $R^{24}$ is H, or Me; $R^{25}$ is OH, OR$^{30}$, NR$^{27}$R$^{28}$, Me, Et, or i-Pr; $R^{26}$ is H, Me, Et, i-Pr, n-Pr, n-Bu, t-Bu, or s-Bu; $R^{27}$ is H, Me, Et, or i-Pr, $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, or —NR$^{27}$R$^{23}$; $R^{30}$ is Me, Et, i-Pr, n-Pr, n-Bu, t-Bu, or s-Bu; $R^{31}$ is H, Me, Et, i-Pr, n-Pr, n-Bu, t-Bu, or s-Bu; $R^{32}$ is Me, Et, n-Pr or H; $R^{33}$ is H, Me, Et, Me, Et, i-Pr, n-Pr, n-Bu, t-Bu, s-Bu, or together with $R^{19}$ forms a morpholino, a thio-morpholino, a pyrrolidino, a piperidino, or a piperazino ring; $R^{34}$ is H, Me, Et, i-Pr, n-Pr, n-Bu, t-Bu, or s-Bu; $R^{35}$ is H, or Me, Et, i-Pr, n-Pr, n-Bu, t-Bu, or s-Bu; $R^{36}$ is H, Me, Et, i-Pr, n-Pr, n-Bu, t-Bu, or s-Bu; $R^{37}$ is Me, Et, i-Pr, n-Pr, n-Bu, t-Bu, or s-Bu; $R^{38}$ is H or Me, Et, i-Pr, n-Pr, n-Bu, t-Bu, or s-Bu; $R^{39}$ is H, Me, Et, i-Pr, n-Pr, n-Bu, t-Bu, or s-Bu; $R^{40}$ is H, Me, Et, i-Pr, n-Pr, n-Bu, t-Bu, or s-Bu; $R^{41}$ is H, Me, Et, i-Pr, n-Pr, n-Bu, t-Bu, or s-Bu; $R^{42}$ is H, Me, Et, i-Pr, n-Pr, n-Bu, t-Bu, or s-Bu; and x is 1 or 2.

In one embodiment, the invention provides a method for producing at least one E-macrocyclic product represented by Formula (III), wherein: $R'^2$ is H; n is 3; m is 7; and the E-macrocyclic product of Formula (III) is a sixteen-membered ring with an E-selectivity of 95, or 98, or 99, or >99%; comprising: subjecting a diene substrate bearing one E-olefin and one terminal olefin, represented by Formula (II) wherein R is Me; $R^{r1}$ is H; $R'^2$ is H; n is 3; and m is 7; to a ring-closing metathesis reaction in the presence of a stereoretentive ruthenium olefin metathesis catalyst represented by Formula (I), wherein: X is S; Y is S; Z is N; W is O; $R^1$ is Me or H; $R^2$ is Me or H; $R^3$ is H; $R^4$ is H; $R^5$ is H, F, Me, t-Bu or i-Pr; $R^6$ is H or t-Bu; $R^7$ is H, F or Me; $R^8$ is H, F or t-Bu; $R^9$ is H, F, Me, t-Bu or i-Pr, $R^{10}$ is H, F, Me, t-Bu or i-Pr; $R^{11}$ is H or t-Bu; $R^{12}$ is H, F or Me; $R^{13}$ is H, F or t-Bu; $R^{14}$ is F, Me, i-Pr, t-Bu or H; $R^{15}$ is H, Me, F, Br, I, Cl, or together with $R^{16}$ forms a naphthyl; $R^{16}$ is H, or together with $R^{15}$ forms a naphthyl; $R^{17}$ is H or together with $R^{18}$ forms a naphthyl, or a phenanthryl ring; $R^{18}$ is Cl, F, Br, I, 3,5-dichloro-phenyl, phenyl, t-Bu or together with $R^{17}$ forms a naphthyl, or a phenanthryl ring; $R^{19}$ is i-Pr; $R^{20}$ is H or phenyl; $R^{21}$ is H; $R^{22}$ is H, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP (O)(OH)$_2$, —SR$^{31}$; $R^{23}$ is H; $R^{24}$ is H; $R^{25}$ is OH, OR$^{30}$, NR$^{27}$R$^{28}$, Me, Et, or i-Pr; $R^{26}$ is H, Me, Et, i-Pr, n-Pr, n-Bu, t-Bu, or s-Bu; $R^{27}$ is H, Me, Et, i-Pr, n-Pr, n-Bu, t-Bu, or s-Bu; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, —NR$^{27}$R$^{28}$; $R^{30}$ is Me, Et, i-Pr, n-Pr, n-Bu, t-Bu, or s-Bu; and $R^{31}$ is H, Me, Et, i-Pr, n-Pr, n-Bu, t-Bu, or s-Bu.

In one embodiment, the invention provides a method for producing at least one E-macrocyclic product represented by Formula (III), wherein: $R'^2$ is H; n is 3; m is 7; and the E-macrocyclic product of Formula (II) is a sixteen-membered ring with an E-selectivity of 95, or 98, or 99, or >99%; comprising: subjecting a diene substrate bearing one E-olefin and one terminal olefin, represented by Formula (II) wherein R is Me; $R^{r1}$ is H; $R'^2$ is H; n is 3; and m is 7; to a ring-closing metathesis reaction in the presence of a stereoretentive ruthenium olefin metathesis catalyst represented by Formula (I), wherein: X is S; Y is S; Z is N; W is O; $R^1$ is Me; $R^2$ is Me; $R^3$ is H; $R^4$ is H; $R^5$ is F; $R^6$ is H; $R^7$ is H or F; $R^8$ is H; $R^9$ is F; $R^{10}$ is F; $R^{11}$ is H; $R^{12}$ is H; $R^{13}$ is H; $R^{14}$ is F; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (III), wherein: $R'^2$ is H; n is 3; m is 7; and the E-macrocyclic product of Formula (III) is a sixteen-membered ring with an E-selectivity of 95, or 98, or 99, or >99%; comprising: subjecting a diene substrate bearing one E-olefin and one terminal olefin, represented by Formula (II) wherein R is Me; $R^{r1}$ is H; $R'^2$ is H; n is 3; and m is 7; to a ring-closing metathesis reaction in the presence of a stereoretentive ruthenium olefin metathesis catalyst represented by Formula (I), wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (III), wherein: $R'^2$ is H; n is 5; m is 7; and the E-macrocyclic product of Formula (III) is a eighteen-membered ring with an E-selectivity of 95, or 98, or 99, or >99%; comprising: subjecting a diene substrate bearing two E-olefins represented by Formula (II) wherein R is Me; $R^{r1}$ is Me; $R'^2$ is H; n is 5; and m is 7; to a ring-closing metathesis reaction in the presence of a stereoretentive ruthenium olefin metathesis catalyst represented by Formula (I), as defined herein.

In one embodiment, the invention provides a method for producing at least one E-macrocyclic product represented by Formula (III), wherein: $R'^2$ is H; n is 5; m is 7; and the E-macrocyclic product of Formula (III) is a eighteen-membered ring with an E-selectivity of 95, or 98, or 99, or >99%; comprising: subjecting a diene substrate bearing two E-olefins represented by Formula (II) wherein R is Me; $R^{r1}$ is Me; $R'^2$ is H; n is 5; and m is 7; to a ring-closing metathesis reaction in the presence of a stereoretentive ruthenium olefin metathesis catalyst represented by Formula (I), wherein: X is S; Y is S; Z is N or CR$^{32}$; W is O, NR$^{33}$ or S; $R^1$ is Me, Et, i-Pr, n-Pr, n-Bu, t-Bu, s-Bu or H; $R^2$ is Me, Et, i-Pr, n-Pr, n-Bu, t-Bu, s-Bu or H; $R^3$ is H, Me, Et, i-Pr, n-Pr, n-Bu, t-Bu, or s-Bu; $R^4$ is H, Me, Et, i-Pr, n-Pr, n-Bu, t-Bu, or s-Bu; $R^5$ is H, F, Cl, Br, I, Me, Et, i-Pr, n-Pr, n-Bu, t-Bu, or s-Bu; $R^6$ is H, F, Cl, Br, I, Me, Et, i-Pr, n-Pr, n-Bu, t-Bu, or s-Bu; $R^7$ is H, F, Cl, Br, I, Me, Et, i-Pr, n-Pr, n-Bu, t-Bu, or s-Bu; $R^8$ is H, F, Cl, Br, I, Me, Et, i-Pr, n-Pr, n-Bu, t-Bu, or s-Bu; $R^9$ is H, F, Cl, Br, I, Me, Et, i-Pr, n-Pr, n-Bu, t-Bu, or s-Bu; $R^{10}$ is H, F, Cl, Br, I, Me, Et, i-Pr, n-Pr, n-Bu, t-Bu, or s-Bu; $R^{11}$ is H, Me, F, Cl, Br, I, Et, i-Pr, n-Pr, n-Bu, t-Bu, or s-Bu; $R^{12}$ is H, F, Cl, Br, I, Me, Et, i-Pr, n-Pr, n-Bu, t-Bu, or s-Bu; $R^{13}$ is H, Me, F, Cl, Br, I, Et, n-Pr, i-Pr, n-Bu, t-Bu or s-Bu; $R^{14}$ is F, Cl, Br, I, Me, Et, i-Pr, n-Pr, n-Bu, t-Bu, s-Bu or H; $R^{15}$ is H, Me, Et, i-Pr, n-Pr, n-Bu, t-Bu, s-Bu, F, Br, I, Cl, or together with $R^{16}$ forms a naphthyl or a phenanthryl ring; $R^{16}$ is H, F, Cl, Br, I, or together with $R^{15}$ forms a naphthyl or a phenanthryl ring; $R^{17}$ is H, F, Cl, Br, I, or together with $R^{18}$ forms a naphthyl, or a phenanthryl ring; $R^{18}$ is H, Cl, F, Br, I, 3,5-dichloro-phenyl, phenyl, Me, Et, i-Pr, n-Pr, n-Bu, t-Bu, s-Bu or together with $R^{17}$ forms a naphthyl, or a phenanthryl; $R^{19}$ is H, phenyl, $C_{1-6}$ alkyl, —$C(R^{34})(R^{35})$ $COOR^{36}$, —$C(R^{34})(R^{35})$ $C(O)H$, —$C(R^{34})(R^{35})$ $C(O)R^{37}$, —$C(R^{34})(R^{35})$ $CR^{38}(OR^{39})(OR^{40})$, —$C(R^{34})(R^{35})$ $C(O)NR^{41}R^{42}$, —$C(R^{34})(R^{35})$ $C(O)$ $NR^{41}OR^{40}$; $R^{20}$ is H, F, Cl, Br, I, Me, Et, i-Pr, n-Pr, n-Bu, t-Bu, s-Bu, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, pyridine, piperidine, imidazole, indolizine, indazole, optionally substituted $C_{3-8}$ cycloalkyl, phenyl, naphthalene, or cyclohexene; $R^{21}$ is H, phenyl, Me, Et, i-Pr, n-Pr, n-Bu, t-Bu, s-Bu, —$NR^{27}R^{28}$ F, Cl, Br, or I; $R^{22}$ is H, Me, Et, i-Pr, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, pyridine, piperidine, imidazole, indolizine, indazole, cyclohexyl, phenyl, naphthalene, cyclohexene F, Cl, Br, or I; $R^{22}$ is H, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, or —$SR^{31}$; $R^{23}$ is H, F, Cl, Br, I, phenyl, Me, Et, i-Pr, n-Pr, n-Bu, t-Bu, or s-Bu; $R^{24}$ is H; $R^{24}$ is H, or Me; $R^{25}$ is OH, $OR^{30}$, $NR^{27}R^{28}$, Me, Et, or i-Pr; $R^{26}$ is H, Me, Et, i-Pr, n-Pr, n-Bu, t-Bu, or s-Bu; $R^{27}$ is H, Me, Et, or i-Pr; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, or —$NR^{27}R^{28}$; $R^{30}$ is Me, Et, i-Pr, n-Pr, n-Bu, t-Bu, or s-Bu; $R^{31}$ is H, Me, Et, i-Pr, n-Pr, n-Bu, t-Bu, or s-Bu; $R^{32}$ is Me, Et, n-Pr or H; $R^{33}$ is H, Me, Et, Me, Et, i-Pr, n-Pr, n-Bu, t-Bu, s-Bu, or together with $R^{19}$ forms a morpholino, a thio-morpholino, a pyrrolidino, a piperidino, or a piperazino ring; $R^{34}$ is H, Me, Et, i-Pr, n-Pr, n-Bu, t-Bu, or s-Bu; $R^{35}$ is H, or Me, Et, i-Pr, n-Pr, n-Bu, t-Bu, or s-Bu; $R^{36}$ is H, Me, Et, i-Pr, n-Pr, n-Bu, t-Bu, or s-Bu; $R^{37}$ is Me, Et, i-Pr, n-Pr, n-Bu, t-Bu, or s-Bu; $R^{38}$ is H or Me, Et, i-Pr, n-Pr, n-Bu, t-Bu, or s-Bu; $R^{39}$ is H, Me, Et, i-Pr, n-Pr, n-Bu, t-Bu, or s-Bu; $R^{40}$ is H, Me, Et, i-Pr, n-Pr, n-Bu, t-Bu, or s-Bu; $R^{41}$ is H, Me, Et, i-Pr, n-Pr, n-Bu, t-Bu, or s-Bu; $R^{42}$ is H, Me, Et, i-Pr, n-Pr, n-Bu, t-Bu, or s-Bu; and x is 1 or 2.

In one embodiment, the invention provides a method for producing at least one E-macrocyclic product represented by Formula (III), wherein: $R^{r2}$ is H; n is 5; m is 7; and the E-macrocyclic product of Formula (III) is a eighteen-membered ring with an E-selectivity of 95, or 98, or 99, or >99%; comprising: subjecting a diene substrate bearing two E-olefins represented by Formula (II) wherein R is Me; $R^{r1}$ is Me; $R^{r2}$ is H; n is 5; and m is 7; to a ring-closing metathesis reaction in the presence of a stereoretentive ruthenium olefin metathesis catalyst represented by Formula (I), wherein: X is S; Y is S; Z is N; W is O; $R^1$ is Me or H; $R^2$ is Me or H; $R^3$ is H; $R^4$ is H; $R^5$ is H, F, Me, t-Bu or i-Pr; $R^6$ is H or t-Bu; $R^7$ is H, F or Me; $R^8$ is H, F or t-Bu; $R^9$ is H, F, Me, t-Bu or i-Pr, $R^{10}$ is H, F, Me, t-Bu or i-Pr; $R^{11}$ is H or t-Bu; $R^{12}$ is H, F or Me; $R^{13}$ is H, F or t-Bu; $R^{14}$ is F, Me, i-Pr, t-Bu or H; $R^{15}$ is H, Me, F, Br, I, Cl, or together with $R^{16}$ forms a naphthyl; $R^{16}$ is H, or together with $R^{15}$ forms a naphthyl; $R^{17}$ is H or together with $R^{18}$ forms a naphthyl, or a phenanthryl ring; $R^{18}$ is Cl, F, Br, I, 3,5-dichloro-phenyl, phenyl, t-Bu or together with $R^{17}$ forms a naphthyl, or a phenanthryl ring; $R^{19}$ is i-Pr; $R^{20}$ is H or phenyl; $R^{21}$ is H; $R^{22}$ is H, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$; $R^{23}$ is H; $R^{24}$ is H; $R^{25}$ is OH, $OR^{30}$, $NR^{27}R^{28}$, Me, Et, or i-Pr; $R^{26}$ is H, Me, Et, i-Pr, n-Pr, n-Bu, t-Bu, or s-Bu; $R^{27}$ is H, Me, Et, i-Pr, n-Pr, n-Bu, t-Bu, or s-Bu; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, —$NR^{27}R^{28}$; $R^{30}$ is Me, Et, i-Pr, n-Pr, n-Bu, t-Bu, or s-Bu; and $R^{31}$ is H, Me, Et, i-Pr, n-Pr, n-Bu, t-Bu, or s-Bu.

In one embodiment, the invention provides a method for producing at least one E-macrocyclic product represented by Formula (III), wherein: $R^{r2}$ is H; n is 5; m is 7; and the E-macrocyclic product of Formula (III) is a eighteen-membered ring with an E-selectivity of 95, or 98, or 99, or >99%; comprising: subjecting a diene substrate bearing two E-olefins represented by Formula (II) wherein R is Me; $R^{r1}$ is Me; $R^{r2}$ is H; n is 5; and m is 7; to a ring-closing metathesis reaction in the presence of a stereoretentive ruthenium olefin metathesis catalyst represented by Formula (I), wherein: X is S; Y is S; Z is N; W is O; $R^1$ is Me; $R^2$ is Me; $R^3$ is H; $R^4$ is H; $R^5$ is F; $R^6$ is H; $R^7$ is H or F; $R^8$ is H; $R^9$ is F; $R^{10}$ is F; $R^{11}$ is H; $R^{12}$ is H; $R^{13}$ is H; $R^{14}$ is F; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (III), wherein: $R^{r2}$ is H; n is 5; m is 7; and the E-macrocyclic product of Formula (III) is a eighteen-membered ring with an E-selectivity of 95, or 98, or 99, or >99%; comprising: subjecting a diene substrate bearing two E-olefins represented by Formula (II) wherein R is Me; $R^{r1}$ is Me; $R^{r2}$ is H; n is 5; and m is 7; to a ring-closing metathesis reaction in the presence of a stereoretentive ruthenium olefin metathesis catalyst represented by Formula (I), wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr, $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (III), wherein: $R^{r2}$ is H; n is 1; m is 7; and the E-macrocyclic product of Formula (III) is a fourteen-membered ring with an E-selectivity of 95, or 98, or 99, or >99%; comprising: subjecting a diene substrate bearing one E-olefin and one terminal olefin, represented by Formula (II) wherein R is Et; $R^{r1}$ is H; $R^{r2}$ is H; n is 1; and m is 7; to a ring-closing metathesis reaction in the presence of a stereoretentive ruthenium olefin metathesis catalyst represented by Formula (I), as defined herein.

In one embodiment, the invention provides a method for producing at least one E-macrocyclic product represented by Formula (III), wherein: $R^{r2}$ is H; n is 1; m is 7; and the E-macrocyclic product of Formula (III) is a fourteen-membered ring with an E-selectivity of 95, or 98, or 99, or >99%; comprising: subjecting a diene substrate bearing one E-olefin and one terminal olefin, represented by Formula (II) wherein R is Et; $R^{r1}$ is H; $R^{r2}$ is H; n is 1; and m is 7; to a ring-closing metathesis reaction in the presence of a stereoretentive ruthenium olefin metathesis catalyst represented by Formula (I), wherein: X is S; Y is S; Z is N or $CR^{32}$; W is O, $NR^{33}$ or S; $R^1$ is Me, Et, i-Pr, n-Pr, n-Bu, t-Bu, s-Bu or H; $R^2$ is Me, Et, i-Pr, n-Pr, n-Bu, t-Bu, s-Bu or H; $R^3$ is H, Me, Et, i-Pr, n-Pr, n-Bu, t-Bu, or s-Bu; $R^4$ is H, Me, Et, i-Pr, n-Pr, n-Bu, t-Bu, or s-Bu; $R^5$ is H, F, Cl, Br, I, Me, Et, i-Pr, n-Pr, n-Bu, t-Bu, or s-Bu; $R^6$ is H, F, Cl, Br, I, Me, Et, i-Pr, n-Pr, n-Bu, t-Bu, or s-Bu; $R^7$ is H, F, Cl, Br, I, Me, Et, i-Pr, n-Pr, n-Bu, t-Bu, or s-Bu; $R^8$ is H, F, Cl, Br, I, Me, Et, i-Pr, n-Pr, n-Bu, t-Bu, or s-Bu; $R^9$ is H, F, Cl, Br, I, Me, Et, i-Pr, n-Pr, n-Bu, t-Bu, or s-Bu; $R^{10}$ is H, F, Cl, Br, I, Me, Et, i-Pr, n-Pr, n-Bu, t-Bu, or s-Bu; $R^{11}$ is H, Me, F, Cl, Br, I, Et, i-Pr, n-Pr, n-Bu, t-Bu, or s-Bu; $R^{12}$ is H, F, Cl, Br, I, Me, Et, i-Pr, n-Pr, n-Bu, t-Bu, or s-Bu; $R^{13}$ is H, Me, F, Cl, Br, I, Et, n-Pr, i-Pr, n-Bu, t-Bu or s-Bu; $R^{14}$ is F, Cl, Br, I, Me, Et, i-Pr, n-Pr, n-Bu, t-Bu, s-Bu or H; $R^{15}$ is H, Me, Et, i-Pr, n-Pr, n-Bu, t-Bu, s-Bu, F, Br, I, Cl, or together with $R^{16}$ forms a naphthyl or a phenanthryl ring; $R^{16}$ is H, F, Cl, Br, I, or together with $R^{15}$ forms a naphthyl or a phenanthryl ring; $R^{17}$ is H, F, Cl, Br, I, or together with $R^{18}$ forms a naphthyl, or a phenanthryl ring; $R^{18}$ is H, Cl, F, Br, I, 3,5-dichloro-phenyl, phenyl, Me, Et, i-Pr, n-Pr, n-Bu, t-Bu, s-Bu or together with $R^{17}$ forms a naphthyl, or a phenanthryl; $R^{19}$ is H, phenyl, $C_{1-6}$ alkyl, —$C(R^{34})(R^{35})$ $COOR^{36}$, —$C(R^{34})(R^{35})$ $C(O)H$, —$C(R^{34})(R^{35})$ $C(O)R^{37}$, —$C(R^{34})(R^{35})$ $CR^{38}(OR^{39})(OR^{40})$, —$C(R^{34})(R^{35})$ $C(O)$ $NR^{41}R^{42}$, —$C(R^{34})(R^{35})$ $C(O)$ $NR^{41}OR^{40}$; $R^{20}$ is H, F, Cl, Br, I, Me, Et, i-Pr, n-Pr, n-Bu, t-Bu, s-Bu, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, pyridine, piperidine, imidazole, indolizine, indazole, optionally substituted $C_{3-8}$ cycloalkyl, phenyl, naphthalene, or cyclohexene; $R^{21}$ is H, phenyl, Me, Et, i-Pr, n-Pr, n-Bu, t-Bu, s-Bu, —$NR^{27}R^{28}$ F, Cl, Br, or I; $R^{22}$ is H, Me, Et, i-Pr, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, pyridine, piperidine, imidazole, indolizine, indazole, cyclohexyl, phenyl, naphthalene, cyclohexene F, Cl, Br, or I; $R^{22}$ is H, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, or —$SR^{31}$; $R^{23}$ is H, F, Cl, Br, I, phenyl, Me, Et, i-Pr, n-Pr, n-Bu, t-Bu, or s-Bu; $R^{24}$ is H; $R^{24}$ is H, or Me; $R^{25}$ is OH, $OR^{30}$, $NR^{27}R^{28}$, Me, Et, or i-Pr; $R^{26}$ is H, Me, Et, i-Pr, n-Pr, n-Bu, t-Bu, or s-Bu; $R^{27}$ is H, Me, Et, or i-Pr $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, or —$NR^{27}R^{28}$; $R^{30}$ is Me, Et, i-Pr, n-Pr, n-Bu, t-Bu, or s-Bu; $R^{31}$ is H, Me, Et, i-Pr, n-Pr, n-Bu, t-Bu, or s-Bu; $R^{32}$ is Me, Et, n-Pr or H; $R^{33}$ is H, Me, Et, Me, Et, i-Pr, n-Pr, n-Bu, t-Bu, s-Bu, or together with $R^{19}$ forms a morpholino, a thio-morpholino, a pyrrolidino, a piperidino, or a piperazino ring; $R^{34}$ is H, Me, Et, i-Pr, n-Pr, n-Bu, t-Bu, or s-Bu; $R^{35}$ is H, or Me, Et, i-Pr, n-Pr, n-Bu, t-Bu, or s-Bu; $R^{36}$ is H, Me, Et, i-Pr, n-Pr, n-Bu, t-Bu, or s-Bu; $R^{37}$ is Me, Et, i-Pr, n-Pr, n-Bu, t-Bu, or s-Bu; $R^{38}$ is H or Me, Et, i-Pr, n-Pr, n-Bu, t-Bu, or s-Bu; $R^{39}$ is H, Me, Et, i-Pr, n-Pr, n-Bu, t-Bu, or s-Bu; $R^{40}$ is H, Me, Et, i-Pr, n-Pr, n-Bu, t-Bu, or s-Bu; $R^{41}$ is H, Me, Et, i-Pr, n-Pr, n-Bu, t-Bu, or s-Bu; $R^{42}$ is H, Me, Et, i-Pr, n-Pr, n-Bu, t-Bu, or s-Bu; and x is 1 or 2.

In one embodiment, the invention provides a method for producing at least one E-macrocyclic product represented by Formula (III), wherein: $R'^2$ is H; n is 1; m is 7; and the E-macrocyclic product of Formula (III) is a fourteen-membered ring with an E-selectivity of 95, or 98, or 99, or >99%; comprising: subjecting a diene substrate bearing one E-olefin and one terminal olefin, represented by Formula (II) wherein R is Et; $R'^1$ is H; $R'^2$ is H; n is 1; and m is 7; to a ring-closing metathesis reaction in the presence of a stereoretentive ruthenium olefin metathesis catalyst represented by Formula (I), wherein: X is S; Y is S; Z is N; W is O; $R^1$ is Me or H; $R^2$ is Me or H; $R^3$ is H; $R^4$ is H; $R^5$ is H, F, Me, t-Bu or i-Pr; $R^6$ is H or t-Bu; $R^7$ is H, F or Me; $R^8$ is H, F or t-Bu; $R^9$ is H, F, Me, t-Bu or i-Pr, $R^{10}$ is H, F, Me, t-Bu or i-Pr, $R^{11}$ is H or t-Bu; $R^{12}$ is H, F or Me; $R^{13}$ is H, F or t-Bu; $R^{14}$ is F, Me, i-Pr, t-Bu or H; $R^{15}$ is H, Me, F, Br, I, Cl, or together with $R^{16}$ forms a naphthyl; $R^{16}$ is H, or together with $R^{15}$ forms a naphthyl; $R^{17}$ is H or together with $R^{18}$ forms a naphthyl, or a phenanthryl ring; $R^{18}$ is Cl, F, Br, I, 3,5-dichloro-phenyl, phenyl, t-Bu or together with $R^{17}$ forms a naphthyl, or a phenanthryl ring; $R^{19}$ is i-Pr; $R^{20}$ is H or phenyl; $R^{21}$ is H; $R^{22}$ is H, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$; $R^{23}$ is H; $R^{24}$ is H; $R^{25}$ is OH, $OR^{30}$, $NR^{27}R^{28}$, Me, Et, or i-Pr; $R^{26}$ is H, Me, Et, i-Pr, n-Pr, n-Bu, t-Bu, or s-Bu; $R^{27}$ is H, Me, Et, i-Pr, n-Pr, n-Bu, t-Bu, or s-Bu; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, —$NR^{27}R^{28}$; $R^{30}$ is Me, Et, i-Pr, n-Pr, n-Bu, t-Bu, or s-Bu; and $R^{31}$ is H, Me, Et, i-Pr, n-Pr, n-Bu, t-Bu, or s-Bu.

In one embodiment, the invention provides a method for producing at least one E-macrocyclic product represented by Formula (III), wherein: $R'^2$ is H; n is 1; m is 7; and the E-macrocyclic product of Formula (III) is a fourteen-membered ring with an E-selectivity of 95, or 98, or 99, or >99%; comprising: subjecting a diene substrate bearing one E-olefin and one terminal olefin, represented by Formula (II) wherein R is Et; $R'^1$ is H; $R'^2$ is H; n is 1; and m is 7; to a ring-closing metathesis reaction in the presence of a stereoretentive ruthenium olefin metathesis catalyst represented by Formula (I), wherein: X is S; Y is S; Z is N; W is O; $R^1$ is Me; $R^2$ is Me; $R^3$ is H; $R^4$ is H; $R^5$ is F; $R^6$ is H; $R^7$ is H or F; $R^8$ is H; $R^9$ is F; $R^{10}$ is F; $R^{11}$ is H; $R^{12}$ is H; $R^{13}$ is H; $R^{14}$ is F; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (III), wherein: $R'^2$ is H; n is 1; m is 7; and the E-macrocyclic product of Formula (III) is a fourteen-membered ring with an E-selectivity of 95, or 98, or 99, or >99%; comprising: subjecting a diene substrate bearing one E-olefin and one terminal olefin, represented by Formula (II) wherein R is Et; $R'^1$ is H; $R'^2$ is H; n is 1; and m is 7; to a ring-closing metathesis reaction in the presence of a stereoretentive ruthenium olefin metathesis catalyst represented by Formula (I), wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a method for producing at least one E-macrocyclic product represented by Formula (V), wherein: n is 1, 2, 3, 4, 5 or 6; m is 4, 5, 6, or 7; and the E-macrocyclic product of Formula (V) is a twelve, thirteen, fourteen, fifteen, sixteen or eighteen-membered ring with an E-selectivity of 95, or 98, or 99, or >99% o; comprising: subjecting a diene substrate bearing two E-olefins or bearing one E-olefin and one terminal olefin, represented by Formula (VI), wherein: a is 1, 2, 3, 4, 5 or 6; b is 4, 5, 6 or 7; $R^a$ is H, linear or branched $C_{1-12}$ alkyl; $R^b$ is H, linear or branched $C_{1-12}$ alkyl; and with the proviso that only one of $R^a$ and $R^b$ can be H; to a macrocyclic ring-closing metathesis reaction in the presence of a stereoretentive ruthenium olefin metathesis catalyst represented by Formula (I), as defined herein.

In one embodiment, the invention provides a method for producing at least one E-macrocyclic product represented by Formula (VII), wherein: c is 1, 2, 3, 4, 5 or 6; d is 4, 5, 6, or 7; and the E-macrocyclic product of Formula (VII) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (VIII), wherein: c is 1, 2, 3, 4, 5 or 6; d is 4, 5, 6 or 7; $R^c$ is H, linear or branched $C_{1-12}$ alkyl; $R^d$ is H, linear or branched $C_{1-12}$ alkyl; and with the proviso that only one of $R^c$ and $R^d$ can be H; to a macrocyclic ring-closing metathesis reaction in the presence of a stereoretentive ruthenium olefin metathesis catalyst represented by Formula (I), as defined herein.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees Celsius and pressure is at or near atmospheric. The examples are to be considered as not being limiting of the invention as described herein and are instead provided as representative examples of the catalyst compounds of the invention, of the methods that may be used in their preparation, and of the methods of using the inventive catalysts.

Unless otherwise specified, all manipulations were carried out under air-free conditions in dry glassware in a Vacuum Atmospheres Glovebox filled with $N_2$. General solvents were purified by passing through solvent purification columns. Commercially available substrates were used as received. All solvents and substrates were sparged with Ar before bringing into the glovebox and filtered over basic alumina (Brockmann I) prior to use.

Catalysts 2-4 (Ahmed, T. S.; Grubbs, R. H. *J. Am. Chem. Soc.* 2017, 139 (4), 1532), trans-3-penten-1-ol, (Patel, H. H.; Sigman, M. S. *J Am. Chem. Soc.* 2015, 137 (10), 3462), trans-4-hexen-1-ol (Denmark, S. E.; Forbes, D. C.; Hays, D. S.; DePue, J. S.; Wilde, R. G. *J. Org. Chem.* 1996, 60, 1391), 5-heptyn-1-ol (Hotling, S.; Haberlag, B.; Tamm, M.; Collatz, J.; Mack, P.; Steidle, J. L. M.; Vences, M.; Schulz, S. *Chem. Eur. J.* 2014, 20, 3183), 6-octyn-1-ol (De Medeiros, E. F.; Herbert, J. M.; Taylorw, R. J. K. *Tetrahedron Letters.* 1990, 31(41), 5843), 7-nonyn-1-ol (Robinson, J. A.; Flohr, H.; Kempe, U. M.; Panhorst, W.; Rétey, J. *Liebigs Annalen der Chemie,* 1983, 2, 181), and 10-dodecyn-1-ol (Cryle, M. J.; Hayes, P. Y.; De Voss, J. J. *Chem. Eur. J.* 2012, 18, 15994) were synthesized according to known literature procedures.

An array of diene substrates bearing two E-olefins or bearing one E-olefin and one terminal olefin, were synthesized from internal alkyne starting materials which were reduced by $Li/NH_3$ or $LiAlH_4$, according to Scheme 3. Subsequent Jones oxidation was used to generate the carboxylate moiety of the desired ester product. EDC coupling of this carboxylic acid with the corresponding alcohol gave the desired substrate in a scalable synthesis.

Scheme 3 Synthesis of diene substrates bearing two E-olefins.

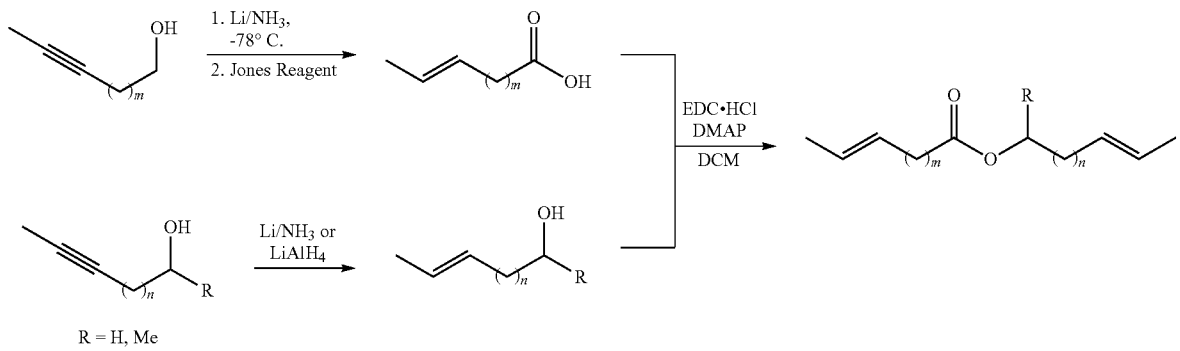

R = H, Me

The starting materials used for the synthesis of the diene substrate bearing two E-olefins or bearing one E-olefin and one terminal olefin, are as shown in Table 2:

TABLE 2

| Name | Structure | CAS number |
| --- | --- | --- |
| trans-4-hexen-2-ol | | [CAS 54560-70-2] |
| trans-7-nonen-1-ol | | [CAS 31502-20-2] |
| trans-7-nonenoic acid | | [CAS 31502-24-6] |
| 8-decyn-1-ol | HO~~~~~≡ | [CAS 274675-61-5] |
| trans-8-decen-1-ol | HO~~~~~= | [CAS 83799-68-2] |
| trans-8-decenoic acid | HO-C(=O)~~~~~= | [CAS 85484-88-4] |
| 9-undecyn-1-ol | HO~~~~~≡ | [CAS 177961-61-4] |

TABLE 2-continued

| Name | Structure | CAS number |
|---|---|---|
| trans-9-undecen-1-ol | HO~~~~~~~~~/ | [CAS 37973-86-7] |
| trans-9-undecenoic acid | HOOC~~~~~~/ | [CAS 37973-84-5] |
| trans-10-dodecen-1-ol | HO~~~~~~~~~/ | [CAS 83799-68-2] |
| trans-10-dodecenoic acid | HOOC~~~~~~~/ | [CAS 85484-88-4] |
| trans-5-hepten-1-ol | HO~~~~/ | [CAS 25143-94-6] |
| trans-3-hexen-1-ol | HO~~~/ | [CAS 928-97-2] |
| trans-3-penten-1-ol | HO~~/ | [CAS 764-37-4] |
| trans-4-hexen-1-ol | HO~~~/ | [CAS 928-92-7] |
| undecenoyl chloride | CH2=CH-(CH2)8-COCl | [CAS 38460-95-6] |

Using the diene substrates, presented herein, a variety of macrocyclic lactones were synthesized, ranging in size from 12- to 18-membered rings. Starting materials for the dienes described below, were synthesized according to the procedures found in the supporting information of *Chem. Sci.*, 2018, 9, 3580-3583 (Tonia S. Ahmed, T. S.; Montgomery T. P.; Grubbs R. H.). Spectra were analyzed using MestReNova Ver. 8.1.2. $^1$H and $^{13}$C NMR characterization data were obtained on a Bruker 400 with Prodigy broadband cryoprobe and referenced to residual protio-solvent.

High-resolution mass spectrometry (HRMS) was performed using FAB+ ionization on a JEOL MSRoute mass spectrometer. Some accurate masses were determined by electrospray ionization, in the positive ion mode, using a Waters LCT Premier XE time-of-flight mass spectrometer.

The following abbreviations are used herein:
RT or r.t. room temperature
CDCl$_3$ deuterated chloroform
THF tetrahydrofuran
HCl hydrochloric acid
NaOH sodium hydride
MgSO$_4$ magnesium sulfate
Et$_2$O diethyl ether
NaHCO$_3$ sodium bicarbonate
NH$_4$Cl ammonium chloride
t-BuOH tert-butylalcohol
H$_2$SO$_4$ sulfuric acid
KOtBu potassium tert-butoxide
DMSO dimethylsulfonamido
Na$_2$SO$_4$ sodium sulfate
DCM dichloromethane
DMAP 4-dimethylaminopyridine
EDC hydrochloride/EDC.HCl N-(3-Dimethylaminopropyl)-N'-ethylcarbodiimide hydrochloride
Jones reagent chromium trioxide, sulfuric acid dissolved in acetone and water
Li lithium
NH$_3$ ammonia
LiNH$_4$Cl lithium ammonium chloride

EXAMPLE 1

Synthesis of (E)-hex-3-en-1-yl undec-10-enoate

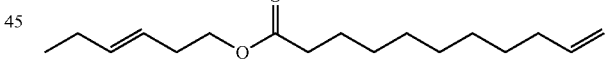

To a round-bottom flask charged with a stir bar were added 20 mL dichloromethane, undecenoyl chloride (2.37 mL, 11.0 mmol), and pyridine (0.89 mL, 11.0 mmol). Trans-3-hexen-1-ol (1.22 mL, 10.0 mmol) was then added dropwise at 0° C. The reaction mixture was brought to room temperature and stirred for 4 h. The reaction mixture was extracted with 1M aq. HCl (200 mL) and saturated aq. NaHCO$_3$ (200 mL). The organic layer was dried over anhydrous MgSO$_4$, filtered, and solvents were removed in vacuo. The product was purified by column chromatography on silica gel (5:95 Et$_2$O: pentane) to yield a colorless oil (2.53 g, 95% yield).

$^1$H NMR (400 MHz, Chloroform-d$_1$) δ 5.81 (ddt, J=16.9, 10.1, 6.7 Hz, 1H), 5.55 (dtt, J=15.3, 6.3, 1.3 Hz, 1H), 5.36 (dtt, J=15.2, 6.8, 1.5 Hz, 1H), 4.99 (dq, J=17.1, 1.7 Hz, 1H), 4.93 (ddt, J=10.2, 2.2, 1.2 Hz, 1H), 4.07 (t, J=6.9 Hz, 2H), 2.36-2.24 (m, 4H), 2.12-1.95 (m, 4H), 1.68-1.59 (m, 2H), 1.41-1.33 (m, 2H), 1.32-1.22 (m, 8H), 0.96 (t, J=7.4 Hz, 3H).

$^{13}$C NMR (101 MHz, CDCl$_3$) δ 174.04, 139.33, 135.14, 124.24, 114.28, 64.04, 34.52, 33.94, 32.13, 29.44, 29.36, 29.27, 29.21, 29.04, 25.77, 25.15, 13.89.

HRMS (EI+): [M]$^+$ C$_{17}$H$_{30}$O$_2$ Calculated—266.2246, Found—266.2239.

EXAMPLE 2

Synthesis of (E)-(E)-hex-4-ea-1-yl non-7-enoate

7

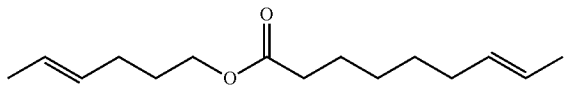

To a vial charged with a stir bar were added trans-7-nonenoic acid (143.7 mg, 0.9198 mmol), DMAP (23.0 mg, 0.184 mmol), EDC hydrochloride (352.1 mg, 1.840 mmol), and 7.5 mL dry dichloromethane under argon atmosphere. Trans-4-hexen-1-ol (216 µL, 1.840 mmol) was added, and the reaction was stirred for 3 h. The reaction mixture was quenched with a solution of 1 M aq. HCl (15 mL) after which, the product was extracted with DCM (4×15 mL). This organic phase was dried over MgSO$_4$, filtered, and concentrated in vacuo. The product was purified by column chromatography (5:95 Et$_2$O: pentane) to yield the product as a colorless oil (201.7 mg, 92% yield).

$^1$H NMR (400 MHz, Chloroform-d$_1$) δ 5.52-5.36 (m, 4H), 4.08 (t, J=6.7 Hz, 2H), 2.31 (t, J=7.5 Hz, 2H), 2.11-2.03 (m, 2H), 1.99 (dddd, J=8.7, 6.5, 3.0, 1.3 Hz, 2H), 1.74-1.59 (m, 10H), 1.42-1.26 (m, 4H).

$^{13}$C NMR (101 MHz, CDCl$_3$) δ 173.95, 131.28, 129.97, 125.81, 124.86, 63.78, 34.37, 32.39, 29.21, 28.88, 28.66, 28.47, 24.91, 17.94, 17.93.

HRMS (EI+): [M]$^+$ C$_{15}$H$_{26}$O$_2$ Calculated—238.1933, Found—238.1935.

EXAMPLE 3

Synthesis of(E)-(E)-hex-4-en-2-yl dec-8-enoate

15

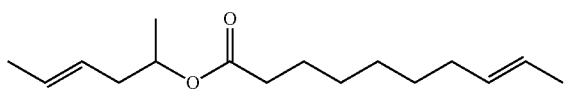

To a vial charged with a stir bar were added trans-8-decenoic acid (47.0 mg, 0.276 mmol), DMAP (6.74 mg, 0.0552 mmol), EDC hydrochloride (105.8 mg, 0.5520 mmol), and 2.3 mL dry dichloromethane under argon atmosphere. Trans-4-hexen-2-ol (55.3 mg, 0.552 mmol) was added, and the reaction was stirred for 3 h at ambient temperature. The reaction mixture was quenched with a solution of 1 M aq. HCl (10 mL) after which, the product was extracted with DCM (4×10 mL). The organic extracts were combined, dried over MgSO$_4$, filtered, and concentrated in vacuo. The product was purified by column chromatography (5:95 Et$_2$O: pentane) to yield the product as a colorless oil (47 mg, 67% yield).

$^1$H NMR (400 MHz, Chloroform-d$_1$) δ 5.54-5.43 (m, 1H), 5.42-5.29 (m, 3H), 4.90 (h, J=6.3 Hz, 1H), 2.30-2.22 (m, 3H), 2.22-2.12 (m, 1H), 2.00-1.90 (m, 2H), 1.69-1.55 (m, 8H), 1.39-1.24 (m, 6H), 1.18 (d, J=6.3 Hz, 3H).

$^{13}$C NMR (101 MHz, CDCl$_3$) δ 173.54, 131.60, 128.33, 126.29, 124.83, 70.39, 39.26, 34.86, 32.65, 29.54, 29.14, 28.94, 25.20, 19.62, 18.15, 18.08.

HRMS (EI+): [M]$^+$ C$_{16}$H$_{28}$O$_2$ Calculated—252.2089, Found—252.2074.

EXAMPLE 4

Synthesis of (E)-(E)-pent-3-en-1-yl undec-9-enoate

16

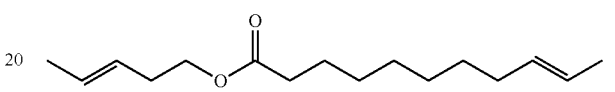

To a vial charged with a stir bar were added trans-9-undecenoic acid (53.4 mg, 0.290 mmol), DMAP (7.1 mg, 0.0580 mmol), EDC hydrochloride (111.1 mg, 0.580 mmol), and 2.3 mL dry dichloromethane under argon atmosphere. Trans-3-penten-1-ol (59.3 µL, 0.580 mmol) was added, and the reaction mixture was stirred for 3 h. The reaction mixture was quenched with a solution of 1M aq. HCl (5 mL) after which, the product was extracted with DCM (4×5 mL). This organic phase was dried over MgSO$_4$, filtered, and concentrated in vacuo. The product was purified by column chromatography (5:95 Et$_2$O: pentane) to yield the product as a colorless oil (65.7 mg, 90% yield).

$^1$H NMR (400 MHz, Chloroform-d$_1$) δ 5.60-5.31 (m, 1H), 4.06 (t, J=6.9 Hz, 1H), 2.36-2.22 (m, 1H), 1.99-1.89 (m, 1H), 1.72-1.51 (m, 2H), 1.39-1.23 (m, 2H).

$^{13}$C NMR (101 MHz, CDCl$_3$) δ 174.04, 131.69, 127.97, 126.52, 124.76, 64.00, 34.51, 32.70, 32.15, 29.67, 29.28, 29.24, 29.11, 25.14, 18.14, 18.08.

HRMS (EI+): [M]$^+$ C$_{16}$H$_{28}$O$_2$ Calculated—252.2089, Found—252.2095.

EXAMPLE 5

Synthesis of (E)-(E)-hex-4-en-1-yl undec-9-enoate

17

To a vial charged with a stir bar were added trans-9-undecenoic acid (51.4 mg, 0.280 mmol), DMAP (6.8 mg, 0.0560 mmol), EDC hydrochloride (106.9 mg, 0.560 mmol), and 2.2 mL dry dichloromethane under argon atmosphere. Trans-4-hexen-1-ol (65.6 µL, 0.560 mmol) was added, and the reaction was stirred for 3 h. The reaction mixture was quenched with a solution of 1M aq. HCl (5 mL) after which, the product was extracted with DCM (4×5 mL). This organic phase was dried over MgSO$_4$, filtered, and concentrated in vacuo. The product was purified by column chromatography (5:95 Et$_2$O: pentane) to yield the product as a colorless oil (68.3 mg, 92% yield).

$^1$H NMR (400 MHz, Chloroform-d$_1$) δ 5.46-5.25 (m, 4H), 3.99 (t, J=6.7 Hz, 2H), 2.27-2.15 (m, 2H), 1.97 (tdd, J=7.6, 5.9, 1.5 Hz, 2H), 1.92-1.85 (m, 2H), 1.65-1.49 (m, 10H), 1.32-1.13 (m, 8H).

$^{13}$C NMR (101 MHz, CDCl$_3$) δ 174.12, 131.69, 130.10, 125.93, 124.76, 63.90, 34.53, 32.70, 29.66, 29.27, 29.26, 29.11, 29.02, 28.60, 25.15, 18.08, 18.06.

HRMS (EI+): [M]$^+$ C$_{17}$H$_{30}$O$_2$ Calculated—266.2237, Found—266.2246.

EXAMPLE 6

Synthesis of (E)-(E)-pent-3-en-1-yl dodec-10-enoate

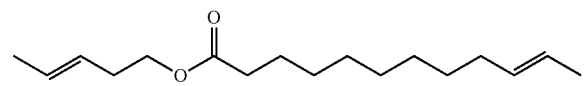

18

To a vial charged with a stir bar were added trans-10-dodecenoic acid (45.8 mg 0.231 mmol), DMAP (5.6 mg, 0.0462 mmol), EDC hydrochloride (88.6 mg, 0.462 mmol), and 1.8 mL dry dichloromethane under argon atmosphere. Trans-3-penten-1-ol (47.3 μL, 0.462 mmol) was added, and the reaction was stirred for 3 h. The reaction mixture was quenched with a solution of 1M aq. HCl (5 mL) after which, the product was extracted with DCM (4×5 mL). This organic phase was dried over MgSO$_4$, filtered, and concentrated in vacuo. The product was purified by column chromatography (5:95 Et$_2$O: pentane) to yield the product as a colorless oil (51.4 mg, 84% yield).

$^1$H NMR (400 MHz, Chloroform-d$_1$) δ 5.60-5.29 (m, 4H), 4.06 (t, J=6.9 Hz, 2H), 2.37-2.22 (m, 4H), 1.95 (dtt, J=7.9, 5.1, 1.5 Hz, 2H), 1.72-1.56 (m, 8H), 1.40-1.24 (m, 10H).

$^{13}$C NMR (101 MHz, CDCl$^3$) δ 174.05, 131.76, 127.98, 126.53, 124.73, 64.01, 34.52, 32.74, 32.16, 29.73, 29.48, 29.39, 29.30, 29.28, 29.26, 25.16, 18.16, 18.10.

HRMS (EI+): [M]$^+$ C$_{17}$H$_{30}$O$_2$ Calculated—266.2237, Found—266.2261.

EXAMPLE 7

Synthesis of (E)-(E)-hex-4-en-1-yl dodec-10-enoate

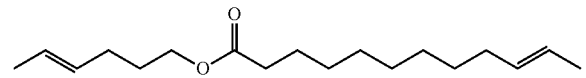

19

To a vial charged with a stir bar were added trans-10-dodecenoic acid (45.6 mg, 0.230 mmol), DMAP (5.6 mg, 0.0460 mmol), EDC hydrochloride (88.2 mg, 0.460 mmol), and 1.4 mL dry dichloromethane under argon atmosphere. Trans-4-hexen-1-ol (41.3 mg, 0.460 mmol) was added, and the reaction was stirred for 3 h. The reaction mixture was quenched with a solution of 1M aq. HCl (5 mL) after which, the product was extracted with DCM (4×5 mL). This organic phase was dried over MgSO$_4$, filtered, and concentrated in vacuo. The product was purified by column chromatography (5:95 Et$_2$O: pentane) to yield the product as a colorless oil (47.2 mg, 73% yield).

$^1$H NMR (400 MHz, Chloroform-d$_1$) δ 5.53-5.32 (m, 4H), 4.05 (t, J=6.7 Hz, 2H), 2.28 (t, J=7.5 Hz, 2H), 2.04 (dtd, J=7.9, 6.1, 1.5 Hz, 2H), 1.98-1.91 (m, 2H), 1.73-1.52 (m, 11H), 1.33-1.22 (m, 12H).

$^{13}$C NMR (101 MHz, CDCl$_3$) δ 174.13, 131.76, 130.11, 125.93, 124.72, 63.90, 34.54, 32.73, 29.72, 29.47, 29.38, 29.29, 29.26, 29.02, 28.60, 25.16, 18.09, 18.06.

HRMS (EI+): [M]$^+$ C$_{18}$H$_{32}$O$_2$ Calculated—280.2402, Found—280.2379.

EXAMPLE 8

Synthesis of (EE)-hept-5-en-1-yl dodec-10-enoate
CAS [152291-15-1]

20

To a vial charged with a stir bar was added trans-10-dodecenoic acid (35.9 mg, 0.181 mmol), DMAP (4.4 mg, 0.0362 mmol), EDC hydrochloride (69.4 mg, 0.362 mmol), and 1.4 mL dry dichloromethane under argon atmosphere. Trans-5-hepten-1-ol (41.3 mg, 0.362 mmol) was added, and the reaction was stirred for 3 h. The reaction mixture was quenched with a solution of 1M aq. HCl (5 mL) after which, the product was extracted with DCM (4×5 mL). This organic phase was dried over MgSO$_4$, filtered, and concentrated in vacuo. The product was purified by column chromatography (5:95 Et$_2$O: pentane) to yield the product as a colorless oil (41.0 mg, 77% yield). The NMR data corresponds to the literature data.

EXAMPLE 9

Synthesis of (E)-(E)-non-7-en-1-yl dodec-10-enoate

21

To a vial charged with a stir bar was added trans-10-dodecenoic acid (35.9 mg, 0.188 mmol), DMAP (4.6 mg, 0.0376 mmol), EDC hydrochloride (72.1 mg, 0.376 mmol), and 1.5 mL dry dichloromethane under argon atmosphere. Trans-7-nonen-1-ol (53.5 mg, 0.376 mmol) was added, and the reaction was stirred for 3 h. The reaction mixture was quenched with a solution of 1M aq. HCl (5 mL) after which, the product was extracted with DCM (4×5 mL). This organic phase was dried over MgSO$_4$, filtered, and concentrated in vacuo. The product was purified by column chromatography (5:95 Et$_2$O: pentane) to yield the product as a colorless oil (42.4 mg, 70% yield).

$^1$H NMR (400 MHz, Chloroform-d$_1$) δ 5.41 (ddt, J=5.0, 3.7, 1.7 Hz, 4H), 4.05 (t, J=6.7 Hz, 2H), 2.28 (t, J=7.5 Hz, 2H), 2.03-1.88 (m, 4H), 1.69-1.54 (m, 10H), 1.34-1.23 (m, 16H).

$^{13}$C NMR (101 MHz, CDCl$_3$) δ 174.16, 131.76, 131.54, 124.89, 124.71, 64.51, 34.55, 32.74, 32.62, 29.72, 29.59, 29.48, 29.38, 29.30, 29.26, 28.90, 28.76, 25.96, 25.17, 18.09.

HRMS (EI+): [M]$^+$ C$_{21}$H$_{38}$O$_2$ Calculated—322.2872, Found—322.2896.

EXAMPLE 10

Synthesis of (E)-oxacyclododec-8-en-2-one

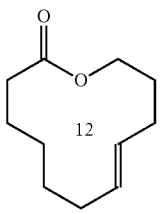

In an $N_2$-filled glovebox, (E)-(E)-hex-4-en-1-yl non-7-enoate 7 (20.0 mg, 83.9 μmol) and 15.8 mL THF were added to a vial charged with a stir bar. A solution of catalyst (6.3 μmol) in 1 mL of THF was then added to this mixture. The vial was loosely capped, and the reaction was stirred at 35° C. for the reported amount of time. The vial was taken out of the glovebox and quenched with 0.5 mL butyl vinyl ether. Solvents were removed in vacuo, and the product was purified with column chromatography on silica gel (1:49 $Et_2O$: pentane) to yield the product as a colorless oil (7.2 mg, 47% yield with 2; 9.1 mg, 60% yield with 4).

$^1$H NMR (400 MHz, Chloroform-$d_1$) δ 5.50 (dtt, J=15.3, 7.1, 1.3 Hz, 1H), 5.24-5.10 (m, 1H), 4.14-4.04 (m, 2H), 2.36-2.26 (m, 2H), 2.24-2.18 (m, 2H), 2.14-2.07 (m, 2H), 1.84-1.76 (m, 2H), 1.55 (tdd, J=9.6, 8.5, 4.3, 2.4 Hz, 2H), 1.48-1.39 (m, 2H), 1.28-1.19 (m, 2H).

$^{13}$C NMR (101 MHz, CDCl$_3$) δ 173.92, 133.38, 127.22, 66.38, 35.35, 32.60, 29.67, 28.12, 25.16, 24.99, 21.10.

HRMS (EI+): [M]$^+$ $C_{11}H_{18}O_2$ Calculated—182.1307, Found—182.1308.

EXAMPLE 11

Synthesis of (E)-12-methyloxacyclododec-9-en-2-one

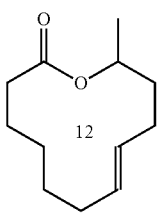

In an $N_2$-filled glovebox, (E)-hex-4-en-2-yl (E)-dec-8-enoate 15 (20.0 mg, 79.2 μmol) and 14.8 mL THF were added to a vial charged with a stir bar. A solution of catalyst (5.9 μmol) in 1 mL of THF was then added to this mixture. The vial was loosely capped, and the reaction was stirred at 35° C. for the reported amount of time. The vial was taken out of the glovebox and quenched with 0.5 mL butyl vinyl ether. Solvents were removed in vacuo, and the product was purified with column chromatography on silica gel (1:49 $Et_2O$: pentane) to yield the product as a colorless oil (9.4 mg, 61% yield with 2; 12.4 mg, 80% yield with 4).

$^1$H NMR (400 MHz, Chloroform-$d_1$) δ 5.36-5.21 (m, 2H), 5.16 (dqd, J=11.2, 6.3, 2.9 Hz, 1H), 2.37 (ddd, J=14.1, 11.5, 4.0 Hz, 1H), 2.33-2.27 (m, 1H), 2.23 (ddd, J=14.0, 5.5, 4.5 Hz, 1H), 2.20-2.06 (m, 2H), 2.03-1.91 (m, 1H), 1.88-1.75 (m, 1H), 1.57-1.46 (m, 3H), 1.46-1.32 (m, 2H), 1.24 (d, J=6.3 Hz, 3H), 1.21-1.08 (m, 2H).

$^{13}$C NMR (101 MHz, CDCl$_3$) δ 173.58, 133.55, 127.16, 68.63, 41.09, 33.04, 30.34, 25.04, 24.74, 24.33, 23.27, 20.70.

HRMS (EI+): [M]$^+$ $C_{12}H_{20}O_2$ Calculated—196.1463, Found—196.1451.

EXAMPLE 12

Synthesis of (E)-oxacyclotridec-10-en-2-one

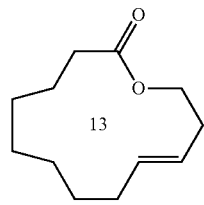

In an $N_2$-filled glovebox, (E)-(E)-pent-3-en-1-yl undecen-9-enoate 16 (22.6 mg, 89.7 μmol) and 17.0 mL THF were added to a vial charged with a stir bar. A solution of catalyst (6.7 μmol) in 1 mL of THF was then added to this mixture. The vial was loosely capped, and the reaction was stirred at 35° C. for the reported amount of time. The vial was taken out of the glovebox and quenched with 0.5 mL butyl vinyl ether. Solvents were removed in vacuo, and the product was purified with column chromatography on silica gel (1:49 $Et_2O$: pentane) to yield the product as a colorless oil (10.0 mg, 57% yield with 2; 13.2 mg, 75% yield with 4).

$^1$H NMR (400 MHz, Chloroform-$d_1$) δ 5.56 (dtt, J=15.6, 7.1, 1.3 Hz, 1H), 5.34 (dtt, J=15.1, 6.9, 1.3 Hz, 1H), 4.18-4.11 (m, 2H), 2.40-2.24 (m, 4H), 2.02 (dddd, J=10.5, 5.9, 2.2, 1.1 Hz, 2H), 1.72-1.60 (m, 2H), 1.42 (dq, J=5.7, 2.7 Hz, 2H), 1.38-1.23 (m, 6H).

$^{13}$C NMR (101 MHz, CDCl$_3$) δ 174.24, 134.87, 126.58, 63.06, 34.08, 32.73, 32.14, 27.52, 27.51, 27.43, 27.09, 24.33.

HRMS (EI+): [M]$^+$ $C_{12}H_{20}O_2$ Calculated—196.1463. Found—196.1488.

EXAMPLE 13

Synthesis of (E)-oxacyclotetradec-11-en-2-one

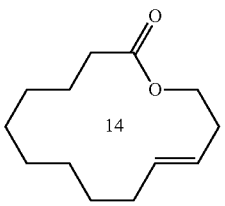

In an N$_2$-filled glovebox, (E)-(E)-pent-3-en-1-yl dodecen-10-enoate 18 (20.8 mg, 78.1 µmol) and 14.6 mL THF were added to a vial charged with a stir bar. A solution of catalyst (5.8 µmol) in 1 mL of THF was then added to this mixture. The vial was loosely capped, and the reaction was stirred at 35° C. for the reported amount of time. The vial was taken out of the glovebox and quenched with 0.5 mL butyl vinyl ether. Solvents were removed in vacuo, and the product was purified with column chromatography on silica gel (1:49 Et$_2$O: pentane) to yield the product as a colorless oil (9.5 mg, 58% yield with 2; 10.6 mg, 65% yield with 4).

$^1$H NMR (400 MHz, Chloroform-d$_1$) δ 5.55-5.27 (m, 2H), 4.16-4.07 (m, 2H), 2.41-2.31 (m, 4H), 2.05-1.95 (m, 2H), 1.65-1.53 (m, 2H), 1.45-1.17 (m, 10H).

$^{13}$C NMR (101 MHz, CDCl$_3$) δ 174.22, 132.98, 127.93, 64.48, 35.25, 32.01, 31.42, 26.79, 26.29, 25.99, 25.77, 24.00, 23.92.

HRMS (EI+): [M]$^+$ C$_{13}$H$_{22}$O$_2$ Calculated—210.1620, Found—210.1592.

EXAMPLE 14

Synthesis of (E)-oxacyclotetradec-10-en-2-one

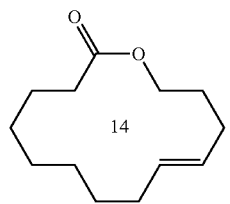

In an N$_2$-filled glovebox, (E)-(E)-hex-4-en-1-yl undecen-9-enoate 17 (24.4 mg, 91.6 µmol) and 17.3 mL THF were added to a vial charged with a stir bar. A solution of catalyst (6.9 µmol) in 1 mL of THF was then added to this mixture. The vial was loosely capped, and the reaction was stirred at 35° C. for the reported amount of time. The vial was taken out of the glovebox and quenched with 0.5 mL butyl vinyl ether. Solvents were removed in vacuo, and the product was purified with column chromatography on silica gel (1:49 Et$_2$O: pentane) to yield the product as a colorless oil (11.5 mg, 60% yield with 2; 12.9 mg, 67% yield with 4).

$^1$H NMR (400 MHz, Chloroform-d$_1$) δ 5.51 (dtt, J=15.1, 7.0, 1.3 Hz, 1H), 5.37 (dtt, J=15.2, 7.0, 1.3 Hz, 1H), 4.17-4.07 (m, 2H), 2.36-2.30 (m, 2H), 2.22 (dddd, J=11.0, 5.8, 2.4, 1.2 Hz, 2H), 2.13-2.01 (m, 2H), 1.80-1.63 (m, 4H), 1.46-1.37 (m, 2H), 1.34-1.25 (m, 6H).

$^{13}$C NMR (101 MHz, CDCl$_3$) δ 174.41, 130.76, 130.54, 64.94, 33.14, 31.55, 31.05, 28.31, 27.19, 26.77, 26.66, 25.11, 24.22.

HRMS (EI+): [M]$^+$ C$_{13}$H$_{22}$O$_2$ Calculated—210.1620, Found—210.1614.

EXAMPLE 15

Synthesis of (E)-oxacyclopentadec-11-en-2-one

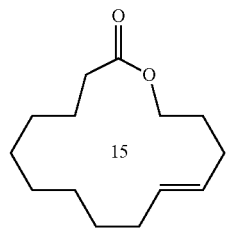

In an N$_2$-filled glovebox, (E)-(E)-hex-4-en-1-yl dodecen-10-enoate 19 (22.4 mg, 79.9 µmol) and 15.0 mL THF were added to a vial charged with a stir bar. A solution of catalyst (6.0 µmol) in 1 mL of THF was then added to this mixture. The vial was loosely capped, and the reaction was stirred at 35° C. for the reported amount of time. The vial was taken out of the glovebox and quenched with 0.5 mL butyl vinyl ether. Solvents were removed in vacuo, and the product was purified with column chromatography on silica gel (1:49 Et$_2$O: pentane) to yield the product as a colorless oil (11.3 mg, 63% yield with 2; 12.5 mg, 70% yield with 4).

$^1$H NMR (400 MHz, Chloroform-d$_1$) δ 5.51-5.32 (m, 2H), 4.18-4.09 (m, 2H), 2.38-2.29 (m, 2H), 2.25-2.15 (m, 2H), 2.08-1.99 (m, 2H), 1.81-1.73 (m, 2H), 1.67-1.58 (m, 2H), 1.39-1.22 (m, 10H).

$^{13}$C NMR (101 MHz, CDCl$_3$) δ 174.49, 131.98, 129.88, 64.31, 35.02, 31.02, 30.33, 27.86, 27.57, 27.04, 26.83, 26.64, 25.04, 24.58.

HRMS (EI+): [M]$^+$ C$_{14}$H$_{24}$O$_2$ Calculated—224.1776, Found—224.1791.

EXAMPLE 16

Synthesis of (E)-oxacyclohexadec-11-en-2-one

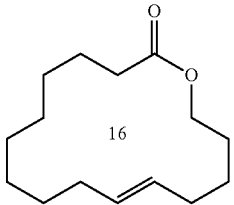

In an N$_2$-filled glovebox, (E)-(E)-hept-5-en-1-yl dodecen-10-enoate 20 (20.5 mg, 69.6 µmol) and 12.9 mL THF were added to a vial charged with a stir bar. A solution of catalyst (5.2 µmol) in 1 mL of THF was then added to this mixture. The vial was loosely capped, and the reaction was stirred at 35° C. for the reported amount of time. The vial was taken out of the glovebox and quenched with 0.5 mL butyl vinyl ether. Solvents were removed in vacuo, and the product was purified with column chromatography on silica gel (1:49 Et$_2$O: pentane) to yield the product as a colorless oil (11.0 mg, 66% yield with 2; 11.6 mg, 70% yield with 4).

$^1$H NMR (400 MHz, Chloroform-d$_1$) δ 5.37-5.23 (m, 2H), 4.12 (t, J=7.2 Hz, 2H), 2.39-2.24 (m, 2H), 2.03 (dtd, J=10.4, 5.8, 1.9 Hz, 4H), 1.70-1.55 (m, 4H), 1.42-1.21 (m, 12H).

$^{13}$C NMR (101 MHz, CDCl$_3$) δ 174.09, 131.96, 130.47, 64.10, 34.91, 32.17, 32.13, 28.47, 28.42, 28.35, 28.15, 27.35, 26.69, 25.61, 25.31.

HRMS (EI+): [M]$^+$ C$_{15}$H$_{26}$O$_2$ Calculated—238.1933, Found—238.1950.

EXAMPLE 17

Synthesis of (E)-oxacyclooctadec-1-en-2-one

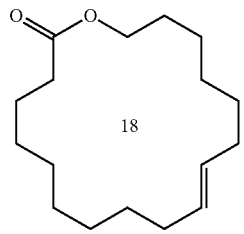

In an N$_2$-filled glovebox, (E)-(E)-non-7-en-1-yl dodecen-10-enoate 21 (23.7 mg, 73.5 μmol) and 13.7 mL THF were added to a vial charged with a stir bar. A solution of catalyst (5.5 μmol) in 1 mL of THF was then added to this mixture. The vial was loosely capped, and the reaction was stirred at 35° C. for the reported amount of time. The vial was taken out of the glovebox and quenched with 0.5 mL butyl vinyl ether. Solvents were removed in vacuo, and the product was purified with column chromatography on silica gel (1:49 Et$_2$O: pentane) to yield the product as a colorless oil (12.5 mg, 64% yield with 2; 12.3 mg, 63% yield with 4).

$^1$H NMR (400 MHz, Chloroform-d$_1$) δ 5.43-5.20 (m, 2H), 4.11 (t, J=5.9 Hz, 2H), 2.38-2.25 (m, 2H), 2.00 (p, J=6.6 Hz, 4H), 1.71-1.56 (m, 4H), 1.47-1.15 (m, 16H).

$^{13}$C NMR (101 MHz, CDCl$_3$) δ 174.22, 130.95, 130.89, 63.85, 34.51, 31.96, 31.76, 29.32, 29.32, 28.87, 28.68, 28.46, 28.20, 27.39, 27.28, 25.65, 25.53.

HRMS (EI+): [M]$^+$ C$_{17}$H$_{30}$O$_2$ Calculated—266.2246, Found—266.2226.

What is claimed is:

1. A method for producing at least one E-macrocyclic product represented by Formula (III),

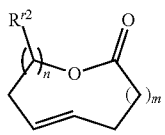

Formula (III)

wherein: R$^{r2}$ is H or linear C$_{1-3}$ alkyl; n is 1, 2, 3, 4, 5 or 6; m is 4, 5, 6, or 7; and the E-macrocyclic product of Formula (III) is a twelve, thirteen, fourteen, fifteen, sixteen or eighteen-membered ring with an E-selectivity of 95, or 98, or 99, or >99%; comprising: subjecting a diene substrate bearing two E-olefins or bearing one E-olefin and one terminal olefin, represented by Formula (II)

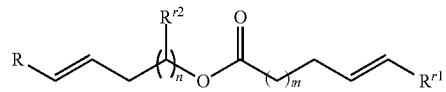

Formula (II)

wherein:

n is 1, 2, 3, 4, 5 or 6;

m is 4, 5, 6 or 7;

R is H, linear or branched C$_{1-12}$ alkyl;

R$^{r1}$ is H, linear or branched C$_{1-12}$ alkyl;

R$^{r2}$ is H or linear C$_{1-3}$ alkyl; and with the proviso that only one of R and R$^{r1}$ can be H; to a macrocyclic ring-closing metathesis reaction in the presence of a stereo-retentive ruthenium olefin metathesis catalyst represented by Formula (I),

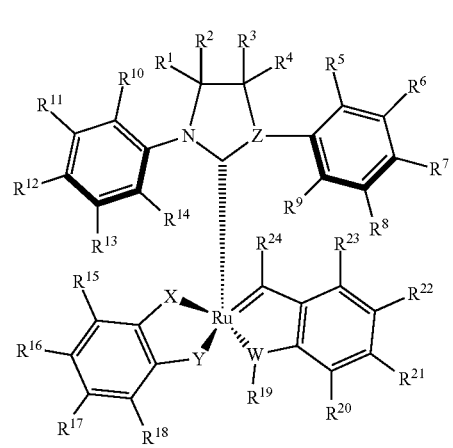

Formula (I)

wherein

X is O or S;

Y is O or S;

Z is N or CR$^{32}$;

W is O, halogen, NR$^{33}$ or S;

R$^1$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl, or together with R$^2$ can form a spiro compound or together with R$^3$ or together with R$^4$ can form a polycyclic ring;

R$^2$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl or together with R$^1$ can form a spiro compound or together with R$^3$ or together with R$^4$ can form a polycyclic ring;

R$^3$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl or optionally substituted C$_{3-8}$ cycloalkenyl or together with R$^2$ or together with R$^1$ can form a polycyclic ring or together with R$^4$ can form a spiro compound;

$R^4$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^3$ can form a spiro compound or together with $R^2$ or together with $R^1$ can form a polycyclic ring;

$R^5$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^6$ can form an optionally substituted polycyclic ring;

$R^6$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^5$ or together with $R^7$ can form an optionally substituted polycyclic ring;

$R^7$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl optionally substituted $C_{3-8}$ cycloalkenyl, or together with $R^6$ or together with $R^8$ can form an optionally substituted polycyclic ring;

$R^8$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^7$ or together with $R^9$ can form an optionally substituted polycyclic ring;

$R^9$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^8$ can form an optionally substituted polycyclic ring;

$R^{10}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ can form an optionally substituted polycyclic ring;

$R^{11}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{10}$ or together with $R^{12}$ can form an optionally substituted polycyclic ring;

$R^{12}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ or together with $R^{13}$ can form an optionally substituted polycyclic ring;

$R^{13}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{14}$ or together with $R^{12}$ can form an optionally substituted polycyclic ring;

$R^{14}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{13}$ can form a polycyclic ring;

$R^{15}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ can form an optionally substituted polycyclic ring;

$R^{16}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{15}$ or together with $R^{17}$ can form an optionally substituted polycyclic ring;

$R^{17}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ or together with $R^{16}$ can form an optionally substituted polycyclic ring;

$R^{18}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ can form an optionally substituted polycyclic ring;

$R^{19}$ is H, optionally substituted $C_{1-24}$ alkyl, —C($R^{34}$)($R^{35}$)COO$R^{36}$, —C($R^{34}$)($R^{35}$)C(O)H, —C($R^{34}$)($R^{35}$)C(O)$R^{37}$, —C($R^{34}$)($R^{35}$)C$R^{38}$(O$R^{39}$)(O$R^{40}$), —C($R^{34}$)($R^{35}$)C(O)N$R^{41}R^{42}$, —C($R^{34}$)($R^{35}$)C(O)N$R^{41}$O$R^{40}$, —C(O)$R^{25}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{33}$ can form an optionally substituted heterocyclic ring or is nil when W is halogen;

$R^{20}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ can form a polycyclic ring;

$R^{21}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{20}$ or together with $R^{22}$ can form a polycyclic ring;

$R^{22}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ or together with $R^{23}$ can form a polycyclic ring;

$R^{23}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{22}$ can form a polycyclic ring;

$R^{24}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, O$R^{30}$, N$R^{27}R^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is H, optionally substituted $C_{1-24}$ alkyl, O$R^{26}$, —N$R^{27}R^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{33}$ is H, optionally substituted $C_{1-24}$ alkyl, optionally substituted $C_{3-8}$ cycloalkyl, optionally substituted heterocycle, optionally substituted $C_{5-24}$ aryl, optionally substituted $C_{3-8}$ cycloalkenyl, or together with $R^{19}$ can form an optionally substituted heterocyclic ring;

$R^{34}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{35}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{36}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{37}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{38}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{39}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{40}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{41}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{42}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and x is 1 or 2.

2. The method according to claim 1, wherein: X is S; Y is S; Z is N or C$R^{32}$; W is O or N$R^{33}$; $R^1$ is H, linear or branched $C_{1-6}$ alkyl, or halogen; $R^2$ is H linear or branched $C_{1-6}$ alkyl, or halogen; $R^3$ is H, linear or branched $C_{1-6}$ alkyl, or halogen; $R^4$ is H, linear or branched $C_{1-6}$ alkyl or halogen; $R^5$ is H, linear or branched $C_{1-6}$ alkyl; $R^6$ is H, linear or branched $C_{1-6}$ alkyl; $R^7$ is H, linear or branched $C_{1-6}$ alkyl; $R^8$ is H or $C_{1-6}$ alkyl; $R^9$ is H, linear or branched $C_{1-6}$ alkyl; $R^{10}$ is H, linear or branched $C_{1-6}$ alkyl; $R^{11}$ is H, linear or branched $C_{1-6}$ alkyl; $R^{12}$ is H, linear or branched $C_{1-6}$ alkyl; $R^{13}$ is H, linear or branched $C_{1-6}$ alkyl or together with $R^{14}$ forms a naphthyl ring; $R^{14}$ is H, linear or branched $C_{1-6}$ alkyl or together with $R^{13}$ forms a naphthyl ring; $R^{15}$ is H, phenyl, linear or branched $C_{1-6}$ alkyl, halogen or together with $R^{16}$ forms a naphthyl ring; $R^{16}$ is H, phenyl, linear or branched $C_{1-6}$ alkyl, halogen or together with $R^{15}$ or together with $R^{17}$ forms a naphthyl ring; $R^{17}$ is H, phenyl, linear or branched $C_{1-6}$ alkyl, halogen or together with $R^{16}$ or together with $R^{18}$ forms a naphthyl ring; $R^{18}$ is H, phenyl, linear or branched $C_{1-6}$ alkyl, halogen or together with $R^{16}$ or together with $R^{18}$ forms a naphthyl ring; $R^{19}$ is H, phenyl, $C_{1-6}$ alkyl, —C($R^{34}$)($R^{35}$) COO$R^{36}$, —C($R^{34}$)($R^{35}$) C(O)H, —C($R^{34}$)($R^{35}$) C(O) $R^{37}$, —C($R^{34}$)($R^{35}$) C$R^{38}$(O$R^{39}$)(O$R^{40}$), —C($R^{34}$)($R^{35}$) C(O) N$R^{41}R^{42}$, —C($R^{34}$)($R^{35}$) C(O) N$R^{41}$O$R^{40}$ or together with $R^{33}$ forms a five, six or seven membered heterocyclic ring; $R^{20}$ is H, linear or branched $C_{1-16}$ alkyl, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, pyridine, piperidine, imidazole, indolizine, indazole, optionally substituted $C_{3-8}$ cycloalkyl, phenyl, naphthalene, cyclohexene or together with $R^{21}$ can form a polycycle; $R^{21}$ is H, phenyl, —$NR^{27}R^{28}$, linear or branched $C_{1-6}$ alkyl, halogen or together with $R^{20}$ or together with $R^{22}$ can form a polycycle; $R^{22}$ is H, linear or branched $C_{1-6}$ alkyl, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, pyridine, piperidine, imidazole, indolizine, indazole, optionally substituted $C_{3-8}$ cycloalkyl, phenyl, naphthalene, cyclohexene or together with $R^{21}$ or together with $R^{23}$ can form a polycycle; $R^{23}$ is H, phenyl, linear or branched $C_{1-6}$ alkyl or together with $R^{22}$ can form a polycycle; $R^{24}$ is H, linear or branched $C_{1-6}$ alkyl; $R^{25}$ is OH, $OR^{30}$, $NR^{27}R^{28}$, linear or branched $C_{1-6}$ alkyl; $R^{26}$ is H, linear or branched $C_{1-6}$ alkyl; $R^{27}$ is H, linear or branched $C_{1-6}$ alkyl; $R^{28}$ is H, linear or branched $C_{1-6}$ alkyl; $R^{29}$ is H, linear or branched $C_{1-6}$ alkyl, —$NR^{27}R^{28}$; $R^{30}$ is optionally substituted $C_{1-6}$ alkyl, optionally substituted $C_{3-8}$ cycloalkyl, optionally substituted heterocycle, optionally substituted phenyl or optionally substituted $C_{3-8}$ cycloalkenyl; $R^{31}$ is H, linear or branched $C_{1-6}$ alkyl; $R^{32}$ is H, linear or branched $C_{1-6}$ alkyl; $R^{33}$ is H, linear or branched $C_{1-6}$ alkyl, or together with $R^{19}$ forms a five, six or seven membered heterocyclic ring; $R^{34}$ is H, or linear or branched $C_{1-6}$ alkyl; $R^{35}$ is H, or linear or branched $C_{1-6}$ alkyl; $R^{36}$ is H, linear or branched $C_{1-6}$ alkyl; $R^{37}$ is linear or branched $C_{1-6}$ alkyl; $R^{38}$ is H or linear or branched $C_{1-6}$ alkyl; $R^{39}$ is H, linear or branched $C_{1-6}$ alkyl; $R^{40}$ is H, linear or branched $C_{1-6}$ alkyl; $R^{41}$ is H, linear or branched $C_{1-6}$ alkyl; $R^{42}$ is H, linear or branched $C_{1-6}$ alkyl; and x is 1 or 2.

3. The method according to claim 2, wherein: R is H, Me, Et, n-Pr or n-Bu; $R^{r1}$ is H, Me, Et, n-Pr or n-Bu; $R^{r2}$ is H or Me.

4. The method according to claim 3, wherein: X is S; Y is S; Z is N or $CR^{32}$; W is O, $NR^{33}$ or S; $R^1$ is Me, Et, i-Pr, n-Pr, n-Bu, t-Bu, s-Bu or H; $R^2$ is Me, Et, i-Pr, n-Pr, n-Bu, t-Bu, s-Bu or H; $R^3$ is H, Me, Et, i-Pr, n-Pr, n-Bu, t-Bu, or s-Bu; $R^4$ is H, Me, Et, i-Pr, n-Pr, n-Bu, t-Bu, or s-Bu; $R^5$ is H, F, Cl, Br, I, Me, Et, i-Pr, n-Pr, n-Bu, t-Bu, or s-Bu; $R^6$ is H, F, Cl, Br, I, Me, Et, i-Pr, n-Pr, n-Bu, t-Bu, or s-Bu; $R^7$ is H, F, Cl, Br, I, Me, Et, i-Pr, n-Pr, n-Bu, t-Bu, or s-Bu; $R^8$ is H, F, Cl, Br, I, Me, Et, i-Pr, n-Pr, n-Bu, t-Bu, or s-Bu; $R^9$ is H, F, Cl, Br, I, Me, Et, i-Pr, n-Pr, n-Bu, t-Bu, or s-Bu; $R^{10}$ is H, F, Cl, Br, I, Me, Et, i-Pr, n-Pr, n-Bu, t-Bu, or s-Bu; $R^{11}$ is H, Me, F, Cl, Br, I, Et, i-Pr, n-Pr, n-Bu, t-Bu, or s-Bu; $R^{12}$ is H, F, Cl, Br, I, Me, Et, i-Pr, n-Pr, n-Bu, t-Bu, or s-Bu; $R^{13}$ is H, Me, F, Cl, Br, I, Et, n-Pr, i-Pr, n-Bu, t-Bu or s-Bu; $R^{14}$ is F, Cl, Br, I, Me, Et, i-Pr, n-Pr, n-Bu, t-Bu, s-Bu or H; $R^{15}$ is H, Me, Et, i-Pr, n-Pr, n-Bu, t-Bu, s-Bu, F, Br, I, Cl, or together with $R^{16}$ forms a naphthyl or a phenanthryl ring; $R^{16}$ is H, F, Cl, Br, I, or together with $R^{15}$ forms a naphthyl or a phenanthryl ring; $R^{17}$ is H, F, Cl, Br, I, or together with $R^{18}$ forms a naphthyl, or a phenanthryl ring; $R^{18}$ is H, Cl, F, Br, I, 3,5-dichloro-phenyl, phenyl, Me, Et, i-Pr, n-Pr, n-Bu, t-Bu, s-Bu or together with $R^{17}$ forms a naphthyl, or a phenanthryl; $R^{19}$ is H, phenyl, $C_{1-6}$ alkyl, —$C(R^{34})(R^{35})$ $COOR^{36}$, —$C(R^{34})(R^{35})$ $C(O)H$, —$C(R^{34})(R^{35})$ $C(O)R^{37}$, —$C(R^{34})(R^{35})$ $CR^{38}(OR^{39})(OR^{40})$, —$C(R^{34})(R^{35})$ $C(O)NR^{41}R^{42}$, —$C(R^{34})(R^{35})$ $C(O)$ $NR^{41}OR^{40}$; $R^{20}$ is H, F, Cl, Br, I, Me, Et, i-Pr, n-Pr, n-Bu, t-Bu, s-Bu, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, pyridine, piperidine, imidazole, indolizine, indazole, optionally substituted $C_{3-8}$ cycloalkyl, phenyl, naphthalene, or cyclohexene; $R^{21}$ is H, phenyl, Me, Et, i-Pr, n-Pr, n-Bu, t-Bu, s-Bu, —$NR^{27}R^{28}$ F, Cl, Br, or I; $R^{22}$ is H, Me, Et, i-Pr, halogen, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, pyridine, piperidine, imidazole, indolizine, indazole, cyclohexyl, phenyl, naphthalene, cyclohexene F, Cl, Br, or I; $R^{22}$ is H, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, or —$SR^{31}$; $R^{23}$ is H, F, Cl, Br, I, phenyl, Me, Et, i-Pr, n-Pr, n-Bu, t-Bu, or s-Bu; $R^{24}$ is H; $R^{24}$ is H, or Me; $R^{25}$ is OH, $OR^{30}$, $NR^{27}R^{28}$, Me, Et, or i-Pr; $R^{26}$ is H, Me, Et, i-Pr, n-Pr, n-Bu, t-Bu, or s-Bu; $R^{27}$ is H, Me, Et, or i-Pr; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, or —$NR^{27}R^{28}$; $R^{30}$ is Me, Et, i-Pr, n-Pr, n-Bu, t-Bu, or s-Bu; $R^{31}$ is H, Me, Et, i-Pr, n-Pr, n-Bu, t-Bu, or s-Bu; $R^{32}$ is Me, Et, n-Pr or H; $R^{33}$ is H, Me, Et, Me, Et, i-Pr, n-Pr, n-Bu, t-Bu, s-Bu, or together with $R^{19}$ forms a morpholino, a thio-morpholino, a pyrrolidino, a piperidino, or a piperazino ring; $R^{34}$ is H, Me, Et, i-Pr, n-Pr, n-Bu, t-Bu, or s-Bu; $R^{35}$ is H, or Me, Et, i-Pr, n-Pr, n-Bu, t-Bu, or s-Bu; $R^{36}$ is H, Me, Et, i-Pr, n-Pr, n-Bu, t-Bu, or s-Bu; $R^{37}$ is Me, Et, i-Pr, n-Pr, n-Bu, t-Bu, or s-Bu; $R^{38}$ is H or Me, Et, i-Pr, n-Pr, n-Bu, t-Bu, or s-Bu; $R^{39}$ is H, Me, Et, i-Pr, n-Pr, n-Bu, t-Bu, or s-Bu; $R^{40}$ is H, Me, Et, i-Pr, n-Pr, n-Bu, t-Bu, or s-Bu; $R^{41}$ is H, Me, Et, i-Pr, n-Pr, n-Bu, t-Bu, or s-Bu; $R^{42}$ is H, Me, Et, i-Pr, n-Pr, n-Bu, t-Bu, or s-Bu; and x is 1 or 2.

5. The method according to claim 4, wherein R is Me; $R^{r1}$ is Me; $R^{r2}$ is H; n is 2; and m is 4, 6 or 7.

6. The method according to claim 4, wherein: R is Me; $R^{r1}$ is Me; $R^{r2}$ is H or Me; n is 1; and m is 5, 6 or 7.

7. The method according to claim 4, wherein: R is Me; $R^{r1}$ is H; $R^{r2}$ is H; n is 3; and m is 7.

8. The method according to claim 4, wherein: R is Me; $R^{r1}$ is Me; $R^{r2}$ is H; n is 5; and m is 7.

9. The method according to claim 4, wherein: R is Et; $R^{r1}$ is H; $R^{r2}$ is H; n is 1; and m is 7.

10. The method according to claim 1, wherein: X is S; Y is S; Z is N; W is O; $R^1$ is Me or H; $R^2$ is Me or H; $R^3$ is H; $R^4$ is H; $R^5$ is H, F, Me, t-Bu or i-Pr; $R^6$ is H or t-Bu; $R^7$ is H, F or Me; $R^8$ is H, F or t-Bu; $R^9$ is H, F, Me, t-Bu or i-Pr; $R^{10}$ is H, F, Me, t-Bu or i-Pr; $R^{11}$ is H or t-Bu; $R^{12}$ is H, F or Me; $R^{13}$ is H, F or t-Bu; $R^{14}$ is F, Me, i-Pr, t-Bu or H; $R^{15}$ is H, Me, F, Br, I, Cl, or together with $R^{16}$ forms a naphthyl; $R^{16}$ is H, or together with $R^{15}$ forms a naphthyl; $R^{17}$ is H or together with $R^{18}$ forms a naphthyl, or a phenanthryl ring; $R^{18}$ is Cl, F, Br, I, 3,5-dichloro-phenyl, phenyl, t-Bu or together with $R^{17}$ forms a naphthyl, or a phenanthryl ring; $R^{19}$ is i-Pr; $R^{20}$ is H or phenyl; $R^{21}$ is H; $R^{22}$ is H, —$C(O)R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$; $R^{23}$ is H; $R^{24}$ is H; $R^{25}$ is OH, $OR^{30}$, $NR^{27}R^{28}$, Me, Et, or i-Pr; $R^{26}$ is H, Me, Et, i-Pr, n-Pr, n-Bu, t-Bu, or s-Bu; $R^{27}$ is H, Me, Et, i-Pr, n-Pr, n-Bu, t-Bu, or s-Bu; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, —$NR^{27}R^{28}$; $R^{30}$ is Me, Et, i-Pr, n-Pr, n-Bu, t-Bu, or s-Bu; and $R^{31}$ is H, Me, Et, i-Pr, n-Pr, n-Bu, t-Bu, or s-Bu.

11. The method according to claim 9, wherein R is Me; $R^{r1}$ is Me; $R^{r2}$ is H; n is 2; and m is 4, 6 or 7.

12. The method according to claim 9, wherein: R is Me; $R^{r1}$ is Me; $R^{r2}$ is H or Me; n is 1; and m is 5, 6 or 7.

13. The method according to claim 9, wherein: R is Me; $R^{r1}$ is H; $R^{r2}$ is H; n is 3; and m is 7.

14. The method according to claim 9, wherein: R is Me; $R^{r1}$ is H; $R^{r2}$ is H; n is 5; and m is 7.

15. The method according to claim 1, wherein: X is S; Y is S; Z is N; W is O; $R^1$ is Me; $R^2$ is Me; $R^3$ is H; $R^4$ is H; $R^5$ is F; $R^6$ is H; $R^7$ is H or F; $R^8$ is H; $R^9$ is F; $R^{10}$ is F; $R^{11}$ is H; $R^{12}$ is H; $R^{13}$ is H; $R^{14}$ is F; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

16. The method according to claim 1, wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

* * * * *